United States Patent
Wu et al.

(10) Patent No.: US 12,325,880 B2
(45) Date of Patent: Jun. 10, 2025

(54) IDENTIFICATION OF PDE3 MODULATOR RESPONSIVE CANCERS

(71) Applicant: THE BROAD INSTITUTE, INC., Cambridge, MA (US)

(72) Inventors: Xiaoyun Wu, Cambridge, MA (US); Heidi Greulich, Cambridge, MA (US)

(73) Assignee: THE BROAD INSTITUTE, INC., Cambridge, MA (US)

( * ) Notice: Subject to any disclaimer, the term of this patent is extended or adjusted under 35 U.S.C. 154(b) by 1048 days.

(21) Appl. No.: 17/290,673

(22) PCT Filed: Nov. 1, 2019

(86) PCT No.: PCT/US2019/059526
§ 371 (c)(1),
(2) Date: Apr. 30, 2021

(87) PCT Pub. No.: WO2020/092998
PCT Pub. Date: May 7, 2020

(65) Prior Publication Data
US 2021/0371935 A1 Dec. 2, 2021

Related U.S. Application Data

(60) Provisional application No. 62/901,090, filed on Sep. 16, 2019, provisional application No. 62/754,290, filed on Nov. 1, 2018.

(51) Int. Cl.
*C12Q 1/6886* (2018.01)
*A61K 31/50* (2006.01)
*A61P 35/00* (2006.01)

(52) U.S. Cl.
CPC ............ *C12Q 1/6886* (2013.01); *A61K 31/50* (2013.01); *A61P 35/00* (2018.01); *C12Q 2600/106* (2013.01); *C12Q 2600/158* (2013.01)

(58) Field of Classification Search
CPC ....................................................... A61P 35/00
See application file for complete search history.

(56) References Cited

U.S. PATENT DOCUMENTS

| | | |
|---|---|---|
| 2011/0257034 A1 | 10/2011 | Barany et al. |
| 2018/0045727 A1 | 2/2018 | Spetzler et al. |
| 2018/0153975 A1 | 6/2018 | Fritsch et al. |
| 2018/0235961 A1 | 8/2018 | De Waal et al. |
| 2020/0247783 A1 | 8/2020 | Ellermann et al. |
| 2020/0369633 A1 | 11/2020 | Ellermann et al. |

FOREIGN PATENT DOCUMENTS

| | | |
|---|---|---|
| WO | 2017027854 A1 | 2/2017 |
| WO | 2018141835 A1 | 8/2018 |
| WO | 2019025562 A1 | 2/2019 |

OTHER PUBLICATIONS

Vandenberghe et al., "Phosphodiesterase 3A: a new player in development of interstitial cells of Cajal and a prospective target in gastrointestinal stromal tumors (GIST)," Oncotarget 2017;8(25):41026-43. PMID: 28454120. (Year: 2017).*
Lewis et al., "Optimization of PDE3A Modulators for SLFN12-Dependent Cancer Cell Killing," ACS Med. Chem. Lett. 2019;10(11):1537-42. PMID: 31749907 (Year: 2019).*
Sanson et al., "Optimized libraries for CRISPR-Cas9 genetic screens with multiple modalities," Nature Communications, 2018, vol. 9, Article No. 5416, pp. 1-15.
Trivellin et al., "AIP and its interacting partners," Journal of Endocrinology, 2011, vol. 210, pp. 137-155.
International Search Report and Written Opinion in corresponding International Patent Application No. PCT/US2019/059526, mailed Jan. 30, 2020 (13 pages).
Francis et al., "Mammalian cyclic nucleotide phosphodiesterases: molecular mechanisms and physiological functions," Physiological Reviews, Apr. 30, 2011 (Apr. 30, 2011), vol. 91, No. 2, pp. 651-690.
Hirsch et al., "Twice upon a time: PI3K's secret double life exposed," Trends in Biomedical Sciences, Apr. 17, 2009 (Apr. 17, 2009), vol. 34, No. 5, pp. 244-248.
Extended European Search Report dated Jun. 30, 2022 in corresponding European Patent Application No. 19878032.2 (8 pages).
Office Action dated Nov. 1, 2023 in corresponding Canadian Patent Application No. 3,122,378 (3 pages).

\* cited by examiner

*Primary Examiner* — Theodore R. Howell
(74) *Attorney, Agent, or Firm* — Greenberg Traurig, LLP; Melissa Hunter-Ensor; Scott Goncher

(57) ABSTRACT

The present disclosure features methods for identifying pateints having a hyperproliferative disease, disorder, or condition responsive to phosphodiesterase 3 (PDE3) and schlafen family member 12 (SLFN12) complex formation. The hyperproliferative disease, disorder, or condition may be cancer in a patient including glioblastoma, melanoma, ovarian cancer, cervical cancer, sarcoma, or hematopoietic cancers, such as acute myeloid leukemia. Those responsive diseases, disorders, or conditions may be identified using the biomarker AIP and/or TRRAP in combination with those biomarkers pertinent to phosphodieseterase 3 and schlafen family member 12 complexes which may be formed by PDE3 modulation with certain active compounds. Expression of combinations of these biomarkers have been shown to correlate with active compound (e.g., PDE3 modulator, PDE3A modulator, PDE3B modulator) sensitivity.

13 Claims, 13 Drawing Sheets
Specification includes a Sequence Listing.

IDENTIFICATION OF PDE3 MODULATOR RESPONSIVE CANCERS

CROSS REFERENCE TO RELATED APPLICATIONS

The present application is the U.S. national phase application, pursuant to 35 U.S.C. § 371, of PCT International Application No. PCT/US2019/059526, filed Nov. 1, 2019, designating the United States and published in English, which claims the benefit of and priority under 35 U.S.C. § 119 to U.S. App. No. 62/901,090, filed Sep. 16, 2019 and U.S. App. No. 62/754,290, filed Nov. 1, 2018, each of which is hereby incorporated by reference in its entirety.

FIELD OF DISCLOSURE

The present disclosure relates to the identification of cells (e.g., cancer cells) responsive to complex formation between certain phosphodiesterase 3 proteins (e.g., PDE3A, PDE3B) and schlafen family member 12 (SLFN12) proteins by identifying cells that express certain biomarkers implicated in complex formation. Specifically, cells identified as expressing the aryl hydrocarbon receptor interacting protein (AIP) and/or transformation/transcription domain associated protein (TRRAP) are implicated in the complex formation which results in apoptosis. Methods of treatment or prevention of hyperproliferative diseases, disorders, or conditions associated with these cells are also provided comprising administration of certain chemical agents (e.g., PDE3A modulators) to those cells identified as responsive to complex formation.

BACKGROUND

Cancer kills over 550,000 people in the United States and over 8 million people world-wide each year. New agents, including small molecules, molecules that impact tissue-specific growth requirements, and immunomodulatory agents, have been shown to benefit a subset of patients whose cancers have unique genomic mutations or other characteristics. Unfortunately, many cancer patients are still left without effective therapeutic options.

One approach to identify new anti-cancer agents is phenotypic screening to discover novel small molecules displaying strong selectivity between cancer cell lines, followed by predictive chemogenomics to identify the cell features associated with drug response. In the 1990s, Weinstein and colleagues demonstrated that the cytotoxic profile of a compound can be used to identify cellular characteristics, such as gene-expression profiles and DNA copy number, that correlate with drug sensitivity. The ability to identify the features of cancer cell lines that mediate their response to small molecules has strongly increased in recent years with automated high-throughput chemosensitivity testing of large panels of cell lines coupled with comprehensive genomic and phenotypic characterization of the cell lines. Phenotypic observations of small-molecule sensitivity can be linked to expression patterns or somatic alterations.

Despite advances in targeted therapies and immunotherapies, certain cancers, such as metastatic melanoma, remain deadly diseases. For example, metastatic melanoma has a 5-year survival rate of only 20%. New therapeutic modalities are therefore needed. These new modalities may be based on new mechanisms of cancer cell killing. For example, some phosphodiesterase 3A (PDE3A) modulators may cause complex formation between PDE3A peptide and schlafen family member 12 (SLFN12) or similar complex formation between PDE3B peptide and schlafen family member 12 (SLFN12) in cancer cells. This complex formation may result in induction of apoptosis. However, inhibition of PDE3 enzymatic activity alone is insufficient to cause cancer cell killing, as neither PDE3 knockout nor treatment with most previously-characterized PDE3A inhibitors kills cancer cells. Thus, in contrast to traditional targeted therapies that leverage cancer cell dependencies created by genomic alteration, these PDE3 modulation therapies cause induced apoptosis via PDE3A-SLFN12 or PDE3B-SLFN12 ("PDE3A/B-SLFN12") complex formation. Moreover, such apoptotic induction does not occur in all cancer cells expressing PDE3A and SLFN12 indicating an incomplete understanding of the mechanistic underpinnings of this cell death.

Methods of characterizing malignancies at a molecular level are useful for stratifying patients, thereby quickly directing them to effective therapies. Improved methods for predicting the responsiveness of subjects having cancer are urgently required.

SUMMARY

In accordance with the foregoing objectives and others, the present disclosure provides methods of identifying cells of a hyperproliferative disease, disorder, or condition, such as cancer cells responsive to PDE3A-SLFN12 complex formation or PDE3B-SLFN12 complex formation, methods for the treatment or prophylaxis of hyperproliferative diseases, disorders, or conditions identified as being responsive to complex formation, and kits for the determination and treatment of hyperproliferative diseases, disorders, or conditions identified as being responsive to complex formation. Without wishing to be bound by theory, it is believed that cells lacking the aryl hydrocarbon receptor interacting protein (AIP) and/or the transformation/transcription domain associated protein (TRRAP) have decreased or no sensitivity to complex formation or have decreased or no complex formation following contact of the cell with an active compound that typically induces such formation. Certain PDE3 modulatory compounds (e.g., PDE3A modulators, PDE3B modulators, DNMDP, compounds disclosed in WO2019/025562, which is hereby incorporated by reference in its entirety and particularly in relation to compounds of general formula (1), may be able to induce complex formation between PDE3A and SLFN12 or PDE3B and SLFN12 in cancer cells when those cells express AIP and/or TRRAP, which may result apoptosis of the cancer cells.

Apoptosis may be induced in cells expressing the AIP polypeptide or polynucleotide particularly in relation to cells expressing schlafen family 12 (SLFN12) and phosphodiesterase 3A (PDE3A) or cells expressing schlafen family member 12 (SLFN12) and phosphodiesterase 3B (PDE3B) since AIP is implicated in PDE3A-SLFN12 or PDE3B-SLFN12 complex formation. It has also been found that apoptosis may be induced in cells expressing transformation/transcription domain associated protein (TRRAP) polypeptide or polynucleotide in relation to cells expressing schlafen family member 12 (SLFN12) and phosphodiesterase 3A (PDE3A) or cells expressing schlafen family member 12 (SLFN12) and phosphodiesterase 3B (PDE3B) since TRRAP is implicated in formation of or response to complex formation as well.

Methods of identifying a subject having a hyperproliferative disease, disorder, or condition, such as a cancer responsive to PDE3A-SLFN12 complex formation or PDE3B-SLFN12 complex formation, are provided comprising detecting:
  (i) the expression of aryl hydrocarbon receptor interacting protein (AIP) polypeptides or polynucleotides and/or transformation/transcription domain associated protein (TRRAP) polypeptides or polynucleotides;
  (ii) the expression of phosphodiesterase 3A (PDE3A) polypeptides or polynucleotides or the expression of phosphodiesterase 3B (PDE3B) polypeptides or polynucleotides in the cells relative to a reference, and
  (iii) the expression of schlafen family member 12 (SLFN12) polypeptides or polynucleotides in the cells relative to a reference;
wherein the hyperproliferative disease, disorder, or condition is characterized as responsive to the complex formation complex formation if:
  (i) AIP and/or TRRAP are expressed,
  (ii) the expression of PDE3A and/or PDE3B is increased relative to the reference, and
  (iii) the expression of SLFN12 is increased relative to the reference.

In certain implementations, the method may comprise obtaining one or more cells (e.g., cancer cells) of the hyperproliferative disease, disorder, or condition from the subject and detecting:
  (i) the expression of aryl hydrocarbon receptor interacting protein (AIP) polypeptides or polynucleotides and/or transformation/transcription domain associated protein (TRRAP) polypeptides or polynucleotides;
  (ii) the expression of phosphodiesterase 3A (PDE3A) polypeptides or polynucleotides or the expression of phosphodiesterase 3B (PDE3B) polypeptides or polynucleotides in the cells relative to a reference, and
  (iii) the expression of schlafen family member 12 (SLFN12) polypeptides or polynucleotides in the cells relative to a reference;
wherein the hyperproliferative disease, disorder, or condition is characterized as responsive to the complex formation complex formation if:
  (i) AIP and/or TRRAP are expressed,
  (ii) the expression of PDE3A and/or PDE3B is increased relative to the reference, and
  (iii) the expression of SLFN12 is increased relative to the reference.

In some embodiments, the hyperproliferative disease, disorder, or condition is characterized as responsive to complex formation if both AIP and TRRAP are expressed in the cells. In certain implementations, expression of AIP and/or TRRAP may be determined by comparison of expression to the reference and the hyperprofliferative disease, disorder, or condition is characterized as responsive to complex formation if:
  (i) there is no loss of AIP and/or TRRAP expression relative to the reference (e.g., the expression levels of AIP and/or TRRAP in the cell is more than 50% of the expression level in the reference or more than 90% of the expression levels in the reference or more than 100% of the expression levels in the reference),
  (ii) the expression of PDE3A is increased relative to the reference, and
  (iii) the expression of SLFN12 is increased relative to the reference. In some embodiments, the method of identifying a subject having a hyperproliferative disease, disorder, or condition, such as cancer responsive to PDE3A-SLFN12 complex formation, may comprise obtaining one or more cells (e.g., cancer cells) of the hyperproliferative disease, disorder, or condition from the subject and detecting:
  (i) the expression of aryl hydrocarbon receptor interacting protein (AIP) polypeptides or polynucleotides and/or transformation/transcription domain associated protein (TRRAP) polypeptides or polynucleotides,
  (ii) the expression of phosphodiesterase 3A (PDE3A) polypeptides or polynucleotides relative to a reference, and
  (iii) the expression of schlafen family member 12 (SLFN12) polypeptides or polynucleotides relative to a reference;
wherein the hyperproliferative disease, disorder, or condition is characterized as responsive to said complex formation if:
  (i) AIP and/or TRRAP are expressed,
  (ii) the expression of PDE3A is increased relative to the reference, and
  (iii) the expression of SLFN12 is increased relative to the reference. In some embodiments, the hyperproliferative disease, disorder, or condition is characterized as responsive to complex formation if both AIP and TRRAP are expressed.

In various implementations, the method of identifying a subject having a hyperproliferative disease, disorder, or condition, such as cancer responsive to PDE3B-SLFN12 complex formation, may comprise obtaining one or more cells (e.g., cancer cells) of the hyperproliferative disease, disorder, or condition from the subject and detecting:
  (i) the expression of aryl hydrocarbon receptor interacting protein (AIP) polypeptides or polynucleotides and/or transformation/transcription domain associated protein (TRRAP) polypeptides or polynucleotides,
  (ii) the expression of phosphodiesterase 3B (PDE3B) polypeptides or polynucleotides relative to a reference, and
  (iii) the expression of schlafen family member 12 (SLFN12) polypeptides or polynucleotides relative to a reference;
wherein the hyperproliferative disease, disorder, or condition is characterized as responsive to said complex formation complex formation if:
  (i) AIP and/or TRRAP are expressed,
  (ii) the expression of PDE3B is increased relative to the reference, and
  (iii) the expression of SLFN12 is increased relative to the reference. In some embodiments, the hyperproliferative disease, disorder, or condition is characterized as responsive to chemically induced complex formation if both AIP and TRRAP are expressed.

The cells of the subject may be collected from a tissue sample, a blood sample, or a plasma sample.

Methods of killing or reducing the survival of a cell (e.g., cancer cell) are also provided wherein the cancer cell is selected as responsive to PDE3A/B-SLFN12 complex formation comprising contacting the cancer cell with a PDE3 modulator (e.g., a PDE3A modulator, a PDE3B modulator), wherein the cell is selected as responsive to the PDE3A/B-SLFN12 complex formation when the cell expresses AIP and/or TRRAP polypeptides or polynucleotides, has increased expression of SLNF12 polypeptides or polynucleotides relative to a reference, and has increased expression of PDE3A or PDE3B relative to the reference. Typically, the PDE3 modulator (e.g., PDE3A modulator, PDE3B modulator) may be able to induce PDE3A/B-SLFN12 complex formation leading to apoptosis of the cell following contact.

In some embodiments, the cancer cell is selected as responsive to PDE3A-SLFN12 complex formation if the cell has increased expression of PDE3A and increased expression of SLFN12 relative to a reference. In some embodiments, the cell is selected as responsive to PDE3B-SLFN12 complex formation if the cell has increased expression of PDE3B and SLFN12 relative to a reference. Many PDE3A modulators also directly bind PDE3B proteins and a PDE3A modulator may be used to induce complexation between SLFN12 and PDE3B.

In some embodiments, methods for the treatment or prevention of hyperproliferative disease, disorder, or condition (e.g. cancer) in a subject are provided comprising administering to the subject a PDE3 modulator (e.g., PDE3A modulators, PDE3B modulators), wherein the subject is identified as having a hyperproliferative disease, disorder, or condition that is responsive to the PDE3 modulator by obtaining one or more cells of the hyperproliferative disease, disorder, or condition (e.g. cancer) from the subject (e.g., by obtaining a sample from the subject) and detecting:
 (i) the expression of aryl hydrocarbon receptor interacting protein (AIP) polypeptides or polynucleotides and/or transformation/transciption domain associated protein (TRRAP) polypeptides or polynucleotides,
 (ii) the expression of phosphodiesterase 3B (PDE3B) polypeptides or polynucleotides relative to a reference, and
 (iii) the expression of Schlafen family member 12 (SLFN12) polypeptides or polynucleotides relative to a reference;
wherein the hyperproliferative disease, disorder, or condition is characterized as responsive to said complex formation complex formation if:
 (i) AIP and/or TRRAP are expressed,
 (ii) the expression of PDE3B is increased relative to the reference, and
 (iii) the expression of SLFN12 is increased relative to the reference. In some embodiments, the hyperproliferative disease, disorder, or condition is characterized as responsive to the PDE3 modulator if both AIP and TRRAP are expressed. The PDE3A modulator may comprise, for example, 6-(4-(diethylamino)-3-nitrophenyl)-5-methyl-4,5-dihydropyridazin-3(2H)-one (DNMDP). In certain implementations, expression of AIP and/or TRRAP may be determined by comparison of expression to the reference and the hyperprolfiferative disease, disorder, or condition is characterized as responsive to complex formation if:
 (i) there is no loss of AIP and/or TRRAP expression relative to the reference (e.g., the expression levels of AIP and/or TRRAP in the cell is more than 50% of the expression levels in the reference or more than 90% of the expression levels in the reference or more than 100% of the expression levels in the reference),
 (ii) the expression of PDE3A is increased relative to the reference, and
 (iii) the expression of SLFN12 is increased relative to the reference.

The expression of any biomarker (e.g., AIP, TRRAP, PDE3A, PDE3B, SLFN12) may be detected by a method selected from the group consisting of immunoblotting, mass spectrometry, immunoprecipitation quantitative PCR, Northern Blot, microarray, enzyme-linked immunosorbent assay (ELISA), in situ hybridization, and combinations thereof. In certain implementations, expression of AIP and/or TRRAP may be determined by comparison to the reference. The cancer cell may be considered to express AIP and/or TRRAP if there is no loss in expression as compared to the reference. In certain implementations, expression of AIP and/or TRRAP may be determined by comparison to the reference and the cell is considered to express AIP and/or TRRAP if there is a small difference (e.g., the cancer cell copy number is within 10% of the copy number of the reference, the cancer cell copy number is within 5% of the reference) between expression in the cancer cell and the reference. Genomics may be used to determine expression and relative expression levels. For example, the cell may be considered to not express AIP and/or TRRAP if the number of copies of the biomarker per cellular genome is less than 1 or less than $2^{-1}$ or less than $2^{-2}$ or less than $2^{-3}$ or less than $2^{-4}$ or less than $2^{-5}$. Conversely, the cell may be considered to express AIP and/or TRRAP if the number of copies of the biomarker per cellular genome is greater than 1 or greater than $2^{-1}$ or greater than $2^{-2}$ or greater than $2^{-3}$ or greater than $2^{-4}$ or greater than $2^{-5}$.

Such methods allow for the treatment and/or prevention of hyperproliferative disease, disorders, or conditions caused by the proliferation of cells responsive to complex formation and, in particular, complex formation induced by PDE3 modulation. In some embodiments, the cell is a cancer cell. For example, the hyperproliferative disease, disorder, or condition may be selected from bladder, brain, breast, cervical, colorectal, endometrial, esophageal, gallbladder, gastric, glioblastoma, kidney, leukemia (e.g., acute myelogenous leukemia, chronic myelogenous leukemia, chronic lymphocytic leukemia), liver (e.g., hepatocellular carcinoma, intrahepatic cholangiocarcinoma, angiosarcoma, hemangiosarcoma, hepatoblastoma), lung (e.g., non-small cell lung cancer, small cell lung cancer, mesothelioma), melanoma, ovarian, pancreatic, prostate, multiple myeloma, sarcoma (e.g., osteosarcoma, soft-tissue sacrcoma), thyroid, urinary tract, or uterine cancer. In certain implementations the cancer may be a hematopoietic cancer, such as acute lymphoblastic leukemia, acute myelogenous leukemia, chronic lymphocytic leukemia, chronic myelogenous leukemia, acute monocytic leukemia, Hodgkin's lymphoma, or non-Hodgkin's lymphoma.

Various routes of administration are useful for treatment modalities. In some embodiments, the PDE3 modulator (e.g., PDE3A modulator, PDE3B modulator) is administered orally. In other embodiments, the PDE3 modulator is administered by intravenous injection.

Kits for identifying a subject having cancer as responsive to complex formation including chemically induced complex formation (e.g., cells responsive to PDE3 modulators, cells responsive to PDE3A modulators, cells responsive to PDE3B modulators) are also provided, wherein the kit comprises a first capture reagent that binds AIP polypeptide and/or a second capture reagent that binds TRRAP polypeptide. In some embodiments, the kit comprises a third capture reagent that binds PDE3A polypeptide and/or a fourth capture reagent that binds SLFN12 polypeptide and/or a fifth capture reagent that binds PDE3B. In some embodiments, the kit further comprises a PDE3 modulator (e.g., PDE3A modulator, PDE3B modulator), such as DNMDP or a compound of WO2019/025562. It will be understood that the numeric identifiers for the capture reagents (e.g., first, second, third, fourth, fifth) do not indicate the total quantity of capture reagents in each kit. The PDE3 modulator may be present in a pharmaceutical formulation sufficient to deliver a therapeutically effective amount to a subject in need thereof.

In one embodiment, a cancer expressing AIP, which is required for SLFN12/PDE3A complex formation, is identified as responsive to treatment with compound X ((6S)-5-[4'-fluoro-2-(trifluoromethyl)biphenyl-4-yl]-6-methyl-3,6-dihydro-2H-1,3,4-oxadiazin-2-one).

BRIEF DESCRIPTION OF FIGURES

As shown in FIG. 2A, UACC257 does not have sensitivity to DNMDP.

FIG. 8A shows that cervical cancer cell viability is reduced at increasing concentration of Compound X. This effect is not observed when AIP is knocked out using CRISPR (KOsg2, KOsg3). FIG. 8B is an image of an immunoblot. An anti-PDE3A antibody was used to pull down a PDE3A-SLFN12 complex. Complex formation between PDE3A and FLAG-tagged SLFN12 was induced in the presence of Compound X and in the presence of DNMDP. Complex formation was not observed when AIP was knocked out using Crispr (KO sg2, KO sg3). HeLa cells were treated with 10 µM DNMDP or 10 µM Compound X.

DETAILED DESCRIPTION

Definitions

Figure 1:
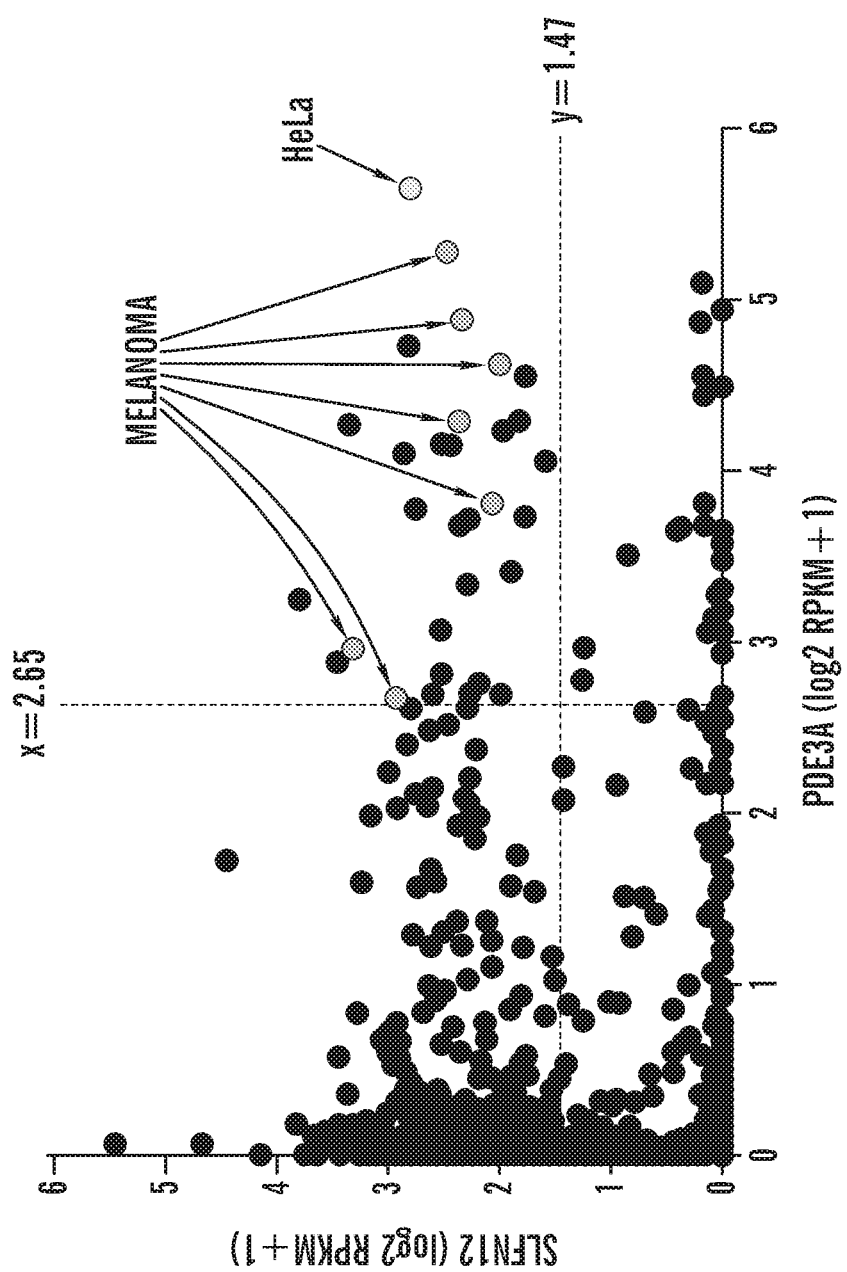
FIG. 1 illustrates the reads per kilobase of transcript per million mapped reads (RPKM) for the 49 cell lines measured for PDE3A sensitivity and identifies the biomarker positive cancer cell lines in addition to the HeLa cells. A high proportion of biomarker-positive cell lines are from melanoma patients.

Detailed embodiments of the present disclosure are disclosed herein; however, it is to be understood that the disclosed embodiments are merely illustrative of the disclosure that may be embodied in various forms. In addition, each of the examples given in connection with the various embodiments of the disclosure is intended to be illustrative, and not restrictive.

All terms used herein are intended to have their ordinary meaning in the art unless otherwise provided. All concentrations are in terms of percentage by weight of the specified component relative to the entire weight of the topical composition, unless otherwise defined.

As used herein, "a" or "an" shall mean one or more. As used herein when used in conjunction with the word "comprising," the words "a" or "an" mean one or more than one. As used herein "another" means at least a second or more.

As used herein, all ranges of numeric values include the endpoints and all possible values disclosed between the disclosed values. The exact values of all half integral numeric values are also contemplated as specifically disclosed and as limits for all subsets of the disclosed range. For example, a range of from 0.1% to 3% specifically discloses a percentage of 0.1%, 1%, 1.5%, 2.0%, 2.5%, and 3%. Additionally, a range of 0.1 to 3% includes subsets of the original range including from 0.5% to 2.5%, from 1% to 3%, and from 0.1% to 2.5%. It will be understood that the sum of all weight % of individual components will not exceed 100%.

By "PDE3A polynucleotide" is meant any nucleic acid molecule encoding a PDE3A polypeptide or fragment thereof. An exemplary PDE3A nucleic acid sequence is provided at NCBI Ref: NM_000921.4:

(SEQ ID NO: 1)

```
  1 gggggccact gggaattcag tgaagagggc accctatacc atggcagtgc ccggcgacgc 61 tgcacgagtc agggacaagc ccgtccacag tggggtgagt caagccccca cggcgggccg 121 ggactgccac catcgtgcgg accccgcatc gccgcgggac tcgggctgcc gtggctgctg 181 gggagacctg gtgctgcagc cgctccggag ctctcggaaa ctttcctccg cgctgtgcgc 241 gggctccctg tcctttctgc tggcgctgct ggtgaggctg gtccgcgggg aggtcggctg 301 tgacctggag cagtgtaagg aggcggcggc ggcggaggag gaggaagcag ccccgggagc 361 agaaggggc gtcttcccgg ggcctcgggg aggtgctccc gggggcggtg cgcggctcag
```

-continued

```
 421 cccctggctg cagccctcgg cgctgctctt cagtctcctg tgtgccttct tctggatggg
 481 cttgtacctc ctgcgcgccg ggtgcgcct gcctctggct gtcgcgctgc tggccgcctg
 541 ctgcgggggg gaagcgctcg tccagattgg gctgggcgtc ggggaggatc acttactctc
 601 actccccgcc gcggggtgg tgctcagctg cttggccgcc gcgacatggc tggtgctgag
 661 gctgaggctg ggcgtcctca tgatcgcctt gactagcgcg gtcaggaccg tgtccctcat
 721 ttccttagag aggttcaagg tcgcctggag accttacctg cgtacctgc ccggcgtgct
 781 ggggatcctc ttggccaggt acgtggaaca atcttgccg cagtccgcgg aggcggctcc
 841 aagggagcat tggggtcccc agctgattgc tgggaccaag gaagatatcc cggtgtttaa
 901 gaggaggagg cggtccagct ccgtcgtgtc cgccgagatg tccggctgca gcagcaagtc
 961 ccatcggagg acctccctgc cctgtatacc gagggaacag ctcatggggc attcagaatg
1021 ggaccacaaa cgagggccaa gaggatcaca gtcttcagga accagtatta ctgtggacat
1081 cgccgtcatg ggcgaggccc acggcctcat taccgacctc ctggcagacc cttctcttcc
1141 accaaacgtg tgcacatcct tgagagccgt gagcaacttg ctcagcacac agctcacctt
1201 ccaggccatt cacaagccca gagtgaatcc cgtcacttcg ctcagtgaaa actatacctg
1261 ttctgactct gaagagagct ctgaaaaaga caagcttgct attccaaagc gcctgagaag
1321 gagtttgcct cctggcttgt tgagacgagt ttcttccact tggaccacca ccacctcggc
1381 cacaggtcta cccaccttgg agcctgcacc agtacggaga gaccgcagca ccagcatcaa
1441 actgcaggaa gccccttcat ccagtcctga ttcttggaat aatccagtga tgatgaccct
1501 caccaaaagc agatccttta cttcatccta tgctatttct gcagctaacc atgtaaaggc
1561 taaaaagcaa agtcgaccag gtgccctcgc taaaatttca cctctttcat cgccctgctc
1621 ctcacctctc caagggactc ctgccagcag cctggtcagc aaaatttctg cagtgcagtt
1681 tccagaatct gctgacacaa ctgccaaaca aagcctaggt tctcacaggg ccttaactta
1741 cactcagagt gccccagacc tatcccctca aatcctgact ccacctgtta tatgtagcag
1801 ctgtggcaga ccatattccc aagggaatcc tgctgatgag cccctggaga gaagtggggt
1861 agccactcgg acaccaagta gaacagatga cactgctcaa gttacctctg attatgaaac
1921 caataacaac agtgacagca gtgacattgt acagaatgaa gatgaaacag agtgcctgag
1981 agagcctctg aggaaagcat cggcttgcag cacctatgct cctgagacca tgatgtttct
2041 ggacaaacca attcttgctc ccgaacctct tgtcatggat aacctggact caattatgga
2101 gcagctaaat acttggaatt ttccaatttt tgatttagtg aaaatatag gaagaaaatg
2161 tggccgtatt cttagtcagg tatcttacag actttttgaa gacatgggcc tctttgaagc
2221 ttttaaaatt ccaattaggg aattatgaa ttatttcat gctttggaga ttggatatag
2281 ggatattcct tatcataaca gaatccatgc cactgatgtt ttacatgctg tttggtatct
2341 tactacacag cctattccag gcctctcaac tgtgattaat gatcatggtt caaccagtga
2401 ttcagattct gacagtggat ttacacatgg acatatggga tatgtattct caaaaacgta
2461 taatgtgaca gatgataaat acgatgtct gtctgggaat atccctgcct tggagttgat
2521 ggcgctgtat gtggctgcag ccatgcacga ttatgatcat ccaggaagga ctaatgcttt
2581 cctggttgca actagtgctc ctcaggcggt gctatataac gatcgttcag ttttggagaa
2641 tcatcacgca gctgctgcat ggaatctttt catgtcccgg ccagagtata acttcttaat
2701 taaccttgac catgtggaat ttaagcattt ccgtttcctt gtcattgaag caattttggc
2761 cactgacctg aagaaacact ttgacttcgt agccaaattt aatggcaagg taaatgatga
```

-continued

```
2821 tgttggaata gattggacca atgaaaatga tcgtctactg gtttgtcaaa tgtgtataaa 2881 gttggctgat atcaatggtc cagctaaatg taaagaactc catcttcagt ggacagatgg 2941 tattgtcaat gaattttatg aacagggtga tgaagaggcc agccttggat tacccataag 3001 cccccttcatg gatcgttctg ctcctcagct ggccaacctt caggaatcct tcatctctca 3061 cattgtgggg cctctgtgca actcctatga ttcagcagga ctaatgcctg gaaaatgggt 3121 ggaagacagc gatgagtcag gagatactga tgacccagaa gaagaggagg aagaagcacc 3181 agcaccaaat gaagaggaaa cctgtgaaaa taatgaatct ccaaaaaaga gactttcaa 3241 aaggagaaaa atctactgcc aaataactca gcacctctta cagaaccaca gatgtggaa 3301 gaaagtcatt gaagaggagc aacggttggc aggcatagaa atcaatccc tggaccagac 3361 ccctcagtcg cactcttcag aacagatcca ggctatcaag gaagaagaag aagagaaagg 3421 gaaaccaaga ggcgaggaga taccaaccca aaagccagac cagtgacaat ggatagaatg 3481 ggctgtgttt ccaaacagat tgacttgtca aagactctct tcaagccagc acaacattta 3541 gacacaacac tgtagaaatt tgagatgggc aaatggctat tgcattttgg gattcttcgc 3601 attttgtgtg tatattttta cagtgaggta cattgttaaa aacttttttgc tcaaagaagc 3661 tttcacattg caacaccagc ttctaaggat tttttaagga gggaatatat atgtgtgtgt 3721 gtatataagc tcccacatag atacatgtaa aacatattca cacccatgca cgcacacaca 3781 tacacactga aggccacgat tgctggctcc acaatttagt aacatttata ttaagatata 3841 tatatagtgg tcactgtgat ataataaatc ataaaggaaa ccaaatcaca aaggagatgg 3901 tgtggcttag caaggaaaca gtgcaggaaa tgtaggttac caactaagca gcttttgctc 3961 ttagtactga gggatgaaag ttccagagca ttatttgaat tctgatacat cctgccaaca 4021 ctgtgtgtgt gtgtgtgtgt gtgtgtgtgt gtgtgtgtgt gtgtgaaaga gagacagaag 4081 ggaatggttt gagagggtgc ttgtgtgcat gtgtgtgcat atgtaaagag attttgtgg 4141 tttaagtaac tcagaatagc tgtagcaaat gactgaatac atgtgaacaa acagaaggaa 4201 gttcactctg gagtgtcttt gggaggcagc cattccaaat gccctcctcc atttagcttc 4261 aataaagggc cttttgctga tggagggcac tcaagggctg ggtgagaggg ccacgtgttt 4321 ggtattacat tactgctatg caccacttga aggagctcta tcaccagcct caaacccgaa 4381 agactgaggc attttccagt ctacttgcct aatgaatgta taggaactgt ctatgagtat 4441 ggatgtcact caactaagat caaatcacca tttaagggga tggcattctt tatacctaaa 4501 cacctaagag ctgaagtcag gtcttttaat caggttagaa ttctaaatga tgccagagaa 4561 ggcttgggaa attgtacttc agcgtgatag cctgtgtctt cttaatttgc tgcaaaatat 4621 gtggtagaga aagaaaagga aacagaaaaa tcactctggg ttatatagca agagatgaag 4681 gagaatattt caacacaggg ttttttgtgtt gacataggaa aagcctgatt cttggcaact 4741 gttgtagttt gtctttcagg ggtgaaggtc ccactgacaa cccctgttgt ggtgttccac 4801 acgctgtttg ttggggtagc ttccatcggc agtctggccc attgtcagtc atgcttcttc 4861 tggccgggga gattatagag agattgtttg aagattgggt tattattgaa agtctttttt 4921 tttgtttgtt ttgttttggt ttgtttgttt atctacactt gtttatgctg tgagccaaac 4981 ctctatttaa aaagttgata ctcactttca atattttatt tcatattatt atatatgtca 5041 tgatagttat cttgatgtaa atatgaagat ttttttgttt ctgtagatag taaactcttt 5101 ttttaaaaaa ggaaaaggga aacatttta taaagttata ttttaatcac cattttata 5161 cattgtagtt ctctccaagc ccagtaagag aatgatgatt catttgcatg gaggtcgatg 5221 gacaaccaat catctacctt ttctaattta aatgataatc tgatatagtt ttattgccag
```

```
-continued
5281  ttaaatgagg atgctgcaaa gcatgttttt tcactagtaa cttttgctaa ctgaatgaat
5341  tctgggtcca tatctcccag atgaaaaact gttaaccaat accatatttt atagttggtg
5401  tccatttctt tccaacactg tttgttatga ttcttccttg agtacttata tacagacctg
5461  ctcattatct aaacaatctt accttctaag taaaccttga ttgtgatttc cagttttat
5521  tttctctgac gtagtagaaa ggaatgttta cattaaaaat acttttgttt ctcataaatg
5581  gatattgtac tcccccttt caaagcatta ttttacaata attcatggca tttaaaaaa
5641  taaggcaaag ataatacgac aaaaaatata catggtttca aggcaaattc tccaataagt
5701  tggaaaatgt aaaaaggatc aagtggatgc agcctctacc taaataatta aaatatattt
5761  cagtatattt ctgaattaac accaggtctt cattatttag aacttactaa attgttttca
5821  ttttcttagt tttacctgtg tatctccatg tttgcaaaaa ttactataag tcaaattttg
5881  ccagtgaatt taactatttt tctttccttg caattaaggg gaaaaaagca tttatcttat
5941  cttctcatac cccttgcatc taagtactta gcaaagtcaa tattttccca ttttccaaat
6001  gcgtccatct ctaacataaa tattaattga acatagagct atgtttggag tgagtggact
6061  ggcaggacag ttggaagtcc atcacagtct attgacagtt tcatcaaagc tgtatagtcc
6121  aactagtggg gcagcttggc tactatggtg gaagtctcag caaactgcct ggttttgttt
6181  gtttgttttg ttttaaggta caggaaataa gaggaataat agtggccaaa gcaattagaa
6241  catcttcatt ccagaactgt gttcagcaat ccaggcagat tgatacattt ttctttaaaa
6301  ataaattgct attacagcta gacgtcaatt gggataaata aagggatgaa gatccactaa
6361  gtttgtgact ttcatacaca cccagtacat ctcaaaggat gctaagggac atttctgcc
6421  agtagagttc tcccccttt tggtgacagc aatattatta tgttcacatc taactccaga
6481  gcttacttcc tgtggtgcca atgtatttgt tgcaatttac tacattttta tatgagccta
6541  tttataggtg ccattaaact caggtctttc aaatgaaaga gtttctagcc cacttaggga
6601  aaaagataat tgtttagaaa accataaaat caatggtagg aaaagttgga actggttacc
6661  tggatgccat ggttctctgt taaataaagt aagagaccag gtgtattctg agtgtcatca
6721  gtgttatttt cagcatgcta ataaatgtct ttccggttat atatctatct aaattaacct
6781  ttaaaatatt ggtttccttg ataaaagcac cacttttgct tttgttagct gtaatatttt
6841  ttgtcattta gataagacct ggtttggctc tcaataaaag atgaagacag tagctctgta
6901  cagggatata tctatattag tcttcatctg atgaatgaag aaattttctc atattatgtt
6961  caagaaagta tttacttcct aaaaatagaa ttcccgattc tgtctatttt ggttgaatac
7021  cagaacaaat cttttcgttg caatcccagt aaaacgaaag aaaaggaata tcttacagac
7081  tgttcatatt agatgtatgt agactgttaa tttgcaattt ccccatattt cctgcctatc
7141  ttacccagat aactttcttt gaaggtaaaa gctgtgcaaa aggcatgaga ctcaggccta
7201  ctctttgttt aaatgatgga aaaatataaa ttattttcta agtaataaaa gtataaaaat
7261  tatcattata aataaagtct aaagtttgaa attattaatt taaaaaaaaa aaaaaaaa
```

By "PDE3A polypeptide" is meant a protein or fragment thereof having at least 85% amino acid sequence identity to the sequence provided at NCBI Ref No. NP_000912.3 that catalyzes the hydrolysis of cyclic adenosine monophosphate (cAMP) and cyclic guanosine monophosphate (cGMP). An exemplary human full-length PDE3A amino acid sequence is:

(SEQ ID NO: 2)
MAVPGDAARVRDKPVHSGVSQAPTAGRDCHHRADPASPRDSGCRGCWGDLV

LQPLRSSRKLSSALCAGSLSFLLALLVRLVRGEVGCDLEQCKEAAAAEEEE

AAPGAEGGVFPGPRGGAPGGGARLSPWLQPSALLFSLLCAFFWMGLYLLRA

GVRLPLAVALLAACCGGEALVQIGLGVGEDHLLSLPAAGVVLSCLAAATWL

-continued

VLRLRLGVLMIALTSAVRTVSLISLERFKVAWRPYLAYLAGVLGILLARYV
EQILPQSAEAAPREHLGSQLIAGTKEDIPVFKRRRRSSSVVSAEMSGCSSK
SHRRTSLPCIPREQLMGHSEWDHKRGPRGSQSSGTSITVDIAVMGEAHGLI
TDLLADPSLPPNVCTSLRAVSNLLSTQLTFQAIHKPRVNPVTSLSENYTCS
DSEESSEKDKLAIPKRLRRSLPPGLLRRVSSTWTTTTSATGLPTLEPAPVR
RDRSTSIKLQEAPSSSPDSWNNPVMMTLTKSRSFTSSYAISAANHVKAKKQ
SRPGALAKISPLSSPCSSPLQGTPASSLVSKISAVQFPESADTTAKQSLGS
HRALTYTQSAPDLSPQILTPPVICSSCGRPYSQGNPADEPLERSGVATRTP
SRTDDTAQVTSDYETNNNSDSSDIVQNEDETECLREPLRKASACSTYAPET
MMFLDKPILAPEPLVMDNLDSIMEQLNTWNFPIFDLVENIGRKCGRILSQV
SYRLFEDMGLFEAFKIPIREFMNYFHALEIGYRDIPYHNRIHATDVLHAVW
YLTTQPIPGLSTVINDHGSTSDSDSDSGFTHGHMGYVFSKTYNVTDDKYGC
LSGNIPALELMALYVAAAMHDYDHPGRTNAFLVATSAPQAVLYNDRSVLEN
HHAAAAWNLFMSRPEYNFLINLDHVEFKHFRFLVIEAILATDLKKHFDFVA
KFNGKVNDDVGIDWTNENDRLLVCQMCIKLADINGPAKCKELHLQWTDGIV
NEFYEQGDEEASLGLPISPFMDRSAPQLANLQESFISHIVGPLCNSYD SA
GLMPGKWVEDSDESGDTDDPEEEEEEAPAPNEEETCENNESPKKKTFKRRK
IYCQITQHLLQNHKMWKKVIEEEQRLAGIENQSLDQTPQSHSSEQIQAIKE
EEEEKGKPRGEEIPTQKPDQ

Several PDE3A isoforms are known including PDE3A1, PDE3A2, and PDE3A3. PDE3A1 comprises amino acids 146-1141, PDE3A2 isoform 2 comprises amino acids 299-1141, and PDE3A3 comprises amino acids 483-1141 of the full-length PDE3A amino acid sequence. Additionally, spliced transcript variants encoding multiple isoforms have been observed for PDE3A. One such transcript variant has NCBI Ref No. NM_001244683 which has an associated protein sequence (NP_001231612.1):

(SEQ ID NO: 3)
MVTIFSKSWSFYWEKSSGTSITVDIAVMGEAHGLITDLLADPSLPPNVCTS
LRAVSNLLSTQLTFQAIHKPRVNPVTSLSENYTCSDSEESSEKDKLAIPKR
LRRSLPPGLLRRVSSTWTTTTSATGLPTLEPAPVRRDRSTSIKLQEAPSSS
PDSWNNPVMMTLTKSRSFTSSYAISAANHVKAKKQSRPGALAKISPLSSPC
SSPLQGTPASSLVSKISAVQFPESADTTAKQSLGSHRALTYTQSAPDLSPQ
ILTPPVICSSCGRPYSQGNPADEPLERSGVATRTPSRTDDTAQVTSDYETN
NNSDSSDIVQNEDETECLREPLRKASACSTYAPETMMFLDKPILAPEPLVM
DNLDSIMEQLNTWNFPIFDLVENIGRKCGRILSQVSYRLFEDMGLFEAFKI
PIREFMNYFHALEIGYRDIPYHNRIHATDVLHAVWYLTTQPIPGLSTVIND
HGSTSDSDSDSGFTHGHMGYVFSKTYNVTDDKYGCLSGNIPALELMALYVA
AAMHDYDHPGRTNAFLVATSAPQAVLYNDRSVLENHHAAAAWNLEMSRPEY
NFLINLDHVEFKHERFLVIEAILATDLKKHEDFVAKENGKVNDDVGIDWTN
ENDRLLVCQMCIKLADINGPAKCKELHLQWTDGIVNEFYEQGDEEASLGLP
ISPFMDRSAPQLANLQESFISHIVGPLCNSYDSAGLMPGKWVEDSDESGDT
DDPEEEEEEAPAPNEEETCENNESPKKKTFKRRKIYCQITQHLLQNHKMWK
KVIEEEQRLAGIENQSLDQTPQSHSSEQIQAIKEEEEEKGKPRGEEIPTQK
PDQ.

In some embodiments, the expression of isoforms of PDE3A in the cell may be measured.

By "PDE3B polynucleotide" is meant any nucleic acid molecule encoding a PDE3B polypeptide or fragment thereof. An exemplary PDE3B nucleic acid sequence is provided at NCBI Ref: NM_000922.3:

(SEQ ID NO: 4)
```
  1 gctcgcgcgc ccaacggacc aggctggggc cgtgaggtaa ctgttgcagc cagcggaggt
 61 gggaggcgac actgagtctc cagtcccgag aggtgcccga gggaaaagga ggcggcagct
121 aaactggtcc tggagagaag ccccttccgc ccctctcctc agccagcatg tcccggactc
181 cgccgctcct cagtccgcgc ggtggggacc ccgggccgtg gcggccggcg cagccctgac
241 gggttgcgaa ccagggggcg ccccgaacgc ggggggttggg gtctgggagc gcgagcggcc
301 gctacggtac gagcggggtg tgctgagtcc cgtggccacc cccggcccca gccatgagga
361 gggacgagcg agacgccaaa gccatgcggt ccctgcagcc gccggatggg gccggctcgc
421 cccccgagag tctgaggaac ggctacgtga agagctgcgt gagcccttg cggcaggacc
481 ctccgcgcgg cttcttcttc cacctctgcc gcttctgcaa cgtggagctg cggccgccgc
541 cggcctctcc ccagcagccg cggcgctgct ccccccttctg ccgggcgcgc ctctcgctgg
601 gcgccctggc tgcctttgtc ctcgccctgc tgctgggcgc ggaacccgag agctgggctg
661 ccggggccgc ctggctgcgg acgctgctga gcgtgtgttc gcacagcttg agccccctct
721 tcagcatcgc ctgtgccttc ttcttcctca cctgcttcct cacccggacc aagcggggac
781 ccggcccggg ccggagctgc ggctcctggt ggctgctggc gctgccgcc tgctgttacc
841 tgggggactt cttggtgtgg cagtggtggt cttggccttg gggggatggc gacgcaggt
```

-continued

```
 901 ccgcggcccc gcacacgccc ccggaggcgg cagcgggcag gttgctgctg gtgctgagct
 961 gcgtagggct gctgctgacg ctcgcgcacc cgctgcggct ccggcactgc gttctggtgc
1021 tgctcctggc cagcttcgtc tggtgggtct ccttcaccag cctcgggtcg ctgccctccg
1081 ccctcaggcc gctgctctcc ggcctggtgg ggggcgctgg ctgcctgctg gccctggggt
1141 tggatcactt ctttcaaatc agggaagcgc ctcttcatcc tcgactgtcc agtgccgccg
1201 aagaaaagt gcctgtgatc cgaccccgga ggaggtccag ctgcgtgtcg ttaggagaaa
1261 ctgcagccag ttactatggc agttgcaaaa tattcaggag accgtcgttg ccttgtattt
1321 ccagagaaca gatgattctt tgggattggg acttaaaaca atggtataag cctcattatc
1381 aaaattctgg aggtggaaat ggagttgatc tttcagtgct aaatgaggct cgcaatatgg
1441 tgtcagatct tctgactgat ccaagccttc caccacaagt catttcctct ctacggagta
1501 ttagtagctt aatgggtgct ttctcaggtt cctgtaggcc aaagattaat cctctcacac
1561 catttcctgg attttacccc tgttctgaaa tagaggaccc agctgagaaa ggggatagaa
1621 aacttaacaa gggactaaat aggaatagtt tgccaactcc acagctgagg agaagctcag
1681 gaacttcagg attgctacct gttgaacagt cttcaaggtg ggatcgtaat aatggcaaaa
1741 gacctcacca agaatttggc atttcaagtc aaggatgcta tctaaatggg ccttttaatt
1801 caaatctact gactatcccg aagcaaaggt catcttctgt atcactgact caccatgtag
1861 gtctcagaag agctggtgtt ttgtccagtc tgagtcctgt gaattcttcc aaccatggac
1921 cagtgtctac tggctctcta actaatcgat cacccataga atttcctgat actgctgatt
1981 ttcttaataa gccaagcgtt atcttgcaga gatctctggg caatgcacct aatactccag
2041 attttttatca gcaacttaga aattctgata gcaatctgtg taacagctgt ggacatcaaa
2101 tgctgaaata tgtttcaaca tctgaatcag atggtacaga ttgctgcagt ggaaaatcag
2161 gtgaagaaga aaacattttc tcgaaagaat cattcaaact tatggaaact caacaagaag
2221 aggaaacaga gaagaaagac agcagaaaat tatttcagga aggtgataag tggctaacag
2281 aagaggcaca gagtgaacag caaacaaata ttgaacagga agtatcactg gacctgattt
2341 tagtagaaga gtatgactca ttaatagaaa agatgagcaa ctggaatttt ccaattttg
2401 aacttgtaga aaagatggga gagaaatcag gaaggattct cagtcaggtt atgtatacct
2461 tatttcaaga cactggttta ttggaaatat ttaaaattcc cactcaacaa tttatgaact
2521 attttcgtgc attagaaaat ggctatcgag acattcctta tcacaatcgt atacatgcca
2581 cagatgtgct acatgcagtt tggtatctga caacacggcc agttcctggc ttacagcaga
2641 tccacaatgg ttgtggaaca ggaaatgaaa cagattctga tggtagaatt aaccatgggc
2701 gaattgctta tatttcttcg aagagctgct ctaatcctga tgagagttat ggctgcctgt
2761 cttcaaacat tcctgcatta gaattgatgg ctctatacgt ggcagctgcc atgcatgatt
2821 atgatcaccc agggaggaca aatgcatttc tagtggctac aaatgcccct caggcagttt
2881 tatacaatga cagatctgtt ctggaaaatc atcatgctgc gtcagcttgg aatctatatc
2941 tttctcgccc agaatacaac ttccttcttc atcttgatca tgtggaattc aagcgctttc
3001 gttttttagt cattgaagca atccttgcta cggatcttaa aaagcatttt gattttctcg
3061 cagaattcaa tgccaaggca aatgatgtaa atagtaatgg catagaatgg agtaatgaaa
3121 atgatcgcct cttggtatgc caggtgtgca tcaaactggc agatataaat ggcccagcaa
3181 aagttcgaga cttgcatttg aaatggacag aaggcattgt caatgaattt tatgagcagg
3241 gagatgaaga agcaaatctt ggtctgccca tcagtccatt catggatcgt tcttctcctc
3301 aactagcaaa actccaagaa tcttttatca cccacatagt gggtcccctg tgtaactcct
```

-continued

```
3361 atgatgctgc tggtttgcta ccaggtcagt ggttagaagc agaagaggat aatgatactg
3421 aaagtggtga tgatgaagac ggtgaagaat tagatacaga agatgaagaa atggaaaaca
3481 atctaaatcc aaaaccacca agaaggaaaa gcagacggcg aatattttgt cagctaatgc
3541 accacctcac tgaaaaccac aagatatgga aggaaatcgt agaggaagaa gaaaaatgta
3601 aagctgatgg gaataaactg caggtggaga attcctcctt acctcaagca gatgagattc
3661 aggtaattga gaggcagat gaagaggaat agcgacagtt tgagtaaaag aaaagtcata
3721 ttgaagaagc ccagagggtt gtgcccaggg gcagaaatca ttgcctagtg ttcaccggct
3781 gactctcaac tgaccattcc catgtggaca ggccttaata ctgtgagagg atccttgctc
3841 tgctggcagt ttcccactcc tatgcacttt cacaggaact agaaaactat tcttaaacca
3901 aaaataccat ccgtgttgac ccatgttgca gagcccttac ttaaatcctt cactggtgta
3961 tgaatacttt gtcataatgc tgctttgctg ggtagtgagc tcttattttt cactgggggt
4021 cagctataac taaaaactca agtgacatat ttcagttacc aaagtggcca ggaacttttt
4081 gcttttatga aaatagattc atattgtatt tcccagtgtg tcttttatgt ctttgaatgt
4141 tttggagaaa agtctatgcc tgtctaaaaa tgaatccagt gttgcctttc tgagggattt
4201 ctgctcaatg caatacactg ttcagtgcta ttctcccagc taggtttatc catgaaggac
4261 tgagtgacct tgttgtatt taacaaaatc caggtgcatc aatttctgat gcttttact
4321 attgtgtatt atctactatg tgtgttttat ttctgctgag agtattcagg tttgccatgg
4381 acatcagaag tttgaattcc agtcttatct tatgttccat ggctgaattt taaagctgtt
4441 taggtttaac aatgaaggga tttattcttt agtcaaaatt gttgttttta ctctagctca
4501 ggattcgtat tttaaagat ttagttaata tgaacacagc acagatttgt tagaagaaaa
4561 aaaatttgct gtaataccaa aactaacctc atcaaagata cagaaaaaaa gaaatatagt
4621 gagccctaaa ggacacatac attgaataaa taattggaac atgtggttat ctttagatcc
4681 acatcttagc tgtcatttgt tcactctaaa actgatgttc atctttctgt taatttccct
4741 ctgcctaaag actacatgac agaaatgacc tatcactact tattatttct gaagcctaac
4801 tgcaagactg atttctgaga acaagtaaag aactggaata cttattttc atataaaaat
4861 ctaaatgtgt taataaatca tttcatacaa aagtacatta ttaaataacc acattattaa
4921 aataattgca agaaaatgga ccatatttac aatgttttgt aaacttgcta gtgtgtggat
4981 atgtaccta cttgtgaaat acatttgaag atataaagag cagccaaaat gatggcaaaa
5041 tggtaggcta atattttcta ttattattgg agaacatatc atattttgga atcatgcaat
5101 tttgcacaca gtgaaaccat taattttcca aggtaattcc tttagaatat ggtattggca
5161 tgcagtttct tacttatcta gaatatttgg cttatctgaa agatatcaat ttaagatctc
5221 tggaagtgtt agaattttttg atccttcaca gtgtcaatat ttaatgaatc actaagcttt
5281 atttattaga cgtgttgagt gagtgctgag ttccttgctg ccacttttgt taccattgtc
5341 acacactatg tgtaaaccag tcccaccact tattactaat aaaattttga ctgataattt
5401 atatttgcac ttacaatata tatatcctgt cctatattt ctctagagta catttttccat
5461 catgtttaag tgtatttctg ctattatttc ctctcctgca gaatacatac aagtgtatgt
5521 gtataaagtc atacatgtac aagcatgcat attgagattg aatcacattt ccatactgtc
5581 tgttatttta ttgggtttta tattgggttt ctttagttta tgttgttttc tcaaaagcag
5641 cattttaaat tacgaatact ggacttattg gatttaatta taaatccaat tactactgga
5701 aactcatttt tacataatat agtccttaaa ttatttaacc cttgctaagt aattgacata
```

```
5761 tgtaacaata actagcctaa agaaacccaa aaaagtatct ctcccgagct gaaacttaaa 5821 aattcgtaag tgtaagaaag aatgtgagaa tatattaaat gcacactgta ccattagatg 5881 aaatcttact tgagaaattg ccataagcca tattacagat cttactttgt tactgaatca 5941 gattaatttc ttgttataat aattttcatc ataaattttc tattttttaaa gccgctggta 6001 ctagaaatat tcttttaatg ctatatctat gtacctactg acacattttt ctccataaaa 6061 gtacttttaa aaattacttc atgatttgaa a
```

By "PDE3B polypeptide" is meant a protein or fragment thereof having at least 85% amino acid sequence identity to the sequence provided at NCBI Ref No. NP_000913.2. An exemplary human full-length PDE3A amino acid sequence is:

(SEQ ID NO: 5)
MRRDERDAKAMRSLQPPDGAGSPPESLRNGYVKSCVSPLRQDPPRGFFFHL

CRFCNVELRPPPASPQQPRRCSPFCRARLSLGALAAFVLALLLGAEPESWA

AGAAWLRTLLSVCSHSLSPLFSIACAFFFLTCFLTRTKRGPGPGRSCGSWW

LLALPACCYLGDFLVWQWWSWPWGDGDAGSAAPHTPPEAAAGRLLLVLSCV

GLLLTLAHPLRLRHCVLVLLLASFVWWVSFTSLGSLPSALRPLLSGLVGGA

GCLLALGLDHFFQIREAPLHPRLSSAAEEKVPVIRPRRRSSCVSLGETAAS

YYGSCKIFRRPSLPCISREQMILWDWDLKQWYKPHYQNSGGGNGVDLSVLN

EARNMVSDLLTDPSLPPQVISSLRSISSLMGAFSGSCRPKINPLTPFPGFY

PCSEIEDPAEKGDRKLNKGLNRNSLPTPQLRRSSGTSGLLPVEQSSRWDRN

NGKRPHQEFGISSQGCYLNGPFNSNLLTIPKQRSSSVSLTHHVGLRRAGVL

SSLSPVNSSNHGPVSTGSLTNRSPIEFPDTADFLNKPSVILQRSLGNAPNT

PDFYQQLRNSDSNLCNSCGHQMLKYVSTSESDGTDCCSGKSGEEENIFSKE

SFKLMETQQEEETEKKDSRKLFQEGDKWLTEEAQSEQQTNIEQEVSLDLIL

VEEYDSLIEKMSNWNFPIFELVEKMGEKSGRILSQVMYTLFQDTGLLEIFK

IPTQQFMNYFRALENGYRDIPYHNRIHATDVLHAVWYLTTRPVPGLQQIHN

GCGTGNETDSDGRINHGRIAYISSKSCSNPDESYGCLSSNIPALELMALYV

AAAMHDYDHPGRTNAFLVATNAPQAVLYNDRSVLENHHAASAWNLYLSRPE

YNFLLHLDHVEFKRFRFLVIEAILATDLKKHFDFLAEFNAKANDVNSNGIE

WSNENDRLLVCQVCIKLADINGPAKVRDLHLKWTEGIVNEFYEQGDEEANL

GLPISPFMDRSSPQLAKLQESFITHIVGPLCNSYDAAGLLPGQWLEAEEDN

DTESGDDEDGEELDTEDEEMENNLNPKPPRRKSRRRIFCQLMHHLTENHKI

WKEIVEEEEKCKADGNKLQVENSSLPQADEIQVIEEADEEE

By "SLFN12 polynucleotide" is meant any nucleic acid molecule encoding a SLFN12 polypeptide or fragment thereof. An exemplary SLFN12 nucleic acid sequence is provided at NCBI Ref: NM_018042.4:

```
                                              (SEQ ID NO: 6)
  1 tttgtaactt cacttcagcc tcccattgat cgctttctgc aaccattcag actgatctcg 61 ggctcctatt tcatttacat tgtgtgcaca ccaagtaacc agtgggaaaa ctttagaggg 121 tacttaaacc ccagaaaatt ctgaaaccgg gctcttgagc cgctatcctc gggcctgctc 181 ccaccctgtg gagtgcactt tcgttttcaa taaatctctg cttttgttgc ttcattcttt 241 ccttgctttg tttgtgtgtt tgtccagttc tttgttcaac acgccaagaa cctggacact 301 cttcactggt aacatatttt ggcaagccaa ccaggagaaa agaatttctg cttggacact 361 gcatagctgc tgggaaaatg aacatcagtg ttgatttgga acgaattat gccgagttgg 421 ttctagatgt gggaagagtc actcttggag agaacagtag gaaaaaatg aaggattgta 481 aactgagaaa aaagcagaat gaaagtgtct cacgagctat gtgtgctctg ctcaattctg 541 gaggggagt gatcaaggct gaaattgaga atgaagacta tagttataca aaagatggaa 601 taggactaga tttggaaaat tcttttagta acattctgtt atttgttcct gagtacttag 661 acttcatgca gaatggtaac tactttctga ttttttgtgaa gtcatggagc ttgaacacct 721 ctggtctgcg gattaccacc ttgagctcca atttgtacaa aagagatata acatctgcaa 781 aagtcatgaa tgccactgct gcactggagt tcctcaaaga catgaaaaag actagaggga 841 gattgtattt aagaccagaa ttgctggcaa agaggccctg tgttgatata caagaagaaa 901 ataacatgaa ggccttggcc ggggtttttt ttgatagaac agaacttgat cggaaagaaa 961 aattgacctt tactgaatcc acacatgttg aaattaaaaa cttctcgaca gaaaagttgt
```

```
1021 tacaacgaat taaagagatt ctccctcaat atgtttctgc atttgcaaat actgatggag 1081 gatatttgtt cattggttta aatgaagata agaaataat tggctttaaa gcagagatga 1141 gtgacctcga tgacttagaa agagaaatcg aaaagtccat taggaagatg cctgtgcatc 1201 acttctgtat ggagaagaag aagataaatt attcatgcaa attccttgga gtatatgata 1261 aaggaagtct ttgtggatat gtctgtgcac tcagagtgga gcgcttctgc tgtgcagtgt 1321 ttgctaaaga gcctgattcc tggcatgtga agataaccg tgtgatgcag ttgaccagga 1381 aggaatggat ccagttcatg gtggaggctg aaccaaaatt ttccagttca tatgaagagg 1441 tgatctctca aataaatacg tcattacctg ctccccacag ttggcctctt ttggaatggc 1501 aacggcagag acatcactgt ccagggctat caggaaggat aacgtatact ccagaaaacc 1561 tttgcagaaa actgttctta caacatgaag gacttaagca attaatatgt gaagaaatgg 1621 actctgtcag aaagggctca ctgatcttct ctaggagctg gtctgtggat ctgggcttgc 1681 aagagaacca caaagtcctc tgtgatgctc ttctgatttc ccaggacagt cctccagtcc 1741 tatacacctt ccacatggta caggatgagg agtttaaagg ctattctaca caaactgccc 1801 taaccttaaa gcagaagctg gcaaaaattg gtggttacac taaaaagtg tgtgtcatga 1861 caaagatctt ctacttgagc cctgaaggca tgacaagctg ccagtatgat ttaaggtcgc 1921 aagtaattta ccctgaatcc tactatttta caagaaggaa atacttgctg aaagcccttt 1981 ttaaagcctt aaagagactc aagtctctga gagaccagtt ttcctttgca gaaaatctat 2041 accagataat cggtatagat tgctttcaga agaatgataa aaagatgttt aaatcttgtc 2101 gaaggctcac ctgatggaaa atggactggg ctactgagat attttcatt atatatttga 2161 taacattctc taattctgtg aaaatatttc tttgaaaact ttgcaagtta agcaacttaa 2221 tgtgatgttg gataattggg ttttgtctat tttcacttct ccctaaataa tcttcacaga 2281 tattgtttga gggatattag gaaaattaat ttgttaactc gtctgtgcac agtattattt 2341 actctgtctg tagttcctga ataaattttc ttccatgctt gaactgggaa aattgcaaca 2401 cttttattct taatgacaac agtgaaaatc tcccagcata tacctagaaa acaattataa 2461 cttacaaaag attatccttg atgaaactca gaatttccac agtgggaatg aataagaagg 2521 caaaactcat
```

By "SLFN12 polypeptide" is meant a protein or fragment thereof having at least 85% amino acid sequence identity to the sequence provided at NCBI Ref No. NP_060512.3 that interacts with PDE3A when bound to DNMDP and other complex inducing compounds. An exemplary human SLFN12 amino acid sequence is:

(SEQ ID NO: 7)
MNISVDLETNYAELVLDVGRVTLGENSRKKMKDCKLRKKQNESVSRAMCAL

LNSGGGVIKAEIENEDYSYTKDGIGLDLENSFSNILLFVPEYLDFMQNGNY

FLIFVKSWSLNTSGLRITTLSSNLYKRDITSAKVMNATAALEFLKDMKKTR

GRLYLRPELLAKRPCVDIQEENNMKALAGVFFDRTELDRKEKLTFTESTHV

EIKNFSTEKLLQRIKEILPQYVSAFANTDGGYLFIGLNEDKEIIGFKAEMS

DLDDLEREIEKSIRKMPVHHFCMEKKKINYSCKFLGVYDKGSLCGYVCALR

VERFCCAVFAKEPDSWHVKDNRVMQLTRKEWIQFMVEAEPKFSSSYEEVIS

QINTSLPAPHSWPLLEWQRQRHHCPGLSGRITYTPENLCRKLFLQHEGLKQ

LICEEMDSVRKGSLIFSRSWSVDLGLQENHKVLCDALLISQDSPPVLYTFH

MVQDEEFKGYSTQTALTLKQKLAKIGGYTKKVCVMTKIFYLSPEGMTSCQY

DLRSQVIYPESYYFTRRKYLLKALFKALKRLKSLRDQFSFAENLYQIIGID

CFQKNDKKMFKSCRRLT.

By "AIP polynucleotide" is meant any nucleic acid molecule encoding an AIP polypeptide or fragment thereof. An exemplary AIP nucleic acid sequence is provided at NCBI Ref: NM_003977.2:

(SEQ ID NO: 8)
```
1 ttttggcttc tgccctcaac caaaatggcg ctagctcgga agctgccgag gtgctaggag 61 ttgccgaagc aagtccggaa gctaccgagc gagtccggaa gttgccgaaa gggagcagcg
```

-continued

```
 121 gggaaggagg atggcggata tcatcgcaag actccgggag gacgggatcc aaaaacgtgt
 181 gatacaggaa ggccgaggag agctcccgga ctttcaagat gggaccaagg ttcgtgtcta
 241 ccctacccett ctcccctct gcggcgtggt gcgcatgcga ggcgggagga ggccttaggc
 301 gagaggttgc gcatgcccag agggcagcgt ccactgcccc taccgctcac atgcagaact
 361 cgacgctgat tgggctgaat ttaagtaggg ggtgaattcg ggcctgtctg ccccgccccc
 421 tggctcggcc ttgtagcagc attggtgggg gaggccgtca gtcatcacaa gcgggttggg
 481 gttgggggtt gatctcagtg cttgggcaga ccccacgctg gaggaaaccc agggccggga
 541 gtggtcctcg ggtatctggg tttcaaggct catgatcctt tgtagatgga agggccttct
 601 gaaaacactt agaccaactg ccgctgttta gagtggaaaa ccaagaccct gggacgtgca
 661 aagccggaga cgggcccag aggtcaggtc tcccagacag ggactcttta gcagccttcc
 721 tgctgcacta ggggcttgtt gggacagatg agggttggga agtaaagaac ctcccacttt
 781 tctccttttt gccaggcccc cagatccagc ccctctgccc gcttctcccc caacctacaa
 841 ctccaggctt ccctgcttct cctgtagttg cctcctcccg gagtgctttt cccagctgcc
 901 acttgtttgc agagtaggga acctcccagg ggcagcccct gtgcccagca gagcagtcag
 961 gcaggacatg cacattgagc aaatgagcac atgcccctg ccagcaccg tgccgaatcg
1021 ggcagctaag catcctagcc cagtgcagta taagtgccct gagagcagag gggagctgca
1081 tggctggagt gatccgctgt atgaaaagat atcttctcta agaagagaca ggatgtgtgg
1141 tgtgggttca tgccccatg tgctgggggg ttggtggcgt tggaagaagg ggctggcaag
1201 ggggatcctg gatggaacag acatcagaag gagagatgtg aacaatggca ccccaagatc
1261 agaaacaggt ggtgttaaat aaccaatcgc cagcactgat tgagtgctca ctattcgaac
1321 attgtgctac atgcttcaca cgtttatttc ctacaatgtg agataggtac tgttgttgat
1381 tccgttttac cgatgtggaa actgacttca gagatgcagc atggtgcggc agttaagagc
1441 gtgggctcct ctaaccatat cctgtcgaga gttcaatctc caaacctctt ttctctgcac
1501 ccaccccag tgttatctct aaaaactctc cctgcccgga ttactcccag atgcagctct
1561 ccagtcatta actgtctctt aaacctgata tatagctccc tactcaccat atccacctgg
1621 aagcctggtt ggcaactcac acttaacctg ctccacctga ggcttctccg tgtcagggga
1681 accaacaacc ttcccgttgt tcagggcaaa aaccttagca tctctgtggt cctcccagtc
1741 tcacatccaa catcacatcc tcaatatcca gccaggatct gagttctcac cacttctgcc
1801 atcactgctt gggtccaggc catcctcatc tccagcctgg gttactgcag cgacctctaa
1861 ctctcctgcc tcttttgtcc ctctgtggtc tgttctcgtc ccagcagccg agcccatgcc
1921 agattcaatt ccttttttgc tcggagccac tcagtggctt ccatcacaga gtgaaaaaca
1981 gaggcctcac catagcctac aggccctgtg aggtccaccc ctactgacct gggtgagctc
2041 ccctgctgac cctgtggtgt accccacccc ctccttcact ctgctctgcc acactggcat
2101 tgctgctctt gaacacatca tgcatttgaa acgggaagtt cccttgtctc cctcgcaggg
2161 cgtgcgatgg gggagtggct cgcttcttca gtgccccgct gctcagacct ctggggagc
2221 atacagatgg gcaggctgtg ggctccgacc tcatggcagt gtctagggt gaatatttac
2281 agctccgtgt gttctagggt gctcttttag tttgtctatg ggaggcttgt gttaaccagc
2341 tcaattagac ccccttcctt atcacaagga cagagggctt tctgtagtct ggggttttct
2401 tgccttgatg tactggagta ctggagaatt agatcacttg tgggcttgga gaatgattgc
2461 aaattttttt ttattttta ttttattttt ttttctgag atggagtttc actcttgttg
2521 cccaggctgg agtgcaatgg cacaatctct gcctcccagg ttcaagcaat tctcctgcct
```

-continued

```
2581 cagcctccca agtagctgag attacatgtg cctgacacca ggcccggcta attttaaaa
2641 atgttttag tagagatggg cttttaccat gttggccaag ctggtttcaa acgccttttt
2701 ttttttttt tttttgaga cggagtcttg ctctattgcc caagctggag tgcagtggca
2761 tgatctcggt tcactgcaac ctccaccttc tgggttcaag tgattctcct gcctcagcct
2821 cccaagtagc tgggattaca ggcacccgcc atcatggcca gctaatttt gtattttag
2881 tagagacggg gttttgccac attggccagg ctggtcttga actcctgacc tcaggtgatc
2941 cacccgcctt ggagatggtc ttcccctggg gttgggccac ttggtggccc cacctctcct
3001 ctgactgccc cagccaaact ccgcctcttc ctgccagttg atgacctgcc agcgtgcagg
3061 tgcctgtcag tgtgatcttc tgcttcttgc tcccctgaca tcctctcaat gaccaggagc
3121 tcgtcttctg ctgatgggct cctctgacat ctggctgcct gtgggtctac ccctaggg
3181 tgttgggttt ttataggcac aggataggg tgtggcaggc cagggtggtc ttgggaaatg
3241 caacatttgg gcaggaaatg cctgttctca cctaggtctg tgggggtgga acccacccca
3301 gggaccacgc cctcctctac ccagcacttc ccttctcccc ttccaaatta tttaacagga
3361 ccatgctcct cccttcccag cacttccata tcacattgtc ccactgcaag cttttttac
3421 acatgctgtt cttttggcct agaaagttcc tatcccaggg tccacttggc ttgctttctt
3481 ccttactccc caaccccca ctctgtttaa tccagcccca accctcttgc cctgctgttt
3541 cccaagcacg tggcttcacc tgccatgaca tattgttttg tttgatgccc atctcctccc
3601 tctagaagcg ccatgtgagc tccagggggg cagggacttt tttgtgtttt gcttgctgcc
3661 atgttctggt gtctagcaca gagcttgggc acatagtagg tgcttagtaa atatctgttg
3721 aggaatgact ggagtcagac tgcttggact cttgttccca ctcagccacc cactagccgt
3781 gtggcttggg cctattcctc ccctccttgt ggctttgttt tctcaccagc gtgggaggat
3841 gaagccaggt gtaaggtcag gtggtgtccc cggggaagcc ccgtccctta tgccgtctgc
3901 aggccgggga ctgacttct ccttgggggt cagggtgagg gtttgtgcct ttgcctgacc
3961 tcgcatgtgg cccacaggcc acgttccact accggacgct gcacagtgac gacgagggca
4021 ccgtgctgga cgacagccgg gctcgtggca agcccatgga gctcatcatt ggcaagaagt
4081 tcaagctgcc tgtgtgggag accatcgtgt gcaccatgcg agaagggag attgcccagt
4141 tcctctgtga catcaaggtg tctgtcctgt acctgtctgc ggtggctgtc cagccaagcc
4201 ctattcctat tccctatccc cagggctcct cctccctcca ccctctgcta gactgccacc
4261 cgcttttctt ttttttga gatggagtct tgctctgtcg cccaggctgg agtgcagtgg
4321 tacgatctca gctcactgca ccctccacct cctgggttca gcgattctt ctgcctcagc
4381 ctcccgagta gctgggatta caaacacccg ccatgatgcc tggctaattt ttgtattttt
4441 agtagagaca gggtttcacc atgttggcca ggctggtctt gaacacctga cctcaggtga
4501 tccacccgcc ttggcctccc aaagtgctgg gattataggc gtgtgccacc gcgcccggcc
4561 cacccactct ttccagacca ccacaccagc ctgctgatgg cgtcctggcc tccattccgc
4621 cttccctat agccagact gaggccaggg gactcgttct caaatgcaaa tgacctgtac
4681 atcccttgt ttcaaacctc tatgactcct ggtcactgta aggatagagc acagggggtc
4741 ctcacttcat gttgctgata cattcttgga aactgtgact aagagaaaaa acatacatca
4801 ggttttttct cagccaccgt catttctctc agcaaaattt tgttagaaca ttgatgagaa
4861 gaaaaattgg tttcgttatg tattgtttcg cctacagtca cagtttccaa gaacctactt
4921 aggacgttaa gtgaggactt aaaccgtata agctatagct gctcacatag ctttttgggg
```

-continued

```
4981 gctggcccct gccgtctcac cctcttactc aacctccctg cttttccttt ccattcccct 5041 tcttagccaa gatcttccct cttccttcaa agcttattcc tgggtcacca cctctaggaa 5101 gccctccctg actgctagtg gttggctcaa ctcccatgtt tgggtcctcc aaccctcatg 5161 ccctgcatgg ccaggatctg ctcttctgcc ttgtcctagg ctattgcaga gcagggatct 5221 ggcctgttta cttctagctt tgggatgccc agcgcgagcc agtccagagc caagactcag 5281 gaaatgcccg ctgatggcag cccggcagtc agccctgtc cagacaacag ggcagtggga 5341 ggagtgggga ggacccgggt aggaggaatc tggttatctg gttcccacca gcctagcagc 5401 tttgccaagc aagagattag aggctaggtc ccctatgcct gtctccctgt ggggtttttt 5461 ttttttgac taagtctcac tctgttgccc aggctggagt gcagtggcgt gatcttggct 5521 cactgcaacc accatctcct gggttcagct gattctctgc cttagctgcc tgagtagctg 5581 ggattacagg cacctgccat cgtgcccggc tcattttgt attttagcag agacgcggtt 5641 tcaccatgtt ggtcaggctg gtcttgaact cctgacctca ggtgatccgc ccgccttggc 5701 ctcccgaagt gctaggatta caggcgtgag ccaccacatc cggcctccct gagggttttg 5761 aagtggctgg cctgggccca gctctgaggt aggccctcag tggggtgtgg gtggggcaga 5821 aggaggagct gctgggaaca gaatgtgggg ggcccagtt ctttgcatag tccagcaaag 5881 ggccttatcc tctggaggga gaggaggtaa gaattctact gggcctgtaa ggaccaggga 5941 gacaggggtt gatggtaggc atgtgtctgt ggtgggggtg aggaggggt taggtgctct 6001 gtttggtggc cagagaatgt ggcagaagct ggggcttcac caggagagag ggctgagcga 6061 ctggaggagt cctgaattaa aagcctcctg tgcttaaacg gagtagggtc ccagttgtca 6121 ctctctgggc cttggtgttt gttctcagat ggtggtgggg aaggggggctg ggccttgtgg 6181 acccggtgac cagccagccc acggtgacag agccccggc gcccttgcct tcccgcagca 6241 tgtggtcctg tacccgctgg tggccaagag tctccgcaac atcgcggtgg gcaaggaccc 6301 cctggagggc cagcggcact gctgcggtgt tgcacagatg cgtgaacaca gctccctggg 6361 ccatgctgac ctggacgccc tgcagcagaa cccccagccc ctcatcttcc acatggagat 6421 gctgaaggtg aggggccacc gcgcctggtc tcaccaggcc cccactgccc agcctcaggg 6481 cggcgctggc ctgtccaccc aggggtggtg ggatccgcag gtggactgct gggggagcgg 6541 acagagacaa gaaaacctgt gcaggaccct tggcagtacc ctgggtctcc tttcctcctc 6601 cttcacatct caaatgtcac ctcctccagg aaaccggccc tgcccacccg gtctcctcat 6661 tctctgtctc gcagcagctc atttccttta tagcctctgc cgcaccttga gtcccttgg 6721 aattcatgga tttccttgtc catttaggga acctgccatg cagcatgatc tctgcgaggg 6781 cagggctttt caccgtcttg ttcactgttc tattcttagc acttggcaca gtgctgggca 6841 cacaggagat gtgacatcga tgtttgatgc ttttgagtg acaagtagct ctgctgctgg 6901 tgtgtgatgt ctgggggccc agccagccca gatgtgggtc aggtctgctg ctgacgacg 6961 cagctgtggt gtccccgagc cccgctgtga tatgccccat gccctgcagg tggagagccc 7021 tggcacgtac cagcaggacc catgggccat gacagacgaa gagaaggcaa aggcagtgcc 7081 acttatccac caggagggca accggttgta ccgcgagggg catgtgaagg aggctgctgc 7141 caagtactac gatgccattg cctgcctcaa gaacctgcag atgaaggtac tgcctggagg 7201 ctgaggggga ggatggatgg aggggggtgt ggagccaggg ggcccaggtc tacagcttct 7261 ccccgctccc tgccccata ctcccaggaa cagcctgggt ccctgaatg gatccagctg 7321 gaccagcaga tcacgccgct gctgctcaac tactgccagt gcaagctggt ggtcgaggag 7381 tactacgagg tgctggacca ctgctcttcc atcctcaaca agtacgacgg tgagcaccgg
```

```
7441 gccctgggct gccgggggct gcgagtggtc agagagtggc ctttctcctg tcactgctgg 7501 ggtcaagacc tagcctttca caaccccat tctgagctcc cacggggcc tgactaaatg 7561 cctctactcg gcagggctgt gggcccatt gtgccaatga agcatgaatg gtgtattggg 7621 ggtggggtgg catcctcagg tcaggaggg ctctctctcc cctgtgggcc catggtgcca 7681 ggagacatga gggcaggcag ctggccagga tccccctca tgcccttgca tgcccactgc 7741 ccactggcct ccctgcaga caacgtcaag gcctacttca agcggggcaa ggcccacgcg 7801 gccgtgtgga atgcccagga ggcccaggct gactttgcca aagtgctgga gctggaccca 7861 gccctggcgc ctgtggtgag ccgagagctg caggccctgg aggcacggat ccggcagaag 7921 gacgaagagg acaaagcccg gttccggggg atcttctccc attgacagga gcacttggcc 7981 ctgccttacc tgccaagccc actgctgcag ctgccagccc ccctgcccgt gctgcgtcat 8041 gcttctgtgt atataaaggc ctttatttat ctctctctga
```

By "AIP polypeptide" is meant a protein or fragment thereof having at least 85% amino acid sequence identity to the sequence provided at NCBI Reference Sequence: NP_003968.2 that can bind the aryl hydrocarbon receptor. AIP polypeptides may regulate expression of many xenobiotic metabolizing enzymes and bind specifically to and inhibit the activity of hepatitis B virus. Three transcript variants encoding different isoforms have been found for this gene. An exemplary human AIP amino acid sequence is:

(SEQ ID NO: 9)
MADIIARLREDGIQKRVIQEGRGELPDFQDGTKATFHYRTLHSDDEGTVLD

DSRARGKPMELIIGKKFKLPVWETIVCTMREGEIAQFLCDIKHVVLYPLVA

KSLRNIAVGKDPLEGQRHCCGVAQMREHSSLGHADLDALQQNPQPLIFHME

MLKVESPGTYQQDPWAMTDEEKAKAVPLIHQEGNRLYREGHVKEAAAKYYD

AIACLKNLQMKEQPGSPEWIQLDQQITPLLLNYCQCKLVVEEYYEVLDHCS

SILNKYDDNVKAYFKRGKAHAAVWNAQEAQADFAKVLELDPALAPVVSREL

QALEARIRQKDEEDKARFRGIFSH.

By "TRRAP polypeptide" is meant a protein or fragment thereof having at least 85% amino acid sequence identity to the sequence provided at NCBI Reference Sequence: NP_001231509.1 having histone acetyltransferase complex recruiting activity. An exemplary human TRRAP amino acid sequence is (which encodes the longer isoform):

(SEQ ID NO: 11)
MAFVATQGATVVDQTTLMKKYLQFVAALTDVNTPDETKLKMMQEVSENFEN

VTSSPQYSTFLEHIIPRFLTFLQDGEVQFLQEKPAQQLRKLVLEIIHRIPT

NEHLRPHTKNVLSVMFRFLETENEENVLICLRIIIELHKQFRPPITQEIHE

IFLDFVKQIYKELPKVVNRYFENPQVIPENTVPPPEMVGMITTIAVKVNPE

REDSETRTHSIIPRGSLSLKVLAELPIIVVLMYQLYKLNIHNVVAEFVPLI

MNTIAIQVSAQARQHKLYNKELYADFIAAQIKTLSFLAYIIRIYQELVTKY

SQQMVKGMLQLLSNCPAETAHLRKELLIAAKHILTTELRNQFIPCMDKLFD

ESILIGSGYTARETLRPLAYSTLADLVHHVRQHLPLSDLSLAVQLFAKNID

DESLPSSIQTMSCKLLLNLVDCIRSKSEQESGNGRDVLMRMLEVFVLKFHT

IARYQLSAIFKKCKPQSELGAVEAALPGVPTAPAAPGPAPSPAPVPAPPPP

PPPPPPATPVTPAPVPPFEKQGEKDKEDKQTFQVTDCRSLVKTLVCGVKTI

TWGITSCKAPGEAQFIPNKQLQPKETQIYIKLVKYAMQALDIYQVQIAGNG

QTYIRVANCQTVRMKEEKEVLEHFAGVFTMMNPLTFKEIFQTTVPYMVERI

SKNYALQIVANSFLANPTTSALEATILVEYLLDRLPEMGSNVELSNLYLKL

FKLVFGSVSLFAAENEQMLKPHLHKIVNSSMELAQTAKEPYNYFLLLRALF

RSIGGGSHDLLYQEFLPLLPNLLQGLNMLQSGLHKQHMKDLFVELCLTVPV

RLSSLLPYLPMLMDPLVSALNGSQTLVSQGLRTLELCVDNLQPDFLYDHIQ

PVRAELMQALWRTLRNPADSISHVAYRVLGKFGGSNRKMLKESQKLHYVVT

EVQGPSITVEFSDCKASLQLPMEKAIETALDCLKSANTEPYYRRQAWEVIK

CELVAMMSLEDNKHALYQLLAHPNETEKTIPNVIISHRYKAQDTPARKTFE

QALTGAFMSAVIKDLRPSALPFVASLIRHYTMVAVAQQCGPFLLPCYQVGS

QPSTAMEHSEENGSKGMDPLVLIDAIAICMAYEEKELCKIGEVALAVIFDV

ASIILGSKERACQLPLFSYIVERLCACCYEQAWYAKLGGVVSIKFLMERLP

LTWVLQNQQTELKALLEVMMDLTGEVSNGAVAMAKTTLEQLLMRCATPLKD

EERAEEIVAAQEKSFHHVTHDLVREVTSPNSTVRKQAMHSLQVLAQVTGKS

VTVIMEPHKEVLQDMVPPKKHLLRHQPANAQIGLMEGNTFCTTLQPRLFTM

DLNVVEHKVFYTELLNLCEAEDSALTKLPCYKSLPSLVPLRIAALNALAAC

NYLPQSREKIIAALFKALNSTNSELQEAGEACMRKFLEGATIEVDQIHTHM

RPLLMMLGDYRSLTLNVVNRLTSVTRLFPNSENDKECDQMMQHLRKWMEVV

VITHKGGQRSDGNESISECGRCPLSPFCQFEEMKICSAIINLFHLIPAAPQ

TLVKPLLEVVMKTERAMLIEAGSPFREPLIKFLTRHPSQTVELFMMEATLN

DPQWSRMFMSFLKHKDARPLRDVLAANPNRFITLLLPGGAQTAVRPGSPST

STMRLDLQFQAIKIISIIVKNDDSWLASQHSLVSQLRRVWVSENFQERHRK

ENMAATNWKEPKLLAYCLLNYCKRNYGDIELLFQLLRAFTGRFLCNMTFLK

EYMEEEIPKNYSIAQKRALFFRFVDFNDPNFGDELKAKVLQHILNPAFLYS

FEKGEGEQLLGPPNPEGDNPESITSVFITKVLDPEKQADMLDSLRIYLLQY

```
ATLLVEHAPHHIHDNNKNRNSKLRRLMTFAWPCLLSKACVDPACKYSGHLL
LAHIIAKFAIHKKIVLQVFHSLLKAHAMEARAIVRQAMAILTPAVPARMED
GHQMLTHWTRKIIVEEGHTVPQLVHILHLIVQHFKVYYPVRHHLVQHMVSA
MQRLGFTPSVTIEQRRLAVDLSEVVIKWELQRIKDQQPDSDMDPNSSGEGV
NSVSSSIKRGLSVDSAQEVKRFRTATGAISAVFGRSQSLPGADSLLAKPID
KQHTDTVVNFLIRVACQVNDNTNTAGSPGEVLSRRCVNLLKTALRPDMWPK
SELKLQWFDKLLMTVEQPNQVNYGNICTGLEVLSFLLTVLQSPAILSSFKP
LQRGIAACMTCGNTKVLRAVHSLLSRLMSIFPTEPSTSSVASKYEELECLY
AAVGKVIYEGLTNYEKATNANPSQLFGTLMILKSACSNNPSYIDRLISVFM
RSLQKMVREHLNPQAASGSTEATSGTSELVMLSLELVKTRLAVMSMEMRKN
FIQAILTSLIEKSPDAKILRAVVKIVEEWVKNNSPMAANQTPTLREKSILL
VKMMTYIEKRFPEDLELNAQFLDLVNYVYRDETLSGSELTAKLEPAFLSGL
RCAQPLIRAKFFEVFDNSMKRRVYERLLYVTCSQNWEAMGNHFWIKQCIEL
LLAVCEKSTPIGTSCQGAMLPSITNVINLADSHDRAAFAMVTHVKQEPRER
ENSESKEEDVEIDIELAPGDQTSTPKTKELSEKDIGNQLHMLTNRHDKFLD
TLREVKTGALLSAFVQLCHISTTLAEKTWVQLFPRLWKILSDRQQHALAGE
ISPFLCSGSHQVQRDCQPSALNCFVEAMSQCVPPIPIRPCVLKYLGKTHNL
WFRSTLMLEHQAFEKGLSLQIKPKQTTEFYEQESITPPQQEILDSLAELYS
LLQEEDMWAGLWQKRCKYSETATAIAYEQHGFFEQAQESYEKAMDKAKKEH
ERSNASPAIFPEYQLWEDHWIRCSKELNQWEALTEYGQSKGHINPYLVLEC
AWRVSNWTAMKEALVQVEVSCPKEMAWKVNMYRGYLAICHPEEQQLSFIER
LVEMASSLAIREWRRLPHVVSHVHTPLLQAAQQIIELQEAAQINAGLQPTN
LGRNNSLHDMKTVVKTWRNRLPIVSDDLSHWSSIFMWRQHHYQGKPTWSGM
HSSSIVTAYENSSQHDPSSNNAMLGVHASASAIIQYGKIARKQGLVNALDI
LSRIHTIPTVPIVDCFQKIRQQVKCYLQLAGVMGKNECMQGLEVIESTNLK
YFTKEMTAEFYALKGMFLAQINKSEEANKAFSAAVQMHDVLVKAWAMWGDY
LENIFVKERQLHLGVSAITCYLHACRHQNESKSRKYLAKVLWLLSFDDDKN
TLADAVDKYCIGVPPIQWLAWIPQLLTCLVGSEGKLLLNLISQVGRVYPQA
VYFPIRTLYLTLKIEQRERYKSDPGPIRATAPMWRCSRIMHMQRELHPTLL
SSLEGIVDQMVWFRENWHEEVLRQLQQGLAKCYSVAFEKSGAVSDAKITPH
TLNFVKKLVSTFGVGLENVSNVSTMFSSAASESLARRAQATAQDPVFQKLK
GQFTTDFDFSVPGSMKLHNLISKLKKWIKILEAKTKQLPKFFLIEEKCRFL
SNFSAQTAEVEIPGEFLMPKPTHYYIKIARFMPRVEIVQKHNTAARRLYIR
GHNGKIYPYLVMNDACLTESRREERVLQLLRLLNPCLEKRKETTKRHLFFT
VPRVVAVSPQMRLVEDNPSSLSLVEIYKQRCAKKGIEHDNPISRYYDRLAT
VQARGTQASHQVLRDILKEVQSNMVPRSMLKEWALHTFPNATDYWTFRKMF
TIQLALIGFAEFVLHLNRLNPEMLQIAQDTGKLNVAYFRFDINDATGDLDA
NRPVPFRLTPNISEFLTTIGVSGPLTASMIAVARCFAQPNFKVDGILKTVL
RDEIIAWHKKTQEDTSSPLSAAGQPENMDSQQLVSLVQKAVTAIIVITRLH
NLAQFEGGESKVNTLVAAANSLDNLCRMDPAWHPWL
```

By "TRRAP polynucleotide" is meant any nucleic acid molecule encoding an TRRAP polypeptide or fragment thereof. An exemplary TRRAP nucleic acid sequence is provided at NCBI Ref: NM_001244580.1:

(SEQ ID NO: 10)
```
  1 cgcgccgggg cctggtgctc ggtcggcggg tgctgccgct ttaagcgggg gcgggactgc
 61 gcgcggccga gcggttgcga cgagggctcg gctgggggtc gccggggtcg cgggccgggc
121 ctgcaggagc cgggccgccg aggtcgggc tggttgaact catggacctg atactttct
181 cttgagaagc aaaccagccc aaaagaaaaa tggcgtttgt tgcaacacag ggggccacgg
241 tggttgacca gaccactttg atgaaaaagt accttcagtt tgtggcagct ctcacagatg
301 tgaatacacc tgatgaaaca aagttgaaaa tgatgcaaga agttagtgaa aattttgaga
361 atgtcacgtc atctcctcag tattctacat tcctagaaca tatcatccct cgattcctta
421 catttctcca agatggagaa gttcagtttc ttcaggagaa accagcacag caactgcgga
481 agctcgtact tgaaataatt catagaatac caaccaacga acatcttcgt cctcacacaa
541 aaaatgtttt gtctgtgatg tttcgctttt tagagacgga aaatgaagaa aatgttctta
601 tttgtctaag aataattatt gagctacaca aacagttcag gccaccgatc acacaagaaa
661 ttcatcattt tctggatttt gtgaaacaga tttacaagga gcttccaaaa gtagtgaacc
721 gctactttga gaaccctcaa gtgatcccg agaacacagt gcctccccca gaaatggttg
781 gtatgataac aacgattgct gtgaaagtca acccggagcg tgaggacagt gagactcgaa
841 cacattccat cattccgagg ggatcacttt ctctgaaagt gttggcagaa ttgcccatta
901 ttgttgtttt aatgtatcag ctctacaaac tgaacatcca caatgttgtt gctgagtttg
961 tgcccttgat catgaacacc attgccattc aggtgtctgc acaagcgagg caacataagc
```

-continued

```
1021  tttacaacaa ggagttgtat gctgacttca ttgctgctca gattaaaaca ttgtcatttt
1081  tagcttacat tatcaggatt taccaggagt tggtgactaa gtattctcag cagatggtga
1141  aaggaatgct ccagttactt tcaaattgtc cagcagagac tgcacacctc agaaaggagc
1201  ttctgattgc tgccaaacac atcctcacca cagagctgag aaaccagttc attccttgca
1261  tggacaagct gtttgatgaa tccatactaa ttggctcagg atatactgcc agagagactc
1321  taaggcccct cgcctacagc acgctggccg acctcgtgca ccatgtccgc cagcacctgc
1381  ccctcagcga cctctccctc gccgtccagc tcttcgccaa gaacatcgac gatgagtccc
1441  tgcccagcag catccagacc atgtcctgca agctcctgct gaacctggtg gactgcatcc
1501  gttccaagag cgagcaggag agtggcaatg ggagagacgt cctgatgcgg atgctggagg
1561  ttttcgttct caaattccac acaattgctc ggtaccagct ctctgccatt tttaagaagt
1621  gtaagcctca gtcagaactt ggagccgtgg aagcagctct gcctggggtg cccactgccc
1681  ctgcagctcc tggccctgct ccctccccag cccctgtccc tgccccacct ccaccccgc
1741  ccccacccc acctgccacc cctgtgaccc cggccccgt gcctcccttc gagaagcaag
1801  gagaaaagga caaggaagac aagcagacat tccaagtcac agactgtcga agtttggtca
1861  aaaccttggt gtgtggtgtc aagacaatca cgtggggcat aacatcatgc aaagcacctg
1921  gtgaagctca gttcattccc aacaagcagt tacaacccaa agagacacag atttacatca
1981  aacttgtgaa atatgcaatg caagctttag atatttatca ggtccagata gcaggaaatg
2041  gacagacata catccgtgtg gccaactgcc agactgtgag aatgaaagag gagaaggagg
2101  tattggagca tttcgctggt gtgttcacaa tgatgaaccc cttaacgttc aaagaaatct
2161  tccaaactac ggtcccttat atggtggaga aatctcaaa aaattatgct cttcagattg
2221  ttgccaattc cttcttggca aatcctacta cctctgctct gtttgctacg attctggtgg
2281  aatatctcct tgatcgcctg ccagaaatgg gctccaacgt ggagctctcc aacctgtacc
2341  tcaagctgtt caagctggtc tttggctctg tctccctctt tgcagctgaa aatgaacaaa
2401  tgctgaagcc tcacttgcac aagattgtga acagctctat ggagctcgcg cagactgcca
2461  aggaacccta caactacttc ttgctgctac gggcgctgtt tcgctctatt ggtggaggta
2521  gccacgatct cttgtatcag gagttcttgc ctctccttcc aaacctcctg caagggctga
2581  acatgcttca gagtggcctg cacaagcagc acatgaagga cctctttgtg gagctgtgtc
2641  tcaccgtccc tgtgcggctg agctcgcttt tgccgtacct gcccatgctt atggatccct
2701  tggtgtctgc actcaatggg tctcagacat tggtcagcca aggcctcagg acgctggagc
2761  tgtgtgtgga caacctgcag cccgacttcc tctacgacca catccagccg gtgcgcgcag
2821  agctcatgca ggctctgtgg cgcaccttac gcaacccctgc tgacagcatc tcccacgtgg
2881  cctaccgtgt gctcggtaag tttggcggca gtaacaggaa gatgctgaag gagtcgcaga
2941  agctgcacta cgttgtgacc gaggttcagg gccccagcat cactgtggag ttttccgact
3001  gcaaagcttc tctccagctc cccatggaga aggccattga aactgctctg gactgcctga
3061  aaagcgccaa cactgagccc tactaccgga ggcaggcgtg ggaagtgatc aaatgcttcc
3121  tggtggccat gatgagcctg gaggacaaca agcacgcact ctaccagctc ctggcacacc
3181  ccaactttac agaaaagacc atccccaatg ttatcatctc acatcgctac aaagcccagg
3241  acactccagc ccggaagact tttgagcagg ccctgacagg cgccttcatg tctgctgtca
3301  ttaaggacct gcggcccagc gccctgccct tgtcgccag cttgatccgc cactatacga
3361  tggtggcagt cgcccagcag tgtggccctt tcttgctgcc ttgctaccag gtgggcagcc
3421  agcccagcac agccatgttt cacagtgaag aaaatggctc gaaaggaatg gatcctttgg
```

-continued

```
3481  ttctcattga tgcaattgct atttgtatgg catatgaaga aaaggagctt tgcaaaatcg
3541  gggaggtggc cctagctgtg atatttgatg ttgcaagtat catcctgggc tccaaggaga
3601  gggcctgcca gctgcccctg ttttcttaca tcgtggagcg cctgtgtgca tgttgttatg
3661  aacaggcgtg gtatgcaaag ctgggggggtg tggtgtctat taagtttctc atggagcggc
3721  tgcctctcac ttgggttctc cagaaccagc agacattcct gaaagcactt ctctttgtca
3781  tgatggactt aactggagag gtttccaatg gggcagtcgc tatggcaaag accacgctgg
3841  agcagcttct gatgcggtgc gcaacgcctt taaaagacga ggagagagcc gaagagatcg
3901  tggccgccca ggaaaagtct ttccaccatg tgacacacga cttggttcga gaagtcacct
3961  ctccaaactc cactgtgagg aagcaggcca tgcattcgct gcaggtgttg gcccaggtca
4021  ctgggaagag tgtcacggtg atcatggaac cccacaaaga ggtcctgcag gatatggtcc
4081  cccctaagaa gcacctgctc cgacaccagc ctgccaacgc acagattggc ctgatggagg
4141  ggaacacgtt ctgtaccacg ttgcagccca ggctcttcac aatggacctt aacgtggtgg
4201  agcataaggt gttctacaca gagctgttga atttgtgtga ggctgaagat tcagctttaa
4261  caaagctgcc ctgttataaa agccttccgt cactcgtacc tttacgaatt gcggcattaa
4321  atgcacttgc tgcctgcaat taccttcctc agtccaggga gaaaatcatc gctgcactct
4381  tcaaagccct gaattccacc aatagtgagc tccaagaggc cggagaagcc tgtatgagaa
4441  agttttttaga aggtgctacc atagaagtcg atcaaatcca cacacatatg cgacctttgc
4501  tgatgatgct gggagattac cggagcttga cgctgaatgt tgtgaatcgc ctgacttcgg
4561  tcacgaggct cttcccaaat tccttcaatg ataaattttg tgatcagatg atgcaacatc
4621  tgcgcaagtg gatggaagtg gtggtgatca cccacaaagg gggccagagg agcgacggaa
4681  acgaaagcat ttccgagtgc gggagatgtc ccttgtctcc attctgtcag tttgaggaaa
4741  tgaagatttg ctcagcaatt ataaacctttt tcatctgat cccggctgct cctcagacac
4801  tggtgaagcc tttgctagag gttgtcatga aaacggagcg ggcgatgctg atcgaggcgg
4861  ggagtccatt ccgagagccc ctgatcaagt tcctgactcg acatccctcg cagacagtgg
4921  agctgttcat gatggaagcc acactgaacg atccccagtg gagcagaatg tttatgagtt
4981  ttttaaaaca caaagacgcc agacctctgc gggatgtgct ggctgccaac cccaacaggt
5041  tcatcaccct gctgctgccg gggggtgccc agacggctgt gcgccccggt tcgcccagca
5101  ccagcaccat gcgcctggac ctccagttcc aggccatcaa gatcataagc attatagtga
5161  aaaacgatga ctcctggctg gccagccagc actctctggt gagccagttg cgacgtgtgt
5221  gggtgagtga gaacttccaa gagaggcacc gcaaggagaa catggcagcc accaactgga
5281  aggagcccaa gctgctggcc tactgcctgc tgaactactg caaaaggaat tacggagata
5341  tagaattgct gttccagctg ctccgagcct ttactggtcg tttttctctgc aacatgacat
5401  tcttaaaaga gtatatggag gaagagattc ccaaaaatta cagcatcgct cagaaacgtg
5461  ccctgttctt tcgctttgta gacttcaacg accccaactt cggagatgaa ttaaaagcta
5521  aagttctgca gcatatcttg aatcctgctt tcttgtacag ctttgagaag ggggaaggag
5581  agcagctctt gggacctccc aatccagaag gagataaccc agaaagcatc accagtgtgt
5641  ttattaccaa ggtcctggac cccgagaagc aggcggacat gctggactcg ctgcggatct
5701  acctgctgca gtacgccacg ctgctggtgg agcacgcccc ccaccacatc catgacaaca
5761  acaagaaccg caacagcaag ctgcgccgcc tcatgacctt cgcctggccc tgcctgctct
5821  ccaaggcctg cgtggaccca gcctgcaagt acagcggaca cttgctcctg gcgcacatta
```

-continued

```
5881 tcgccaaatt cgccatacac aagaagatcg tcctgcaggt ttttcatagt ctcctcaagg
5941 ctcacgcaat ggaagctcga gcgatcgtca gacaggcgat ggccattctg accccggcgg
6001 tgccggccag gatggaggac gggcaccaga tgctgaccca ctggacccgg aagatcattg
6061 tggaggaggg gcacaccgtc ccgcagctgg tccacattct gcacctgata gtgcaacact
6121 tcaaggtgta ctacccggta cggcaccact tggtgcagca catggtgagc gccatgcaga
6181 ggctgggctt cacgcccagt gtcaccatcg agcagaggcg gctggccgtg gacctgtctg
6241 aagtcgtcat caagtgggag ctgcagagga tcaaggacca gcagccggat tcagatatgg
6301 acccaaattc cagtggagaa ggagtcaatt ctgtctcatc ctccattaag agaggcctgt
6361 ccgtggattc tgcccaggaa gtgaaacgct ttaggacggc caccggagcc atcagtgcag
6421 tctttgggag gagccagtcg ctacctggag cagactctct cctcgccaag cccattgaca
6481 agcagcacac agacactgtg gtgaacttcc ttatccgcgt ggcctgtcag gttaatgaca
6541 acaccaacac agcggggtcc cctggggagg tgctctctcg ccggtgtgtg aaccttctga
6601 agactgcgtt gcggccagac atgtggccca agtccgaact caagctgcag tggttcgaca
6661 agctgctgat gactgtggag cagccaaacc aagtgaacta tgggaatatc tgcacgggcc
6721 tagaagtgct gagcttcctg ctaactgtcc tccagtcccc agccatcctc agtagcttca
6781 aacctctgca gcgtggaatt gccgcctgca tgacatgtgg aaacaccaag gtgttgcgag
6841 ccgtccacag ccttctctcg cgcctgatga gcattttccc aacagagccg agtacttcca
6901 gtgtggcctc caaatatgaa gagctggagt gcctctacgc agccgtcgga aaggtcatct
6961 atgaagggct caccaactac gagaaggcca ccaatgccaa tccctcccag ctcttcggga
7021 cccttatgat cctcaagtct gcctgcagca acaacccag ctacatagac aggctgatct
7081 ccgtctttat gcgctccctg cagaagatgg tccgggagca tttaaaccct caggcagcgt
7141 caggaagcac cgaagccacc tcaggtacaa gcgagctggt gatgctgagt ctggagctgg
7201 tgaagacgcg cctggcagtg atgagcatgg agatgcggaa gaacttcatc caggccatcc
7261 tgacatccct catcgaaaaa tcaccagatg ccaaaatcct ccgggctgtg gtcaaaatcg
7321 tggaagaatg ggtcaagaat aactccccaa tggcagccaa tcagacacct acactccggg
7381 agaagtccat tttgcttgtg aagatgatga cttacataga aaaacgcttt ccggaagacc
7441 ttgaattaaa tgcccagttt ttagatcttg ttaactatgt ctacagggat gagaccctct
7501 ctggcagcga gctgacggcg aaacttgagc ctgcctttct ctctgggctg cgctgtgccc
7561 agccactcat cagggcaaag ttttcgagg tttttgacaa ctccatgaaa cgtcgtgtct
7621 acgagcgctt gctctatgtg acctgttcgc agaactggga agccatgggg aaccacttct
7681 ggatcaagca gtgcattgag ctgcttctgg ccgtgtgtga agagcacc cccattggca
7741 ccagctgcca aggagccatg ctcccgtcca tcaccaacgt catcaacctg gccgatagcc
7801 acgaccgtgc cgccttcgcc atggtcacac atgtcaagca ggagccccgg gagcgggaga
7861 acagcgagtc caaagaggag gatgtagaga tagacatcga actagctcct ggggatcaga
7921 ccagcacgcc caaaaccaaa gaactttcag aaaaggacat tggaaaccag ctgcacatgc
7981 taaccaacag gcacgacaag tttctggaca ctctccgaga ggtgaagact ggagcgctgc
8041 tcagcgcttt cgttcagctg tgccacattt ccacgacgct ggcagagaag acgtgggtcc
8101 agcttttccc cagattgtgg aagatcctct ctgacagaca gcagcatgca ctcgcgggtg
8161 agataagtcc atttctgtgc agcggcagtc accaggtgca gcgggactgc cagcccagcg
8221 cgctgaactg ctttgtggaa gccatgtccc agtgcgtgcc gccaatcccc atccgaccct
8281 gcgtcctgaa gtacctgggg aagacacaca acctctggtt ccggtccacg ctgatgttgg
```

-continued

```
8341 agcaccaggc ttttgaaaag ggtctgagtc ttcagattaa gccgaagcaa acaacggagt
8401 tttatgagca ggagagcatc accccgccgc agcaggagat actggattcc cttgcggagc
8461 tttactccct gttacaagag gaagatatgt gggctggtct gtggcagaag cggtgcaagt
8521 actcggagac agcgactgcg attgcttacg agcagcacgg gttctttgag caggcacaag
8581 aatcctatga aaaggcaatg gataaagcca aaaagaaca tgagaggagt aacgcctccc
8641 ctgctatttt ccctgaatac cagctctggg aagaccactg gattcgatgc tccaaggaat
8701 tgaaccagtg ggaagccctg acggagtacg gtcagtccaa aggccacatc aacccctacc
8761 tcgtcctgga gtgcgcctgg cgggtgtcca actgactgc catgaaggag cgctggtgc
8821 aggtggaagt gagctgtccg aaggagatgg cctggaaggt gaacatgtac cgcggatacc
8881 tggccatctg ccacccgag gagcagcagc tcagcttcat cgagcgcctg gtggagatgg
8941 ccagcagcct ggccatccgc gagtggcggc ggctgcccca cgtagtgtcc cacgtgcaca
9001 cgcctctcct acaggcagcc cagcaaatca tcgaactcca ggaagctgca caaatcaacg
9061 caggcttaca gccaaccaac ctgggaagga caacagcct gcacgacatg aagacggtgg
9121 tgaagacctg gaggaaccga ctgcccatcg tgtctgacga cttgtccac tggagcagca
9181 tcttcatgtg gaggcagcat cattaccagg gtaaaccgac ctggtccggc atgcattcat
9241 catcgattgt aactgcctat gagaatagct ctcagcatga tcccagttca aataacgcta
9301 tgcttgggt tcatgcatca gcttcagcga tcatccagta tggaaaaatc gcccggaaac
9361 aaggactggt caatgtagct ctggatatat taagtcggat tcatactatt ccaactgttc
9421 ctatcgtgga ttgcttccag aagattcgac agcaagttaa atgctacctc cagctggcag
9481 gcgtcatggg caaaaacgag tgcatgcagg gccttgaagt tattgaatct acaaatttaa
9541 aatacttcac aaaagagatg acagccgaat tttatgcact gaagggaatg ttcttggctc
9601 agatcaacaa gtccgaggag gcaaacaaag ccttctctgc agctgtgcag atgcacgatg
9661 tgctggtgaa agcctgggcc atgtggggcg actacctgga gaacatcttt gtgaaggagc
9721 ggcagctgca cctgggcgtg tctgccatca cctgctacct gcacgcctgc cggcatcaga
9781 acgagagcaa atcgaggaaa tacttagcca aggtgctgtg gcttttgagt tttgatgatg
9841 acaaaaacac tttggcagat gccgtcgaca agtactgcat tggtgtgcca cccatccagt
9901 ggctggcctg gatcccacag ctgctcacct gcctggttgg ctcggaggga aagctgctct
9961 tgaacctcat tagccaggtt ggacgcgtgt atccccaagc ggtctacttt ccatccgga
10021 ccctgtacct gaccctgaaa atagaacagc gggaacgcta caagagcgat ccaggggcca
10081 taagagcaac agcacccatg tggcgctgca gccgaatcat gcacatgcag cgagagctcc
10141 accccaccct tctgtcttcc ctggaaggca tcgtcgatca gatggtctgg ttcagagaaa
10201 attggcatga agaggttctc aggcagctcc aacagggcct ggcgaaatgt tactccgtgg
10261 cgtttgagaa aagtggagcg tgtccgatg ctaaaatcac ccccacact ctcaattttg
10321 tgaagaagtt ggtgagcacg tttggggtgg gcctggagaa tgtgtccaac gtctcgacca
10381 tgttctccag cgcagcctct gagtctctgg cccggcgggc gcaggccact gcacaagacc
10441 ctgtctttca gaagctgaaa ggccagttca cgacggattt tgacttcagc gttccaggat
10501 ccatgaagct tcataatctt atttctaagt tgaaaaagtg gatcaaaatc ttggaggcca
10561 agaccaagca actccccaaa ttcttcctca tagaggaaaa gtgccggttc ttgagcaatt
10621 tctcggcaca gacagctgaa gtgaaattc tggggagtt tctgatgcca aagccaacgc
10681 attattacat caagattgca cggttcatgc cccgggtaga gattgtgcag aagcacaaca
```

```
-continued
10741 ccgcagcccg gcggctgtac atccggggac acaatggcaa gatctaccca tacctcgtca 10801 tgaacgacgc ctgcctcaca gagtcacggc gagaggagcg tgtgttgcag ctgctgcgtc 10861 tgctgaaccc ctgtttggag aagagaaagg agaccaccaa gaggcacttg tttttcacag 10921 tgccccgggt tgtggcagtt tccccacaga tgcgcctcgt ggaggacaac ccctcttcac 10981 tttcccttgt ggagatctac aagcagcgct cgccaagaa gggcatcgag catgacaacc 11041 ccatctcccg ttactatgac cggctggcta cggtgcaggc gcggggaacc caagccagcc 11101 accaggtcct ccgcgacatc ctcaaggagg ttcagagtaa catggtgccg cgcagcatgc 11161 tcaaggagtg ggcgctgcac accttcccca atgccacgga ctactggacg ttccggaaga 11221 tgttcaccat ccagctggct ctgataggct tcgcggaatt cgtcctgcat ttaaatagac 11281 tcaaccccga gatgttacag atcgctcagg acactggcaa actgaatgtt gcctactttc 11341 gatttgacat aaacgacgcg actggagacc tggatgccaa ccgtcctgtc ccatttcgac 11401 tcacgcccaa catttctgag tttctgacca ccatcggggt ctccggcccg ttgacagcgt 11461 ccatgattgc ggtcgcccgg tgcttcgccc agccaaactt taaggtggat ggcattctga 11521 aaacggttct ccgggacgag atcattgctt ggcacaaaaa aacacaagag gacacgtcct 11581 ctcctctctc ggccgccggg cagccagaga acatggacag ccagcaactg gtgtccctgg 11641 ttcagaaagc cgtcaccgcc atcatgaccc gcctgcacaa cctcgcccag ttcgaaggcg 11701 gggaaagcaa ggtgaacacc ctggtggccg cggcaaacag cctggacaat ctgtgccgca 11761 tggacccgc ctggcacccc tggctgtgac tgtggccgcc acggccaccc ggaatgtgaa 11821 gggcgctccg ggctctgagc ccgcagcttt tacgacttct ccctgcctcg ttccttatat 11881 tcacagaagc cccatagttt cactgggttg cggttatttt cctggtagtt tgcgtgtaag 11941 aaagggagaa tatagtttta gaggaagctg aactatgacg atgctgggcg aagcggttgg 12001 aaatggcaga gctgaaactt attccaagct ttcaaaataa tcttttaaga agccaggatt 12061 ctccggtctg gaatttctga gtgagtcctt ttttatggt gtcctccctc tgtgaatgta 12121 caggcggaac tgtacgaaca gctcccttcc atccattttt aactctttcg gaaataacac 12181 ctcacagcag cttcgtgctt ttgtacagac cttttgtaaca agtgtacaga aaactcattt 12241 tgtttgagaa acaggagttg atgaacccat catgctggtt tttctctgag cacaaagttt 12301 taggctgtac acagccagcc ttgggaatct cgttgagcgt tcggcgtgga tccacggggc 12361 caggccaccc tgcgggagcg ccacacgcat ccacttcgga ttcagtgggt gaagacagaa 12421 ctctgagagt ctgcaggcgg ctcctgtgct tttatttct ggctcttcgg atgtcttcta 12481 gacatttact atcactgcac ctgaagaaaa aatcacttt accttcctaa tttaaaaga 12541 caaaacagaa atgtacgttc cttcgctagc tttagtcttt ctgttcccat ttttataaat 12601 ctgagcattg ataatgttct atctaaattt gtacagtgtg attttttttt ttagaataaa 12661 tattttataa aagggttaaa aaaaaaaaaa aaaaa
```

In certain implementations, the marker that detects polynucleotide may be the polynucleic region that encodes the protein.

By "alteration" is meant a change (increase or decrease) in the expression levels or activity of a gene or polypeptide as detected by standard art known methods, such as those described herein. As used herein, an alteration includes at least a 10% change in expression levels, for example a 25% change, a 40% change, and a 50% or greater change in expression levels.

A "chemically induced" complex (e.g., chemically induced PDE3A-SLFN12 complex, chemically induced PDE3B-SLFN12 complex) is the complex formed by indicated agents following contact with an active compound, such as a PDE3A modulator or a PDE3B modulator. Typically, the active compounds described herein are a chemical compound inducing PDE3A-SLFN12 or PDE3B-SLFN12 complexes, such as e.g. DNMDP or a compound of WO2019/025562.

By "modulator" is meant any agent that binds to a polypeptide and alters a biological function or activity of the polypeptide. A modulator includes, without limitation, agents that increase binding of a polypeptide to another agent. For example, a modulator may promote binding of a polypeptide to another polypeptide. In some embodiments a modulator of PDE3A or PDE3B promotes binding of these proteins to SLFN12. In some embodiments, a modulator of PDE3A polypeptide is DNMDP. In other embodiments, a modulator of PDE3A is an exemplified compound of WO2019/025562.

The term "capture reagent" refers to a reagent, for example an antibody or antigen binding protein, capable of binding a target molecule or analyte to be detected in a biological sample. The capture reagent may be immobilized, for example on an assay surface, such as a solid substrate or reaction vessel. The capture reagents described herein may bind to one or more of PDE3A, PDE3B, SLFN12, AIP, and TRRAP.

"Detect" refers to identifying the presence, absence or amount of the analyte to be detected. In particular embodiments, the analyte is an AIP, TRRAP, PDE3A, PDE3B, or SLFN12 polypeptide.

By "effective amount" or "therapeutically effective amount" is meant the amount of a compound described herein required to ameliorate the symptoms (e.g., treat, prevent) of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. In some embodiments, the compound is DNMDP or a compound of WO2019/025562.

The terms "healthy", "normal" and "non-neoplastic" are used interchangeably herein to refer to a subject or particular cell or tissue that is devoid (at least to the limit of detection) of a disease condition, such as a neoplasia. In some embodiments, the reference may be a healthy cell.

The disclosure provides a number of targets that are useful for the development of highly specific drugs to treat or a disorder characterized by the methods delineated herein. In addition, the methods of the disclosure provide a route for analyzing virtually any number of compounds for effects on a disease described herein with high-volume throughput, high sensitivity, and low complexity.

By "fragment" is meant a portion of a polypeptide or nucleic acid molecule. This portion contains, for example, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "marker" or "biomarker" is meant any protein or polynucleotide having an alteration in expression level or activity relative to a reference that is associated with a disease or disorder, such as cancer. In particular embodiments, a marker of the disclosure is AIP (e.g., AIP polypeptide, AIP polynucleotide), TRRAP (e.g., TRRAP polypeptide, TRRAP polynucleotide), PDE3A (e.g., PDE3A polypeptide, PDE3A polynucleotide), PDE3B (e.g., PDE3B polypeptide, PDE3B polynucleotide), or SLFN12 (e.g., SLFN12 polypeptide, SLFN12 polynucleotide). In certain implementations, the marker may comprise portions of a polynucleotides sequence (e.g., SEQ ID NOS: 1, 4, 6, 8, 10) which encode the polypeptide (e.g., AIP polypeptide, TRRAP polypeptide, PDE3A polypeptide, PDE3B polypeptide, SLFN12 polypeptide). In some embodiments, the marker may have any one of SEQ ID NOS: 1-11. In some embodiments, a marker may comprise at least 75% or at least 80% or at least 85% sequence identity to SEQ ID NOS 2, 3, 5, 7, 9, or 11. In certain embodiments, the presence of a marker in a cancer cell identifies that cell as responsive to therapy.

Nucleic acid molecules (e.g., polynucleotides) useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having substantial identity to an endogenous sequence are typically capable of hybridizing with at least one strand of a double-stranded nucleic acid molecule. Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Typically, when polynucleotides hybridize and at least one strand of a nucleic acid molecule hybridizes, they are able to pair to form a double-stranded molecule between complementary polynucleotide sequences (e.g., a gene described herein), or portions thereof, under various conditions of stringency.

For example, "stringent" salt concentration will ordinarily be less than about 750 mM NaCl and 75 mM trisodium citrate or less than about 500 mM NaCl and 50 mM trisodium citrate or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. Stringent temperature conditions will ordinarily include temperatures of at least about 30° C. or at least about 37° C. of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a specific embodiment, hybridization will occur at 30° C. in 750 mM NaCl, 75 mM trisodium citrate, and 1% SDS. In some embodiments, hybridization will occur at 37° C. in 500 mM NaCl, 50 mM trisodium citrate, 1% SDS, 35% formamide, and 100 µg/ml denatured salmon sperm DNA (ssDNA). In certain aspects, hybridization may occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps may be less than about 30 mM NaCl and 3 mM trisodium citrate, or more less than about 15 mM NaCl and 1.5 mM trisodium citrate. Stringent temperature conditions for the wash steps will ordinarily include a temperature of at least about 25° C., for example of at least about 42° C., or at least about 68° C. In some embodiments, wash steps will occur at 25° C. in 30 mM NaCl, 3 mM trisodium citrate, and 0.1% SDS. In certain embodiments, wash steps will occur at 42 C in 15 mM NaCl, 1.5 mM trisodium citrate, and 0.1% SDS. In a specific implementation, wash steps may occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

Typically, substantially identical polypeptides or nucleic acids exhibit at least 50% identity to a reference amino acid sequence (for example, any one of the amino acid sequences described herein) or nucleic acid sequence (for example, any one of the nucleic acid sequences described herein). In certain implementations, such a sequence is at least 60%, or at least 80% or 85% or at least 90% or at least 95% or at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions may include substitutions within the following groups:
  glycine, alanine;
  valine, isoleucine, leucine;
  aspartic acid, glutamic acid, asparagine, glutamine;
  aspartic acid, glutamic acid;
  asparagine, glutamine;
  serine, threonine; lysine, arginine; and
  phenylalanine, tyrosine.
In an exemplary approach to determining the degree of identity, a BLAST program may be used, with a probability score between $e^{-3}$ and $e^{-100}$ indicating a closely related sequence.

The term "pharmaceutical composition," as used herein, represents a composition containing a compound (e.g., a PDE3 modulator) formulated with a pharmaceutically acceptable excipient. In some embodiments, the pharmaceutical composition is manufactured or sold with the approval of a governmental regulatory agency as part of a therapeutic regimen for the treatment of a disease in a mammal. Pharmaceutical compositions can be formulated, for example, for oral administration in unit dosage form (e.g., a tablet, capsule, caplet, gelcap); for topical administration (e.g., as a cream, gel, lotion, ointment); for intravenous administration (e.g., as a sterile solution free of particulate emboli and in a solvent system suitable for intravenous use); or in any other formulation described herein.

Useful pharmaceutical carriers for the preparation of the compositions hereof, can be solids, liquids, or gases. Thus, the compositions can take the form of tablets, pills, capsules, suppositories, powders, enterically coated or other protected formulations (e.g., binding on ion-exchange resins), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are liquid carriers, particularly (when isotonic with the blood) for injectable solutions. For example, formulations for intravenous administration comprise sterile aqueous solutions of the active compound(s) which are prepared by dissolving solid active compound(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives, such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

As used herein, the term "pharmaceutically acceptable salt" refers to salts of any of the compounds mentioned herein that within the scope of sound medical judgment, are suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

As used herein, the term "subject" refers to any organism to which a composition in accordance with the disclosure may be administered, e.g., for experimental, diagnostic, prophylactic, and/or therapeutic purposes. Typical subjects include any animal (e.g., mammals, such as mice, rats, rabbits, non-human primates, and humans). The subject may be domesticated animals (e.g., cows, calves, sheep, lambs, horses, foals, pigs, piglets), or animals in the family Muridae (e.g., rats, mice). A subject may seek or be in need of treatment, require treatment, be receiving treatment, may be receiving treatment in the future, or a human or animal that is under care by a trained professional for a particular disease or condition.

A "patient in need thereof" as used herein, refers to a human individual who may be identified as having a disease, disorder, or condition responsive to complex formation. As described herein, in some embodiments, an individual in need thereof is suffering from a proliferative disorder, such as cancer. In some embodiments, an individual in need thereof has been diagnosed by a medical doctor with a proliferative disorder requiring treatment. A patient in need or an individual in need are used interchangeably herein.

As used herein, the term "reference" or "reference level" refers to an amount or concentration of the indicated biomarker (e.g., SLFN12, PDE3A, PDE3B, AIP, TRRAP), which may be of interest for comparative purposes. For example, a reference level may be the level of the indicated biomarker expressed as an average of the level of the biomarker from samples taken from a control population of healthy subjects. In some embodiments, a reference level may be the level of the indicated biomarker expressed as an average of the level of the biomarker measured from a plurality cancer cell lines (e.g., the cancer cell lines measured in FIG. 5). In one embodiment, the "reference" is a standard or control condition. Suitable samples or references for determining reference levels include healthy cells, cells nonresponsive to chemically induced complex formation (e.g., cells nonresponsive to PDE3A modulation, cells nonresponsive to PDE3B modulation), non-cancerous cells, normal tissue, and the like. In various implementations, the reference may be the average expression level of cancerous cells. In some embodiments, the reference to determine the reference level of an indicated biomarker may be a derived from the subject, a subject known not to suffer from cancer, such as a healthy subject, or a population of subjects. Suitable references include a concurrently run control, or a standard which may be created by assaying one or more non-cancer cells and collecting biomarker data. Thus, the control sample may optionally be a standard that is created and used continuously. The standard includes, for example, the average level of a biomarker in a sample from a non-cancer control group. In certain embodiments, the reference is derived from a sample of a subject known not to suffer from cancer.

As used herein, and as well understood in the art, "to treat" a condition or "treatment" of the condition (e.g., the conditions described herein, such as cancer) is an approach for obtaining beneficial or desired results, such as clinical results. Treatment of a subject may include a decrease in the proliferation of cancer cells in the subject. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Chemical Inducers of PDE3A/B-SLFN12 Complexes

Without wishing to be bound by theory, it is believed that certain chemical agents are able to induce complexation in certain responsive cells between specific phosphodiesterase and schlafen proteins in the presence of AIP and TRRAP. As shown in WO 2017/027854, hereby incorporated by reference in its entirety, increased expression of PDE3A and SLFN12 has been shown to correlate with cytotoxicity of certain chemical agents (i.e., "complex inducers" or "complex inducing active compounds"), such as PDE3A modulators. As shown herein, selective apoptosis of only malignant biomarker positive cells may occur following chemical induction of PDE3A/B-SLFN12 formation. The present disclosure is partially premised on the discovery that AIP and TRRAP peptides are implicated in the apoptotic response of cancer cells. Expression of combinations of these biomarkers have been shown to correlate with complex inducing active compound (e.g., PDE3 modulator, PDE3A modulator, PDE3B modulator) sensitivity. Using AIP and TRRAP as biomarkers allows for further stratification of cells responsive to PDE3A-SLFN12 or PDE3B-SLFN12 complex formation, and particularly, chemically induced complexation. This increased stratification allows for more efficient identification of specific chemical agents for the treatment or prophylaxis of diseases, disorders, or conditions in that patient population with responsive cells. Furthermore, it facilitates identification of patients who will benefit from a treatment with PDE3 modulators, such as a PDE3A modulator and/or a PDE3B modulator operative via PDE3A-SLFN12 and/or PDE3B-SLFN12 complex formation.

Figure 5:
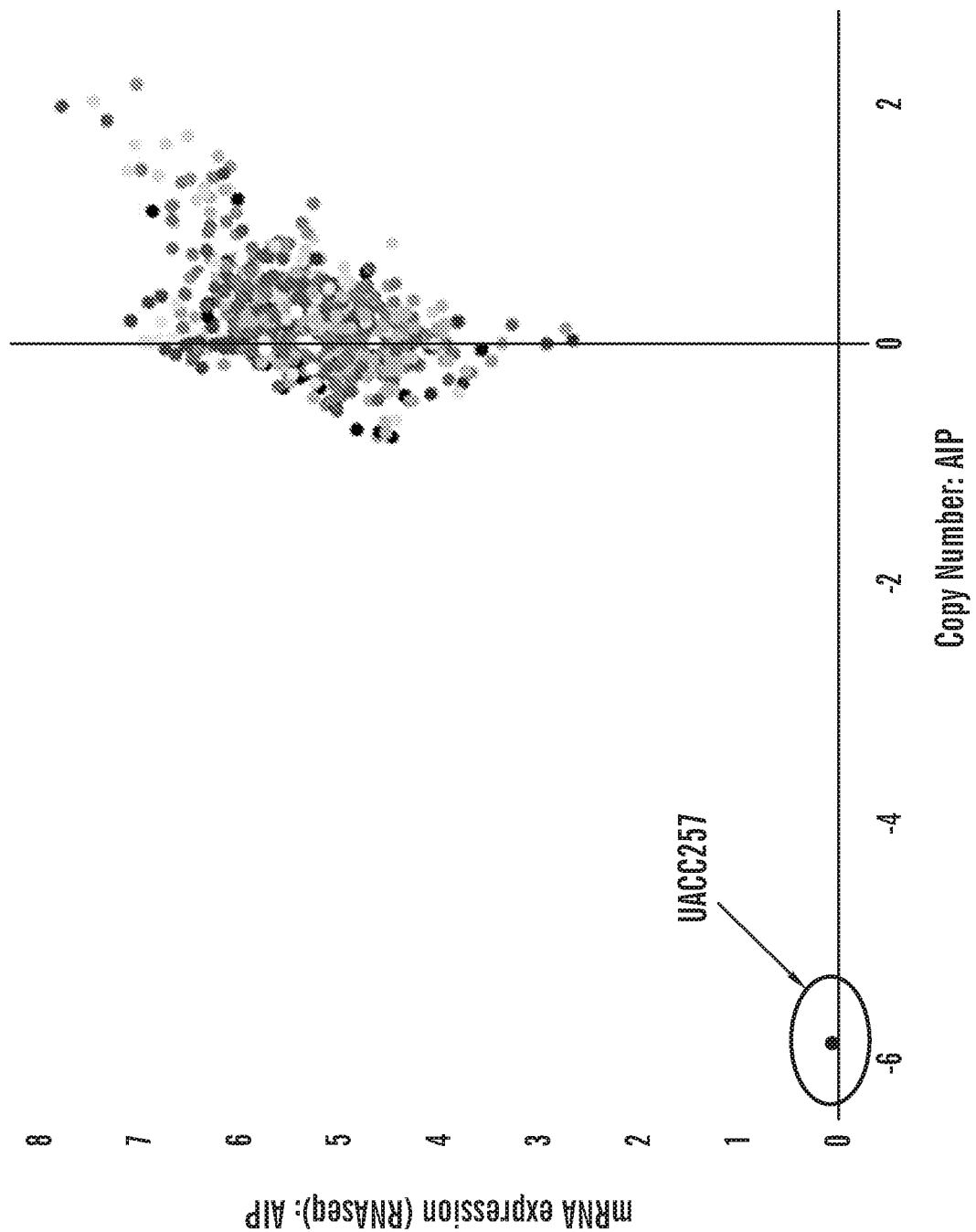
FIG. 5 compares the gene copy number and expression of AIP in the measured cell lines and identifies the UACC257 cell line as lacking AIP expression.

Once a cell is identified as responsive to complex formation by the methods described herein (e.g., by expression of AIP and/or TRAPP; and increased expression of PDE3A or PDE3B relative to a reference, such as a healthy control cell or the average expression level of cancerous cells such as those cells measured in FIG. 5; and increased expression of SLFN12 relative to reference, such as a healthy control cell or the average expression level of cancerous cells), apoptosis of that cell may occur by chemical induction of complex formation by one or more PDE3 modulators Complex inducing active compounds may be delivered to responsive cell lines to induce complexation between PDE3A-SLFN12 and/or PDE3B-SLFN12 which may result in apoptosis in only those cells susceptible to complex formation (e.g., cancer cells). In some embodiments, the PDE3A-SLFN12 complex inducing active compound is a PDE3 modulator, such as a PDE3A modulator or a PDE3B modulator. In various implementations, the PDE3B-SLFN12 complex inducing active compound is a PDE3 modulator, such as a PDE3A modulator or a PDE3B modulator. For example, the complex inducing active compound may be DNMDP or a compound of WO2019/025562.

The identification of complex inducing active compounds including PDE3 (e.g., PDE3A, PDE3B) modulators suitable for use as therapeutic agents to induce PDE3A/B-SLFN12 complex formation may be made with a phenotypic screen designed to identify cytotoxic small molecules that preferentially kill cancer cells over a healthy cell through complex formation of PDE3A-SLFN12 or PDE3B-SLFN12 upon administration. A predictive chemogenomics approach may complement target-driven drug development programs, which typically consist of extensive in vitro and in vivo target validation. Many U.S. Food and Drug Administration (FDA)-approved targeted therapies have been developed this way, among them small-molecule kinase inhibitors that target oncogenic somatic driver mutations. However, the discovery and development of targeted therapies is often hampered by limitations in knowledge of the biological function of the target, its mechanism of action, and the available chemical matter to selectively modulate the target. The present disclosure is related to increasing that knowledge base.

Phenotypic screening can discover novel targets for cancer therapy whose specific molecular mechanism is often elucidated by future studies. For example, a phenotypic screen developed to identify small molecules causing synthetic lethality in tp53 mutant cancer cells enabled the serendipitous discovery of a class of cancer-selective cytotoxic agents which act as modulators of phosphodiesterase 3A (PDE3A). Many PDE3A modulators also directly bind PDE3B proteins and a PDE3A modulator may be used to induce complexation between SLFN12 and PDE3B. Cyclic nucleotide phosphodiesterases catalyze the hydrolysis of second messenger molecules cyclic adenosine monophosphate (cAMP) and cyclic guanosine monophosphate (cGMP), and are important in many physiological processes.

The present disclosure provides methods for identifying subjects that have a malignancy that is likely to respond to PDE3 modulator treatment based on the expression of AIP and/or TRRAP in a subject biological sample comprising a cancer cell which also expresses increased levels PDE3A and SLFN12 or PDE3B and SLFN12 relative to a reference.

Examples of PDE3A modulators include DNMDP (6-(4-(diethylamino)-3-nitrophenyl)-5-methyl-4,5-dihydro-pyridazin-3(2H)-one)

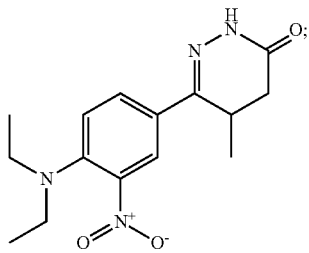 [SMILES: CCN(CC)c1ccc(C2=NNC(=O)CC2C)cc1[N+](=O)[O-]]

and pharmaceutically acceptable salts thereof or a compound of WO2019/025562 such as (6S)-5-[4'-fluoro-2-(trifluoromethyl)biphenyl-4-yl]-6-methyl-3,6-dihydro-2H-1,3,4-oxadiazin-2-one (Compound X), 5-{4-[1-(difluoromethyl)-1H-pyrazol-4-yl]-3-(trifluoromethyl)phenyl}-3,6-dihydro-2H-1,3,4-oxadiazin-2-one, (6S)-5-[4-(2-aminopyridin-4-yl)-3-(trifluoromethyl)phenyl]-6-methyl-3,6-dihydro-2H-1,3,4-oxadiazin-2-one and (6S)-6-methyl-5-{3-(trifluoromethyl)-4-[3-(trifluoromethyl)-1H-pyrazol-1-yl]phenyl}-3,6-dihydro-2H-1,3,4-oxadiazin-2-one or a pharmaceutically acceptable salt thereof.

It will be understood that the modulators described above are known in the art. The structures are provided for illustrative purposes. Any discrepancy between the structure and the known drug will be resolved in favor of the known drug. The PDE3 modulator may be in the form of a pharmaceutically acceptable salt.

It is possible for the PDE3 modulators to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent. For these administration routes, it is possible for the compounds according to the disclosure to be administered in suitable administration forms.

For oral administration, it is possible to formulate the compounds according to the disclosure to dosage forms known in the art that deliver the compounds of the disclosure rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the disclosure in crystalline and/or amorphised and/or dissolved form into the dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation (e.g., powder inhalers, nebulizers), nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

Diagnostics

The present disclosure features diagnostic assays for the characterization of cancer. Levels of AIP and/or TRRAP, particularly in connection with levels of PDE3A and/or PDE3B, and levels SLFN12 may be measured in a subject sample and used as an indicator of cancer that is responsive to treatment with a PDE3 modulator. Levels of AIP, TRRAP, PDE3A, PDE3B, or SLFN12 polynucleotides may be measured by standard methods, such as quantitative PCR, Northern Blot, microarray, mass spectrometry, and in situ hybridization. Standard methods may be used to measure levels of AIP, TRRAP, PDE3A, PDE3B, or SLFN12 polypeptides in a biological sample derived from a tumor. Such methods include immunoassay, ELISA, western blotting using an antibody that binds AIP, TRRAP, PDE3A, PDE3B, or SLFN12, and radioimmunoassay. Elevated levels of PDE3A, SLFN12, AIP and/or TRRAP; or PDE3B, SLFN12, AIP and/or TRRAP polynucleotides or polypeptides are considered a positive indicator of a disease, disorder, or condition (e.g., cancer) that is responsive to treatment with a PDE3 modulator.

Types of Biological Samples

In characterizing the responsiveness of a malignancy in a subject to modulation to induce complex formation treatment, the level of AIP, TRRAP, PDE3A, PDE3B, and/or SLFN12 expression is measured in different types of biologic samples. In one embodiment, the biologic sample is a tumor sample.

In most embodiments, PDE3A and SLFN12 or PDE3B and SLFN12 expression is higher in a sample obtained from a subject that is responsive to PDE3 modulator treatment than the level of expression in a non-responsive subject. In certain implementations, PDE3A, PDE3B, and SLFN12 expression is independently at least about 2, 5, 10, 20, or 30-fold higher in a subject with a malignancy than in a reference condition (e.g., a healthy control). In some embodiments, fold change is determined by calculating the difference in expression of the biomarker (e.g., AIP, TRRAP, PDE3A, PDE3B, SLFN12) in a cancer cell vs the level present in a non-responsive cancer cell or the level present in a corresponding healthy control cell. Additionally, the present disclosure is partially premised on the discovery that PDE3A-SLFN12 or PDE3B-SLFN12 complex formation (and thus apoptosis of cells) occurs when the cells also express AIP. It has also been discovered that TRRAP is required for sensitivity to DNMDP. Accordingly, in addition to increased PDE3A and SLFN12 biomarkers, the cells responsive to complex formation may express no alteration or loss, minimal alteration or loss, or increased expression of AIP and/or TRRAP expression as compared to a reference. For example, the responsive cells may have more than 50% or more than 60% or more than 70% or more than 80% or more than 90% or more than 100% expression of AIP and/or TRRAP as compared to a reference. In certain embodiments, the cell may be considered to not express AIP and/or TRRAP if the number of copies of the biomarker per cellular genome is less than 1 or less than $2^{-1}$ or less than or less than $2^{-2}$ or or less than $2^{-3}$ or less than $2^{-4}$ or less than $2^{-5}$. Conversely, the cell may be considered to express AIP and/or TRRAP if the number of copies of the biomarker per cellular genome is greater than 1 or greater than $2^{-1}$ or greater than or greater than $2^{-2}$ or greater than $2^{-3}$ or greater than $2^{-4}$ or greater than $2^{-5}$. In certain embodiments, the reference is the average expression level of an indicated biomarker (e.g., PDE3A, PDE3B, SLFN12, AIP, TRRAP) in all cell lines for which data is shown in FIG. 5. In various implementations AIP and/or TRAPP is considered to be expressed in a cell if the expression is greater than the the average expression level of the biomarker in all cell lines for which data is shown in FIG. 5 (i.e., the reference for AIP and TRRAP may be the average expression level of the biomarker in all cell lines for which data is shown in FIG. 5). In some embodiments, PDE3A, PDE3B, and/or SLFN12 is considered to have increased expression in a cell if the expression is greater than a healthy control cell (i.e. the reference for PDE3A, PDE3B, and/or SLFN12 may be a healthy control cell). In some embodiments, PDE3A, PDE3B, and/or SLFN12 is considered to have increased expression in a cell if the expression is greater than the average expression levels of the cancer cells in FIG. 5.

Selection of a Treatment Method

As reported herein, subjects suffering from a malignancy may be tested for AIP and/or TRRAP expression in the course of selecting a treatment method or during the treatment method. In some embodiments, patients characterized as having:
 (i) AIP and/or TRRAP expression (e.g. as determined by the average expression level in cancer cells such as that shown in FIG. 5),
 (ii) increased expression of PDE3A or PDE3B relative to a reference (e.g., a healthy cell, a value determined from the average expression level from a healthy sample population, as determined by the average expression level in cancer cells such as that shown in FIG. 5), and
 (iii) increased expression of SLFN12 relative to a reference (e.g., a healthy cell, a value determined from the average expression level from a healthy sample population, a value determined from the average expression level in cancer cells for example as determined from the cells measured in FIG. 5);
are identified as responsive to complex formation and PDE3 modulator treatment. For example, those patients characterized as having:
 (i) AIP and TRRAP expression (e.g. as determined by the average expression level in cancer cells such as that shown in FIG. 5),
 (ii) increased expression of PDE3A or PDE3B relative to a reference (e.g., a healthy cell, a value determined from the average expression level from a healthy sample population, a value determined from the average expression level in cancer cells for example as determined from the cells measured in FIG. 5), and
 (iii) increased expression of SLFN12 relative to a reference (e.g., a healthy cell, a value determined from the average expression level from a healthy sample population, a value determined from the average expression level in cancer cells for example as determined from the cells measured in FIG. 5);
may be identified as responsive to complex formation and PDE3 modulator treatment. In certain implementations, patients characterized as having:
 (i) AIP and/or TRRAP expression (e.g. as determined by the average expression level in cancer cells such as that shown in FIG. 5),
 (ii) increased expression of PDE3A relative to a reference (e.g., a healthy cell, a value determined from the average expression level from a healthy sample population, a value determined from the average expression level in cancer cells for example as determined from the cells measured in FIG. 5), and
 (iii) increased expression of SLFN12 relative to a reference (e.g., a healthy cell, a value determined from the average expression level from a healthy sample population, a value determined from the average expression level in cancer cells for example as determined from the cells measured in FIG. 5);
are identified as responsive to complex formation and PDE3 modulator (e.g., PDE3A modulator, PDE3B modulator) treatment. Those patients characterized as having:
 (i) AIP and TRRAP expression (e.g. as determined by the average expression level in cancer cells such as that shown in FIG. 5),
 (ii) increased expression of PDE3A relative to a reference (e.g., a value determined from the average expression level from a healthy sample population, a value determined from the average expression level in cancer cells for example as determined from the cells measured in FIG. 5), and
 (iii) increased expression of SLFN12 relative to a reference;
may be identified as responsive to complex formation and PDE3 modulator (e.g., PDE3A modulator, PDE3B modulator) treatment. In various implementations, patients characterized as having:
 (i) AIP and/or TRRAP expression,
 (ii) increased expression of PDE3B relative to a reference, and
 (iii) increased expression of SLFN12 relative to a reference;
are identified as responsive to complex formation and PDE3 modulator (e.g., PDE3A modulator, PDE3B modulator) treatment. In some embodiments, patients characterized as having:
 (i) AIP and TRRAP expression (e.g. as determined by the average expression level in cancer cells such as that shown in FIG. 5),
 (ii) increased expression of PDE3B relative to a reference (e.g., a value determined from the average expression level from a healthy sample population, as determined by the average expression level in cancer cells such as that shown in FIG. 5), and (iii) increased expression of SLFN12 relative to a reference (e.g., a value determined from the average expression level from a healthy sample population, as determined by the average expression level in cancer cells such as that shown in FIG. 5);

are identified as responsive to complex formation and PDE3 modulator (e.g., PDE3A modulator, PDE3B modulator) treatment.

In certain embodiments for the selection of treatment methods described above the reference is the average expression level of all cell lines for which data is shown in FIG. 5.

In certain embodiments, the disclosure provides a method for identifying a subject having cancer responsive to treatment with a PDE3 modulator, particularly a compound of WO2019/025562, hereby incorporated by reference in its entirety and specifically in relation to compounds of formula (I) such as those on page 49, line 35-page 75, line 11. In various implementations, the PDE3 modulator may be selected from (6S)-5-[4'-fluoro-2-(trifluoromethyl)biphenyl-4-yl]-6-methyl-3,6-dihydro-2H-1,3,4-oxadiazin-2-one, 5-{4-[1-(difluoromethyl)-1H-pyrazol-4-yl]-3-(trifluoromethyl)phenyl}-3,6-dihydro-2H-1,3,4-oxadiazin-2-one, (6S)-5-[4-(2-aminopyridin-4-yl)-3-(trifluoromethyl)phenyl]-6-methyl-3,6-dihydro-2H-1,3,4-oxadiazin-2-one and (6S)-6-methyl-5-{3-(trifluoromethyl)-4-[3-(trifluoromethyl)-1H-pyrazol-1-yl]phenyl}-3,6-dihydro-2H-1,3,4-oxadiazin-2-one or a salt thereof, the method comprising determining a) AIP and TRRAP expression, b) increased expression of PDE3A or PDE3B relative to a reference (e.g., the level present in a corresponding healthy/control cell or the average expression level of cancer cell lines such as those illustrated in FIG. 5), and c) increased expression of SLFN12 relative to a reference (e.g., the level present in a corresponding healthy/control cell or the average expression level of cancer cell lines such as those illustrated in FIG. 5);

in a sample; thereby identifying the subject as having a cancer responsive to treatment with a PDE3 modulator.

In certain embodiments, the method above can be used to identify a subject as having a cancer that is less likely to respond to treatment comprising a PDE3 modulator mentioned herein the method comprising:

a) determining AIP and/or TRRAP expression, PDE3a or PDE3B expression and SLFN12 expression in a sample from said subject and b) identifying the subject as being less likely to respond to treatment comprising a PDE3 modulator when AIP and/or TRRAP are absent.

The present disclosure also relates to the use of AIP for stratifying in vitro a cancer patient or a sample from a cancer patient disposed to respond treatment with a PDE3 modulator mentioned herein.

The use of a capture reagent, such as an antibody, that binds to or interacts with AIP for stratifying in vitro a cancer patient or sample from a cancer patient disposed to respond to a PDE3 modulator treatment mentioned herein is contemplated within the present disclosure.

The use of a capture reagent that binds to or interacts with TRRAP for stratifying in vitro a cancer patient or sample from a cancer patient disposed to respond to a PDE3 modulator treatment mentioned herein is contemplated within the present disclosure as well.

The use of a capture reagent that binds to or interacts with SLFN12 for stratifying in vitro a cancer patient or sample from a cancer patient disposed to respond to a PDE3 modulator treatment mentioned herein is contemplated within the present disclosure as well.

The use of a PDE3 modulator mentioned herein for the treatment of cancer in a subject characterized by the expression of AIP, TRRAP and increased expression of PDE3A or PDE3B and SLFN12 is contemplated within the present disclosure as well.

The cells identified as being responsive to complex formation (e.g., as chemically induced by PDE3 modulation) may be hyperproliferative cells related to a hyperproliferative disease, disorder, or condition. Such identification may be used in the treatment and/or prevention of various hyperproliferative diseases, disorders, or conditions, such as a myeloproliferative disorder or cancer. In specific embodiments, the cell may be a cancer cell. In some implementations, the may be a cancer cell selected from bladder-, brain-, breast-, cervical-, colorectal-, endometrial-, esophageal-, gallbladder-, gastric-, glioblastoma-, kidney-, leukemia- (e.g., acute myelogenous leukemia-, chronic myelogenous leukemia-, chronic lymphocytic leukemia-), liver- (e.g., hepatocellular carcinoma-, intrahepatic cholangiocarcinoma-, angiosarcoma-, hemangiosarcoma-, hepatoblastoma-), lung- (e.g., non-small cell lung cancer-, small cell lung cancer-, mesothelioma-), melanoma-, ovarian-, pancreatic-, prostate-, multiple myeloma-, sarcoma- (e.g., osteosarcoma-, soft-tissue sacrcoma-), thyroid-, urinary tract-, uterine cancer cells. In certain implementations the cell may be a hematopoietic cancer cell, such as acute lymphoblastic leukemia-, acute myelogenous leukemia-, chronic lymphocytic leukemia-, chronic myelogenous leukemia-, acute monocytic leukemia-, Hodgkin's lymphoma-, or non-Hodgkin's lymphoma cells. Other hyperproliferative disease, disorder, or conditions considered within the scope of the disclosure include myeloproliferative diseases, such as essential thromobocytosis.

Kits

The disclosure provides kits for characterizing the responsiveness of a subject to complex formation and PDE3 modulator treatment.

In certain embodiments, the kit may include a therapeutic composition containing an effective amount of a PDE3 modulator (e.g., PDE3A modulator, PDE3B modulator) in unit dosage form.

In certain implementations, a diagnostic kit of the disclosure provides one or more reagents for measuring expression of AIP, TRRAP, PDE3A, PDE3B, SLFN12, and combinations thereof. Such reagents include one or more capture molecules (e.g., antibodies that recognize a polypeptide selected from AIP, TRRAP, PDE3A, PDE3B or SLFN12). In some embodiments, the kit comprises a reagent for measuring the expression of AIP, a reagent for measuring the expression of PDE3A, and a reagent for measuring the expression of SLFN12. In some embodiments, the kit comprises a reagent for measuring the expression AIP, a reagent for measuring the expression of PDE3B, and a reagent for measuring the expression of SLFN12. In some embodiments, the kit comprises a reagent for measuring the expression of TRRAP, a reagent for measuring the expression of PDE3A, and a reagent for measuring the expression of SLFN12. In some embodiments, the kit comprises a reagent for measuring the expression TRRAP, a reagent for measuring the expression of PDE3B, and a reagent for measuring the expression of SLFN12. In some embodiments, the kit comprises a reagent for measuring the expression of AIP, a reagent for measuring the expression of TRRAP, a reagent for measuring the expression of PDE3A, and a reagent for measuring the expression of SLFN12. In some embodiments, the kit comprises a reagent for measuring the expression AIP, a reagent for measuring the expression of TRRAP, a reagent for measuring the expression of PDE3B, and a reagent for measuring the expression of SLFN12. In some embodiments, the kit comprises a reagent for measuring the expression AIP, a reagent for measuring the expression of TRRAP, a reagent for measuring the expression of PDE3A, a reagent for measuring the expression of PDE3B, and a reagent for measuring the expression of SLFN12.

In some embodiments the kit comprises a PDE3 modulator mentioned herein together with reagents for measurement of expression of AIP, TRRAP, PDE3A or PDE3B, and SLFN12.

The kit may comprise a sterile container which contains a therapeutic or diagnostic composition-such containers can be boxes, ampoules, bottles, vials, tubes, bags, pouches, blister-packs, or other suitable container forms known in the art. In certain implementations, the container may be made of plastic, glass, laminated paper, metal foil, or other materials suitable for holding medicaments. If desired, the kit further comprises instructions for measuring biomarker (e.g., PDE3A, PDE3B, SLFN12, TRRAP, AIP) expression and/or instructions for administering the PDE3 modulator to a subject having a malignancy, e.g., a malignancy selected as responsive to PDE3A modulator treatment. In particular embodiments, the instructions include at least one of the following: description of the therapeutic agent; dosage schedule and administration for treatment or prevention of malignancy or symptoms thereof, precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present disclosure employs, unless otherwise indicated, conventional techniques of molecular biology (including recombinant techniques), microbiology, cell biology, biochemistry and immunology, which are well within the purview of the skilled artisan. These techniques are applicable to the production of the polynucleotides and polypeptides of the disclosure, and, as such, may be considered in making and practicing the disclosure. Particularly useful techniques for particular embodiments will be discussed in the sections that follow.

The following examples are put forth so as to provide those of ordinary skill in the art with a complete disclosure and description of how to make and use the assay, screening, and therapeutic methods of the disclosure, and are not intended to limit the scope of what the inventors regard as their disclosure.

EXAMPLES

The following examples illustrate specific aspects of the instant description. The examples should not be construed as limiting, as the example merely provides specific understanding and practice of the embodiments and its various aspects.

Example 1: Profiling for Sensitivity to PDE3A Modulation

To measure cancer cell death in response to 6-(4-(diethylamino)-3-nitrophenyl)-5-methyl-4,5-dihydropyridazin-3 (2H)-one (DN/DP) treatment, cells were plated in 384w assay plates at the following cell density per well: 500 cells of HeLa (DMEM), A2058 (DMEM), HMCB (EMEM), IGR37 (DMEM), NCIH1734 (RPMI), 750 cells of CAL51 (DMEM), COL0741 (RPMI), DKMG (RPMI), GB1 (EMEM), HEL (RPMI), HEL9217 (RPMI), JHUEM1 (DMEM+F12), L3.3 (RPMI) and TE4 (RPMI), HCC15 (RPMI), UACC257 (RPMI), 1000 cells for HUT78 (IMEM), NCIH1563 (RPMI), NCIH2122 (RPMI), NCIH2172 (RPMI), RVH421 (RPMI) and SKMEL3 (McCoy's 5A), 1500 cells for C32 (EMEM), HS578T (DMEM) and JHOM1 (DMEM+F12). Cells were incubated at 37° C. overnight and then treated with a DNMDP dose dilution series using an HP D300 digital dispenser. After 72 hours, the viability of cells in each well were measured by Cell Titer Glo (Promega G755B and G756B). Percent viability values were determined using the values from untreated wells and AUC values were calculated using a 4-parameter fit. DNMDP was purchased from Life Chemicals (F1638-0042) and trequinsin was purchased from Sigma-Aldrich (T2057).

1400 cells per well were seeded in a 96 well plate in media that had been centrifuged at 500×g for 5 min to remove particulates. The next day, the red fluorescent DNA-staining dye, Incucyte Nuclite Rapid Red, and green fluorescent apoptosis dye, Incucyte Caspase-3/7 Green Apoptosis Reagent (Essen Biosciences), were added in 2 µl FBS to a final concentration of 1:1000 and 1:1500, respectively. Two hours later, [2 µM DNMDP+0.2% DMSO] or 0.2% DMSO was added. Because even sensitive cells sometimes divided before 24 hours, cells were tracked starting at 24 hours, although cells that apoptosed before 24 hours were also counted. For the washout study, the media was removed from DNMDP treated cells at 72 h, the cells were rinsed with media, and incubation was continued in the absence of DNMDP. Cells were tracked starting at 72 h. Images were taken every 1 h up to 96 h, and every 2 h thereafter, with an Incucyte S3 machine (Essen Biosciences). Three channels were recorded: phase contrast, red fluorescence (DNA), and green fluorescence (apoptosis). For cell tracking, a movie superimposing all three channels was analyzed. To avoid effects due to depletion of media components over time, cells were followed up to the last hour before DMSO control cells started to show slowed division or increased apoptosis (136 h for HeLa, 194 h for SKMEL3, 160 h for GB1, 130 h for TE4, 130 h for A2058, 144 h for DKMG, 106 h for HS578T, 186 h for H2172, 220 h for C32).

Melanoma cell lines were tested for sensitivity to DNMDP and the biomarkers of these cells were identified. Biomarker expression thresholds were optimized for positive predictive value and sensitivity. Of the 49 melanoma cell lines tested, seven expressed elevated levels of PDE3A and SLFN12 and one expressed elevated levels of the related protein PDE3B. FIG. 1 compares the reads per kilobase of transcript per million mapped reads (RKPM) for PDE3A and SLFN12 across hundreds of cancer cell lines and identifies the biomarker positive cell lines. Table 1 illustrates the biomarker expression and DNMDP response for 7 melanoma cell lines among the biomarker-positive cell lines in FIG. 1. The eighth sensitive melanoma cell line, RVH421, expressed elevated levels of the related protein, PDE3B. In Table 1, the biomarker mRNA levels expressed as $\log_2$ (RPKM+1) and the area under the curve (AUC) is calculated on a scale from 0-4. Previous analysis of sensitivity data defined the positive predictive value (PPV) of the combined SLFN12/PDE3A biomarker to be about 50%, but the optimized biomarker thresholds result in a PPV of 62%, with sensitive defined by an AUC of less than 2.8, equivalent to an AUC of 1.6 on a scale of 0-4.

TABLE 1

| Cell Line | Lineage | PDE3A expression | PDE3B expression | SLFN12 expression | AUC |
|---|---|---|---|---|---|
| HeLa | cervical | 5.65 | 1.68 | 2.85 | 0.36 |
| IGR37 | melanoma | 5.29 | 1.18 | 2.50 | 1.17 |
| COLO741 | melanoma | 4.30 | 1.20 | 2.41 | 1.19 |
| SKMEL3 | melanoma | 2.69 | 1.28 | 2.96 | 1.74 |
| HMCB | melanoma | 3.82 | 1.72 | 2.09 | 1.85 |
| A2058 | melanoma | 4.64 | 1.32 | 2.02 | 2.11 |
| C32 | melanoma | 2.97 | 1.32 | 3.37 | 3.13 |
| UACC257 | melanoma | 4.90 | 1.95 | 2.39 | 4.00 |
| RVH421 | melanoma | 0.16 | 2.66 | 2.16 | 3.02 |

Figure 2A:
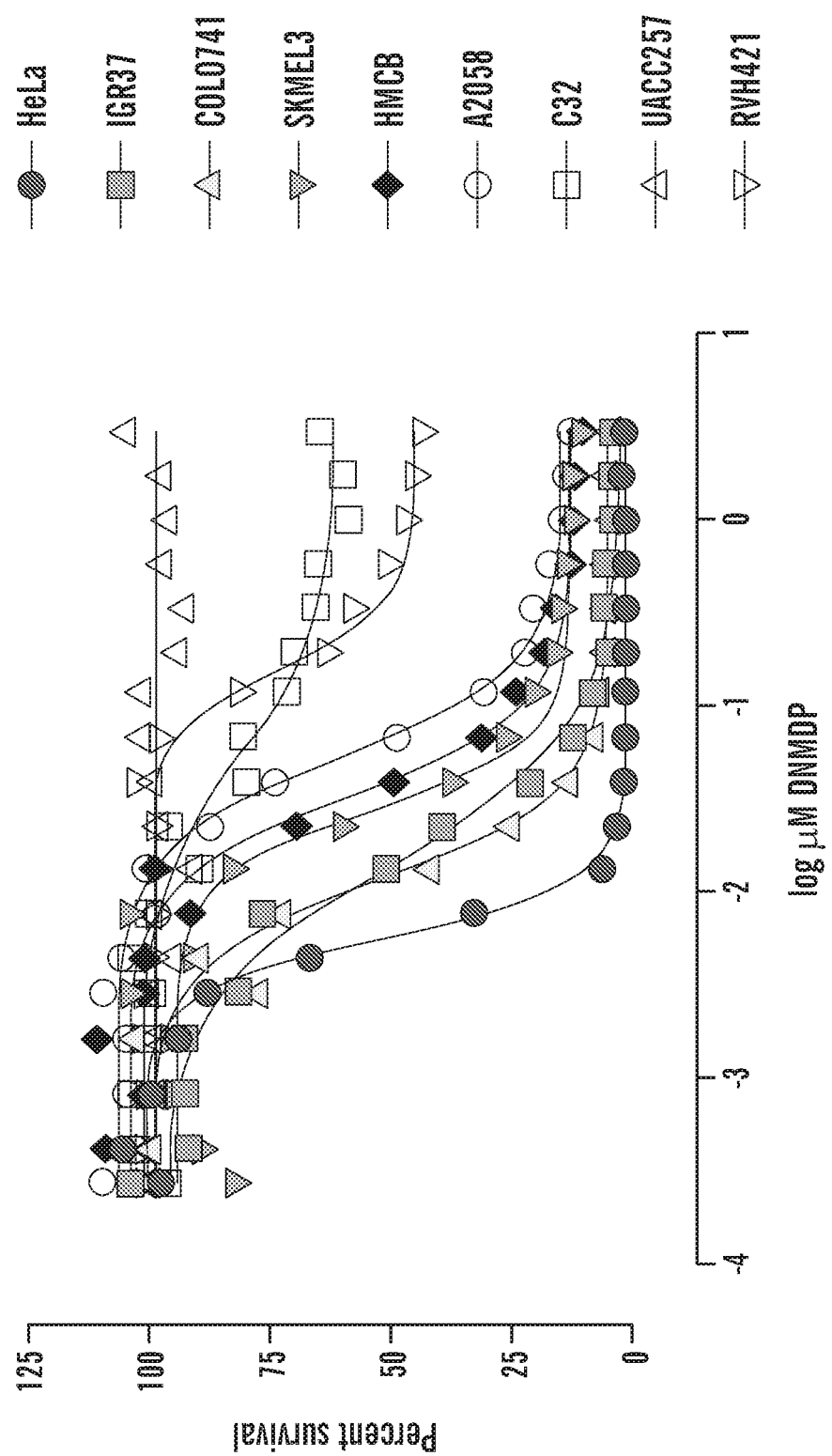
FIG. 2A shows DNMDP 72 h Cell Titer-Glo assay dose response curves for HeLa cells and the 7 melanoma cell lines showing DNMDP sensitivity. As can be seen, C32 and RVH421 are only partially sensitive.
Figure 2B:
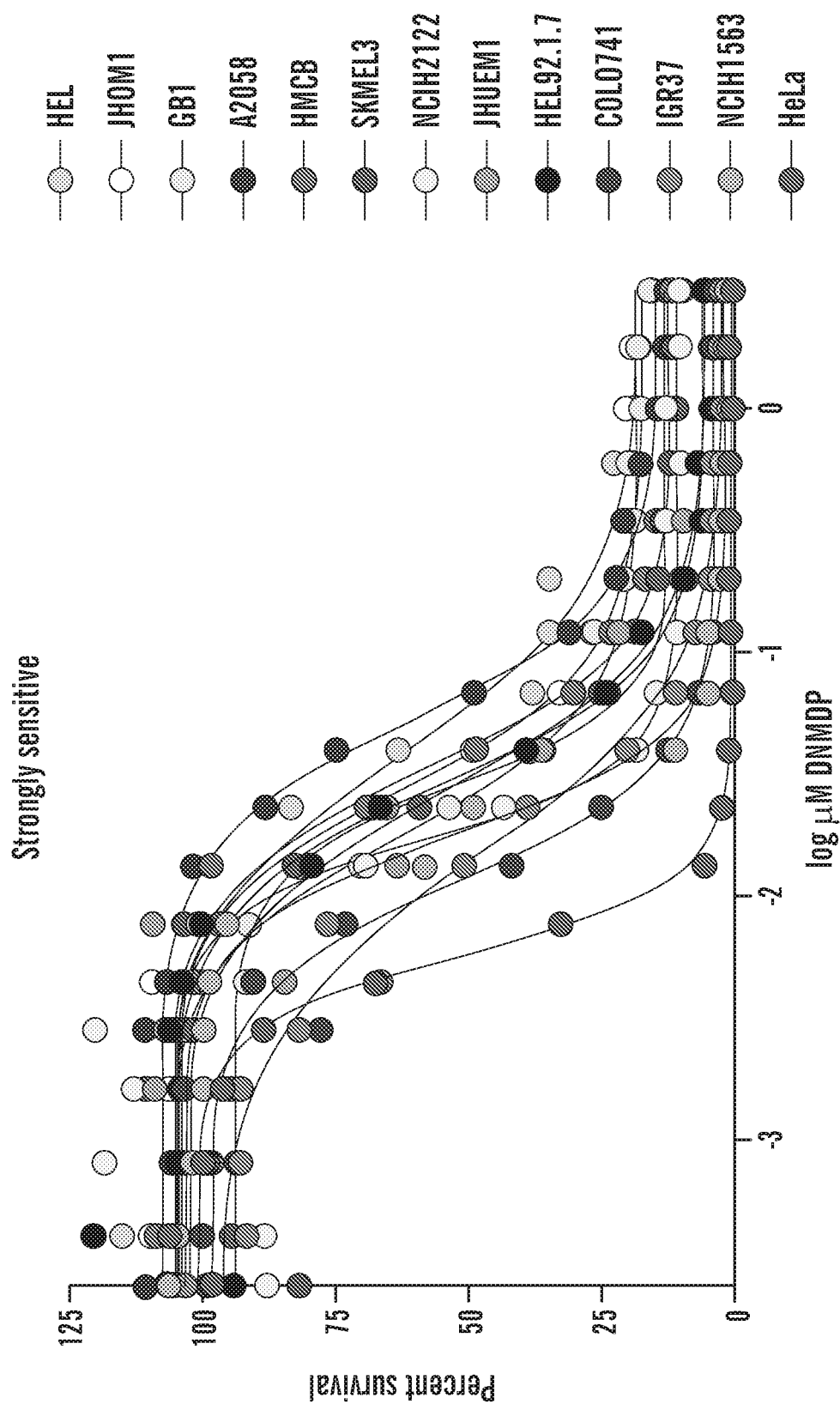
FIG. 2B shows DNMDP 72 h Cell Titer-Glo assay dose response curves for several cell lines sensitive to DNMDP treatment.
Figure 2C:
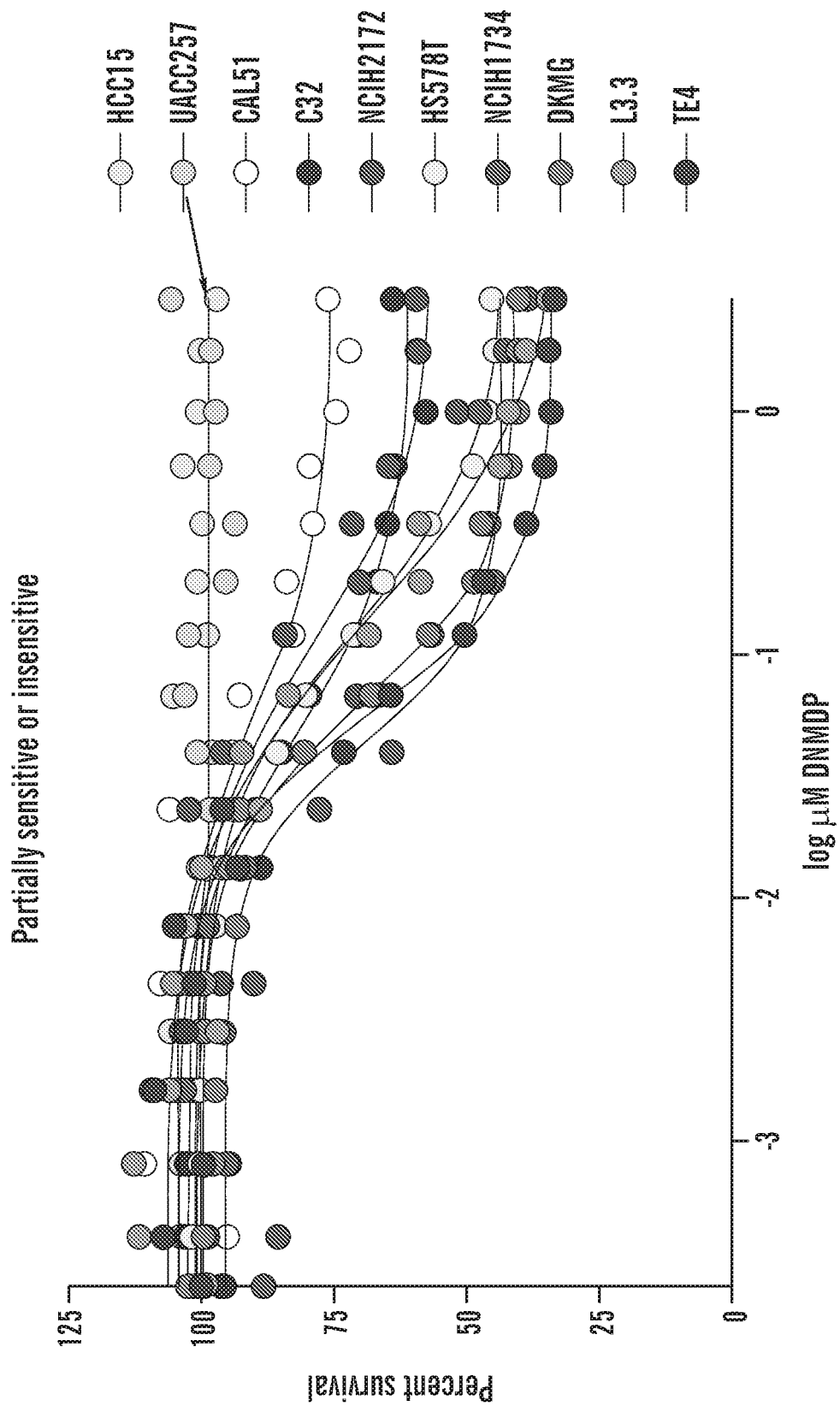
FIG. 2C shows DNMDP 72 h Cell Titer-Glo assay dose response curves for several cell lines partially sensitive or insensitive to DNMDP treatment.

All but one of these eight melanoma cell lines were sensitive to DNMDP. FIG. 2A illustrates the dose response of Cell Titer-Glo assay measurements on these eight cell lines with administration of DNMDP, whereas FIGS. 2B and 2C illustrate the response of all tested PDE3A/SLFN12 biomarker-positive cell lines from multiple disease indications (RVH421 is PDE3B/SLFN12 biomarker-positive). As can be seen in FIG. 2A, C32 and RVH421 are only partially sensitive, and UACC257 cells are completely insensitive. Further experimentation has linked the UACC257 insensitivity to its lack of AIP expression (see, e.g., Example 3). Additionally, it can be seen that sensitivity is not binary; rather dose response curves showed a continuous gradient of inhibition. Based on maximum viability values, the tested cell lines could be split into strongly sensitive cell lines (13 cell lines with <25% maximum viability, FIG. 2B), partially sensitive lines (7 cell lines with 25-75% maximum viability; FIG. 2C), and insensitive cell lines (2 cell; lines with 100% maximal viability; FIG. 2C).

Example 2: CRISPR Knockout

PDE3A CRISPR KO cells (sgRNA #2) were generated according to de Waal et al, 2016 (2), hereby incorporated by reference in its entirety. CRISPR target sites for PDE3B and AIP were identified using the CHOPCHOP CRISPR Design Tool (chopchop.cbu.uib.no). For cloning of sgRNAs, forward and reverse oligos were annealed, phosphorylated and ligated into a BsmBI-digested lentiCRISPRv2 vector. Lentivirus carrying each guide construct was packaged as described above and used to infect target cells. Transduced target cells were selected using 1 µg/ml puromycin and passaged for 7 days before use.

Figure 3A:
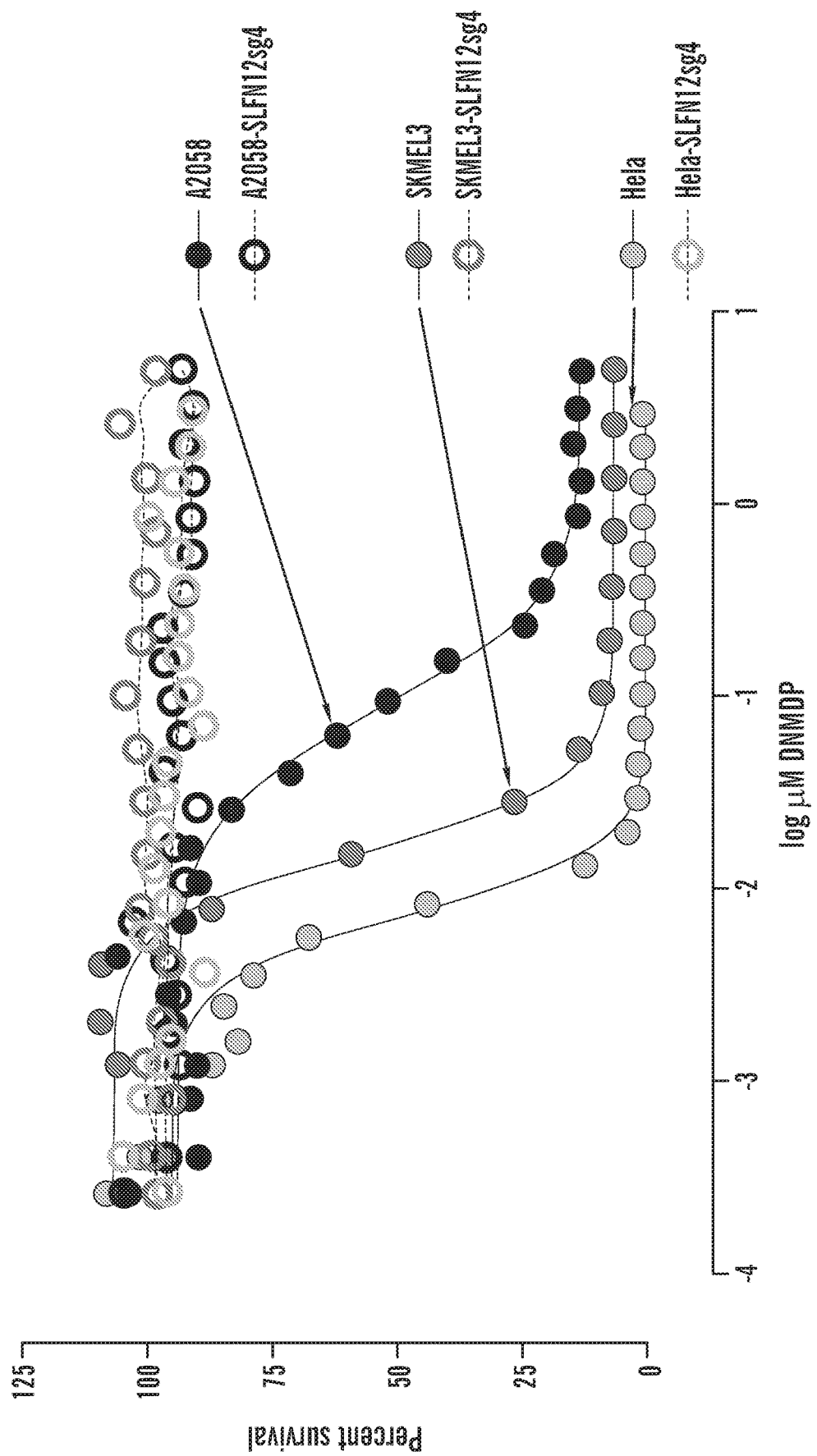
FIG. 3A shows the survival of cells as compared to cells with CRISPR KO of SLFN12 following at various DNMDP concentrations. A2058 and SKMEL3 are representative melanoma cell lines. Survival is measured with a 72 h Cell Titer-Glo assay and CRISPR was performed with sg4, SLFN12 CRISPR guide RNA #4.
Figure 3B:
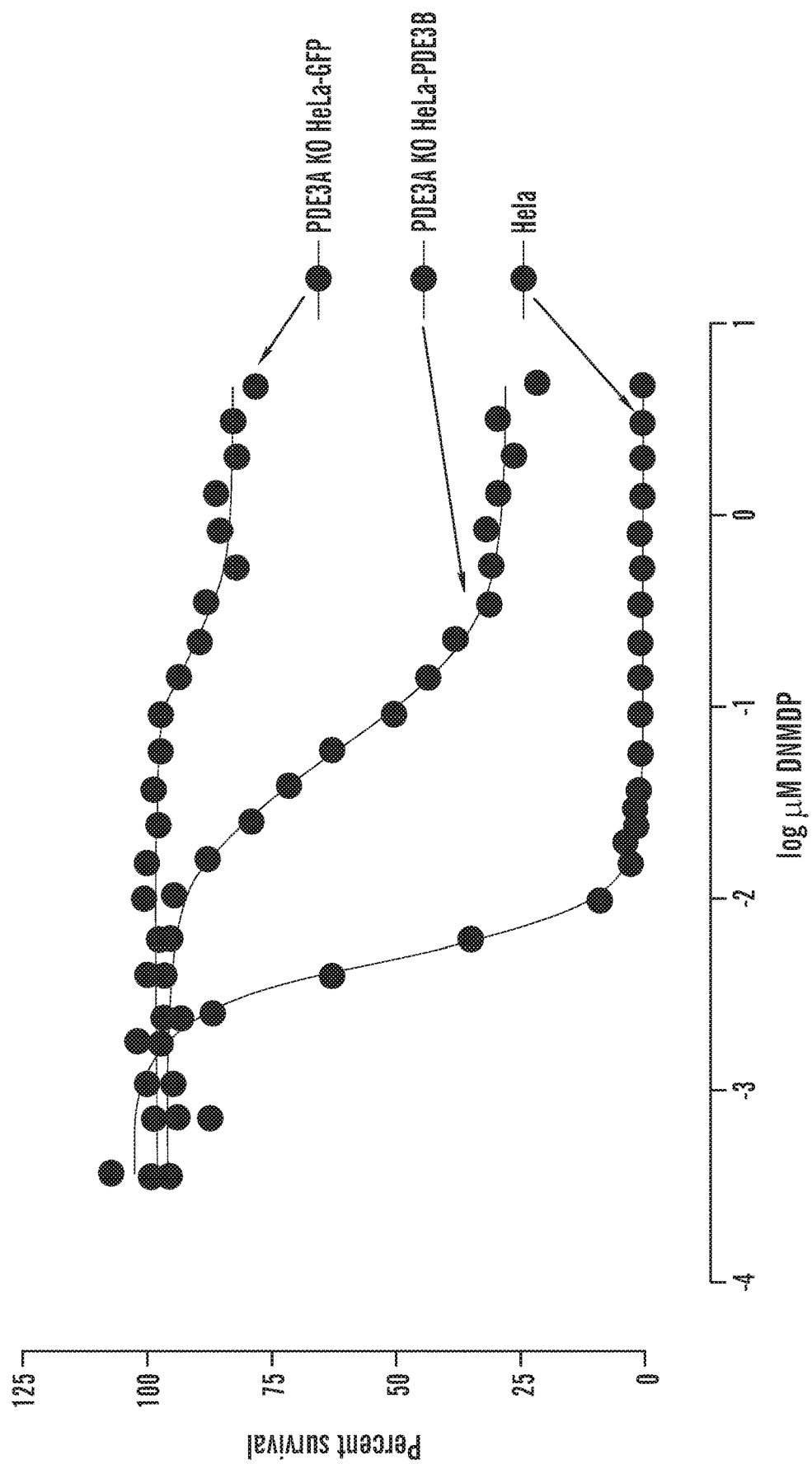
FIG. 3B shows the survival of HeLa cells as compared to PDE3A knockout cells (with and without ectopic PDE3B expression).

FIG. 3A illustrates the survival of cells in the presence of DNMDP that have had CRISPR knockout of SLFN12. FIG. 3B illustrates the survival of cells in the presence of DNMDP that have had CRISPR knockout of PDE3A (with and without ectopic expression of PDE3B). As can be seen, SLFN12 knockout abrogates all measured sensitivity to PDE3 modulators. Moreover, PDE3B can support DNMDP sensitivity in the absence of PDE3A expression, and ectopic expression of PDE3B can furthermore support DNMDP sensitivity in PDE3A knockout HeLa cells. The survival in FIGS. 3A and 3B was measured with a 72 h Cell Titer-Glo assay and CRISPR was performed with sg4, SLNF12 CRISPR guide RNA #4.

In a genome wide CRISPR screen, genes were identified as important for cancer cell killing in HeLa cells. The Brunello CRISPR library was used for the DNMDP resistance screen. Lentiviral infection was carried out in duplicate and for each replicate with enough HeLa cells to achieve >1000 infected cells per library member (80000 sgRNAs, >8×10$^7$ cells total) and at low multiplicity of infection (MOI) to achieve transduction of a single sgRNA per cell. Infection efficiencies for the two replicates were 24% and 31% respectively, corresponding to a MOI of about 0.3, meaning about 85% of infected cells would be predicted to have single sgRNA integration. At the time of infection, HeLa cells were resuspended in media and mixed with Brunello library virus in the presence of 8 µg/ml polybrene (library lentivirus provided by the Genetic Perturbation Platform at the Broad Institute), plated in 12 well dishes at 3×10$^6$ cells per well, and spun at 931×g for 2 h at 30° C. 2 h after the spin infection, virus-containing media was removed and fresh media was added for incubation overnight. The day after the infection, cells were trypsinized and pooled into T225 flasks at 50% confluence (1.6×10$^7$ cells per flask) and puromycin was added to 1 µg/ml to select for infected cells. At the same time, in-line infection efficiency assays were performed by comparing cell counts after puromycin selection to those without selection. After 4 days of puromycin selection, infected cells were collected and passaged in T225 flasks at 25% confluence (8×10$^6$ cells per flask) for three additional days to allow CRISPR KO to complete. Cells were collected at 8 days after infection, and 8×10$^7$ cells each were split into DMSO control arm (plating at 8×10$^6$ cells per T225 flask) or 25 nM DNMDP treatment arm (plating at 2×10$^7$ cells per T225 flask). Cells were passaged every 3 to 4 days at 25% confluence for the next 14 days. For the DMSO arm, 8×10$^7$ cells were maintained at every passage, whereas all surviving cells were passaged for the DNMDP arm. After 14 days of compound treatment, cells were harvested, washed with cold PBS and flash frozen at 2×10$^7$ cells (DMSO arm) or less portions for genomic DNA isolation. Genomic DNA was isolated using the Nucleospin Blood XL kit (DMSO samples, 4 preps to cover 8×10$^7$ cells, Machere-Nagel 740950.50) or the QIAamp DNA Blood Mini kit (DNMDP-treated samples, Qiagen 51104). PCR amplification of sgRNA tags and pooled library sequencing were carried out as described in Sanson, et al. "Optimized libraries for CRISPR-Cas9 genetic screens with multiple modalities" Nat Commun 9(1):5416 ("Sanson"), hereby incorporated by reference in its entirety.

CRISPR screen data analysis was done largely as described in Sanson. Briefly, deconvolution of sequencing reads yielded read counts for each sgRNA under each replicate treatment condition. Log 2-Normalized-Reads for each guide per condition was calculated using the formula log 2 (guide/total*1000000+1) and averaged across the two replicates. Subtracting DMSO values from those for 25 nM DNMDP generated Log-Fold-Change values for each sgRNA, which were then averaged across all sgRNAs targeting the same gene to generate gene-level Average-Log-Fold-Change score. To statistically evaluate gene-level enrichment in DNMDP treatment relative to DMSO, sgRNAs were rank ordered based on Average-Log-Fold-Change, and p-values for each sgRNA relative to the rank order were determined by running a hypergeometric distribution without replacement, equivalent to a one-sided Fisher's exact test. The average of the negative log 10 p values for each sgRNA targeting the same gene was calculated to generate the average negative log 10 p-value for each gene. A volcano plot was generated using the average-log 2-fold-change and the average negative log 10 p-value for all genes with 3 to 8 sgRNAs per gene to visualize gene enrichments after the positive selection of 25 nM DNMDP treatment.

AIP, SLFN12, and PDE3A knockout cause the greatest increase in cell survival in the presence of 25 nm DN/DP.

Figure 4:
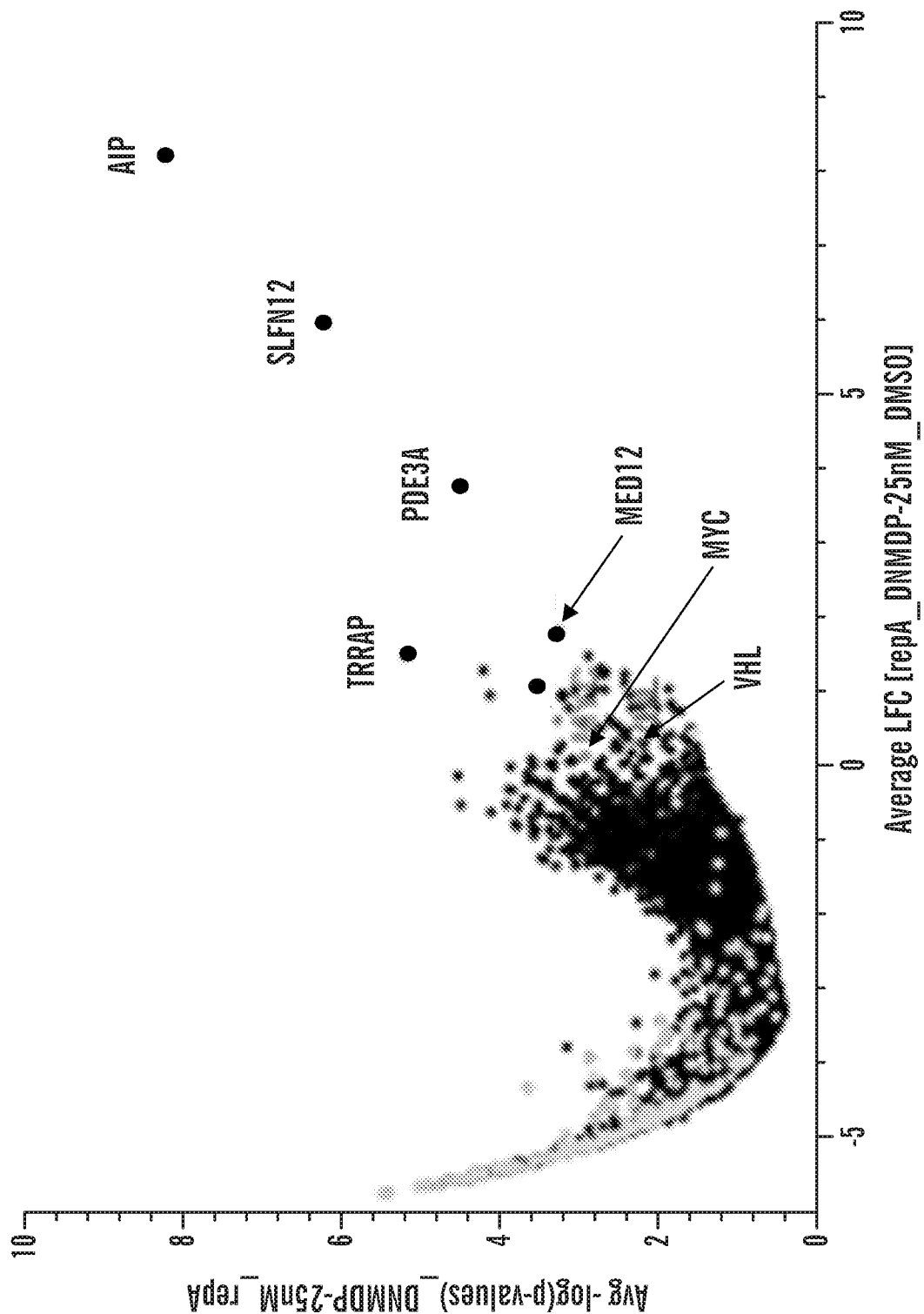
FIG. 4 identifies those CRISPR gene targets resulting in decreased sensitivity for DNMDP cancer cell killing in HeLa cells. AIP, SLFN12, and PDE3A knockout cause the greatest increase in cell survival in the presence of 25 nM DNMDP. The results are plotted as log fold change (LFC) of gene CRISPR guide RNA representation among all genes compared to –log p-values, indicating the likelihood of significance. TRRAP also exhibited a significant increase in cell survival in the presence of 25 nM DNMDP.

FIG. 4 illustrates the results of the CRISPR screen comparing the log fold change (LFC) of gene CRISPR guide representation as compared to −log(p-value) of the screen (each as compared to HeLa cells). The gRNA best supporting survival in the presence of DNMDP was specific for the AIP. As expected, SLFN12 and PDE3A knockout also strongly supported cell survival in the presence of DNMDP, ranking second and third behind AIP, respectively. Knockout of the histone acetyltransferase complex protein, transformation/transcription domain associated protein (TRRAP), exhibited as significant but much weaker phenotype as well.

The CRISPR screen allowed for identification of the aryl hydrocarbon receptor interacting protein as having potent effect on cell survival rates. AIP is a co-chaperone protein that regulates stability and subcellular localization of the aryl hydrocarbon receptor and other proteins, as described in Trivellin, G. and M. Korbonits, *J Endocrinol* 210 (2011): 137-55, hereby incorporated by reference in its entirety. Of the cancer cell lines tested, only a single cancer cell line, UACC257, the biomarker-positive but DNMDP-resistant melanoma cell line lacked AIP expression. This can be seen in FIG. 5 where the x axis is plotted by $\log_2$ copy number, and the y axis by gene expression. As can be seen, UACC257 does not express AIP while the remaining cell lines do.

Figure 6A:
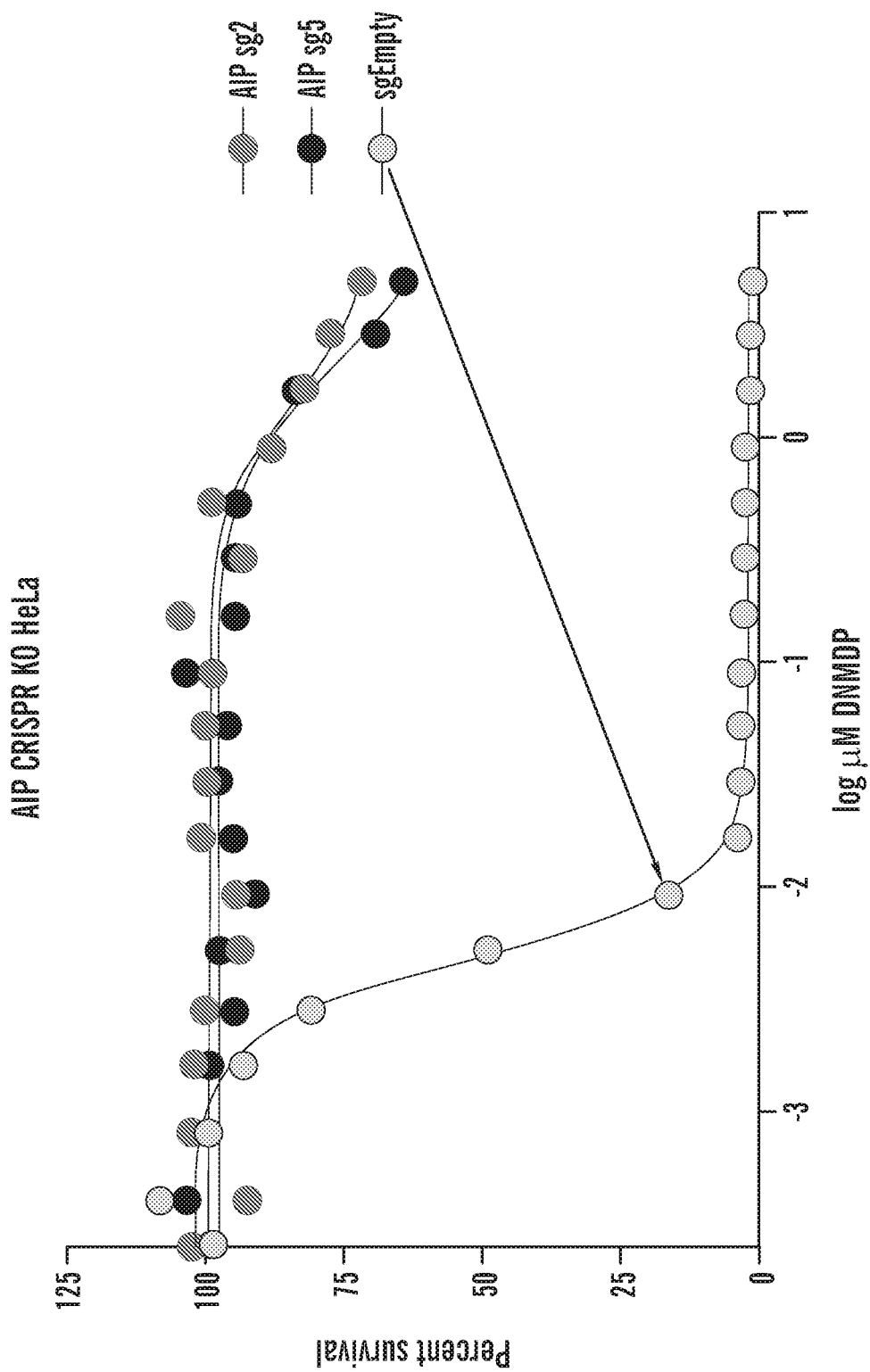
FIG. 6A illustrates the results of the 72-hour Cell Titer-Glo assay with independent AIP CRISPR gRNAs (sg) in HeLa cells.
Figure 6B:
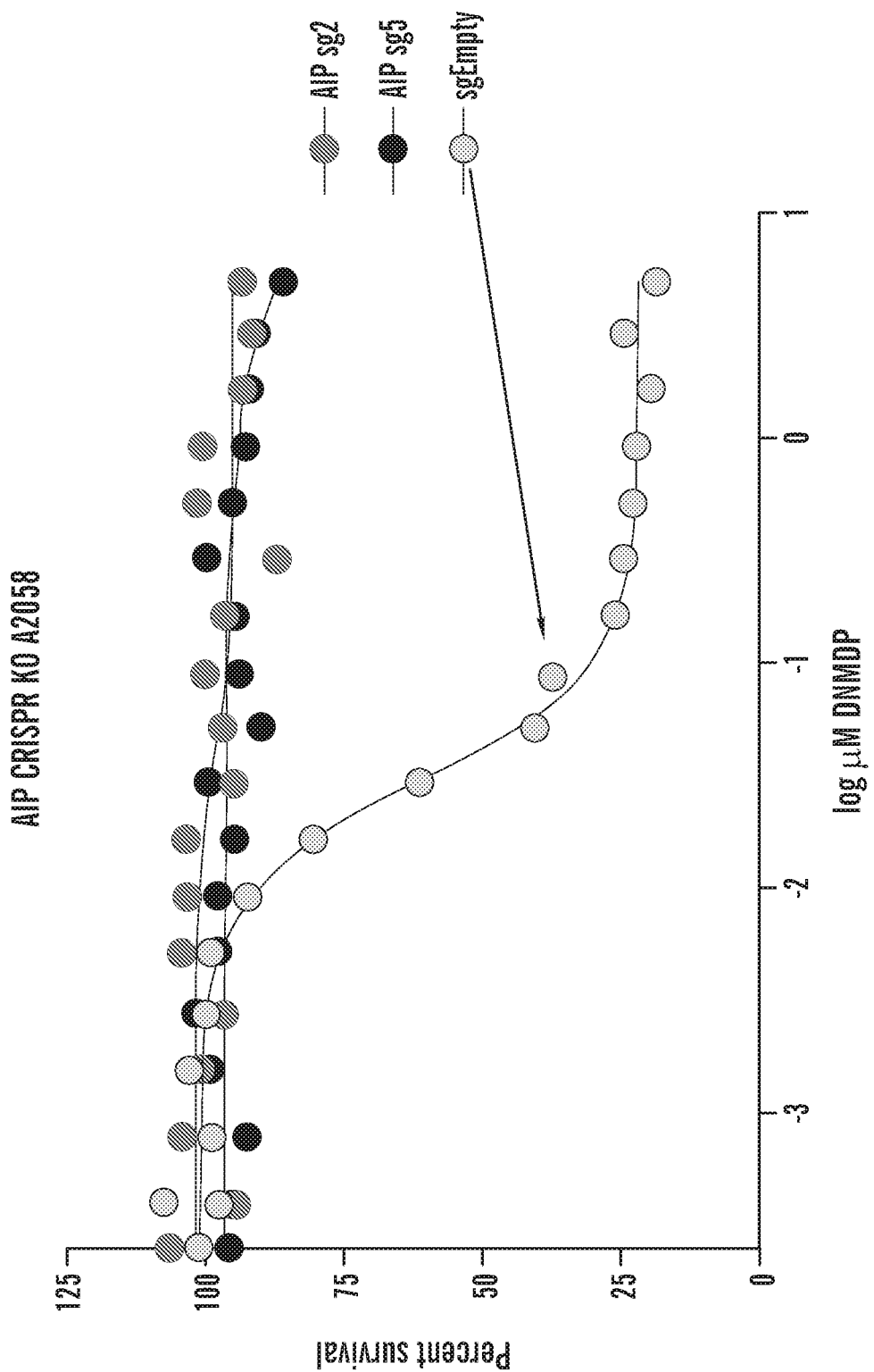
FIG. 6B shows the results of the 72-hour Cell Titer-Glo assay with independent AIP CRISPR gRNAs (sg) in A2058 melanoma cells.
Figure 6C:
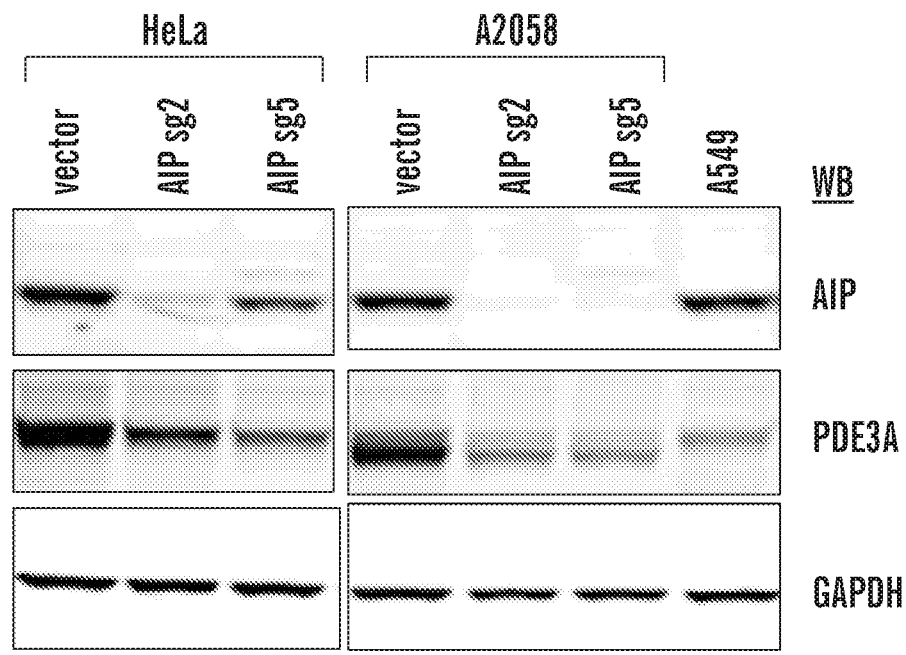
FIG. 6C is an immunoblot revealing that AIP knockout decreases PDE3A protein levels in DNMDP-sensitive cell lines.

Furthermore, that AIP knockout eliminates HeLa cell response to DNMDP was validated with independent gRNAs as shown in FIG. 6A. Similar results were observed upon knockout of AIP from the melanoma cell line A2058 (FIG. 6B). Additionally, AIP knockout in these cell lines resulted in decreased PDE3A protein expression (FIG. 6C).

Example 3: AIP Knockout and Complex Formation

Because decreased PDE3A protein expression could impact DNMDP-induced PDE3A-SLFN12 complex formation, the effects of AIP knockout on this complex formation were also measured. As there is no good antibody for SLFN12 protein, we ectopically expressed V5-tagged SLFN12 in parental or AIP-knockout HeLa cells, immunoprecipitated endogenous PDE3A, and assessed whether V5-SLFN12 could be detected in the immunoprecipitates. Cells were plated in 10 cm petri dishes and collected at 50-90% confluence. For PDE3A immunoblotting in biomarker positive cells and in AIP KO cells, cells were seeded in 15 cm plates at similar density as in viability assays with a vessel scaling factor of 5000, e.g., 500 cells per well was scaled to $10^6$ cells per 10 cm plate or $2.5 \times 10^6$ cells per 15 cm plate, and then cultured for 72 hours before collection. Cell pellets were lysed at 4° C. for 20 minutes in modified RIPA buffer (150 mM NaCl, 10% glycerol, 50 mM Tris-Cl pH 8.0, 50 mM MgCl2, 1% NP-40) supplemented with EDTA-free protease inhibitors (Sigma-Aldrich 4693159001) and PhosSTOP phosphatase inhibitors (Sigma-Aldrich 4906837001). Lysates were clarified by centrifugation at 13,000 rpm×10 min at 4° C. and quantified using BCA protein assays (Thermo Fisher Scientific 23225). Clarified lysates were resolved on 4-12% Bis-Tris PAGE gels, transferred to nitrocellulose membranes (Thermo Fisher Scientific IB23001) and immunoblotted with primary antibodies against PDE3A (Bethyl 302-740A, 1:2000), V5 (Life Technologies R96205 at 1:5,000), AIP (Thermo Fisher Scientific MA3-16515 at 1:2000), Vinculin (Sigma-Aldrich V9264 at 1:5,000), GAPDH (Cell Signaling Technology 2118 at 1:2000) and secondary antibodies from LiCOR Biosciences (92632210 and 926068021, each at 1:10,000). Blots were washed and imaged using a LiCOR Odyssey infrared imager, and fluorescent signals quantified using the Image Studio software provided by the LiCOR manufacturer.

Genomic DNA was isolated from cells using QIAamp DNA mini kit (Qiagen 51304) and SLFN12 genomic region was amplified by PCR using Q5 High-Fidelity 2× Master Mix (New England Biolabs M0492) and primers SLFN12_2_F or SLFN12_428_F and SLFN12_858_R. PCR products were purified using QIAquick PCR Purification Kit (Qiagen 28104) and send for sequencing using Forward or Reverse primers used for PCR. Sequencing reads were aligned to reference sequence using Benchling alignment tools.

Figure 7:
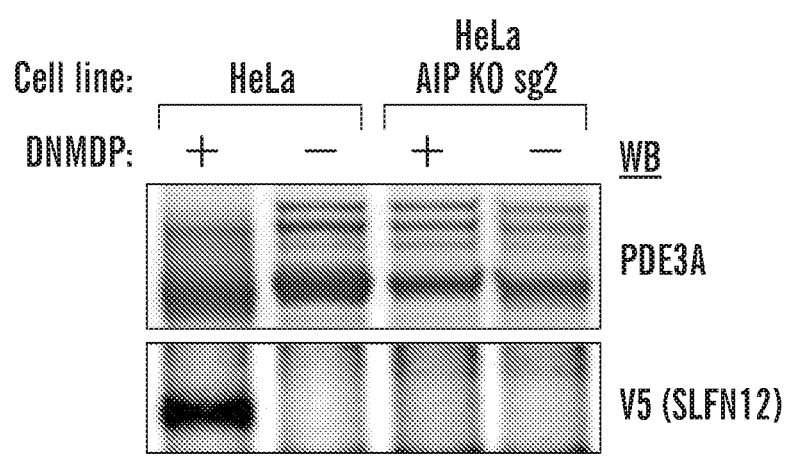
FIG. 7 is an immunoblot illustrating that AIP knockout prevents DMNDP induced complex formation. PDE3A immunoprecipitates from HeLa cells transiently transfected with V5-tagged SLNF12 and treated with 10 µM DNMDP.

AIP knockout completely abolished PDE3A-SLFN12 complex formation in response to DNMDP (FIG. 7), confirming that AIP functions upstream of DNMDP-induced complex formation. The partial decrease in PDE3A protein levels shown in FIG. 6C cannot fully account for the effects of AIP knockout on PDE3A-SLFN12 complex formation. For example, A549 cells, which express sufficient endogenous PDE3A to support partial sensitivity to complex inducing active compounds upon ectopic expression of SLFN12, express similar levels or even less PDE3A than these AIP knockout cells.

Figure 8A:
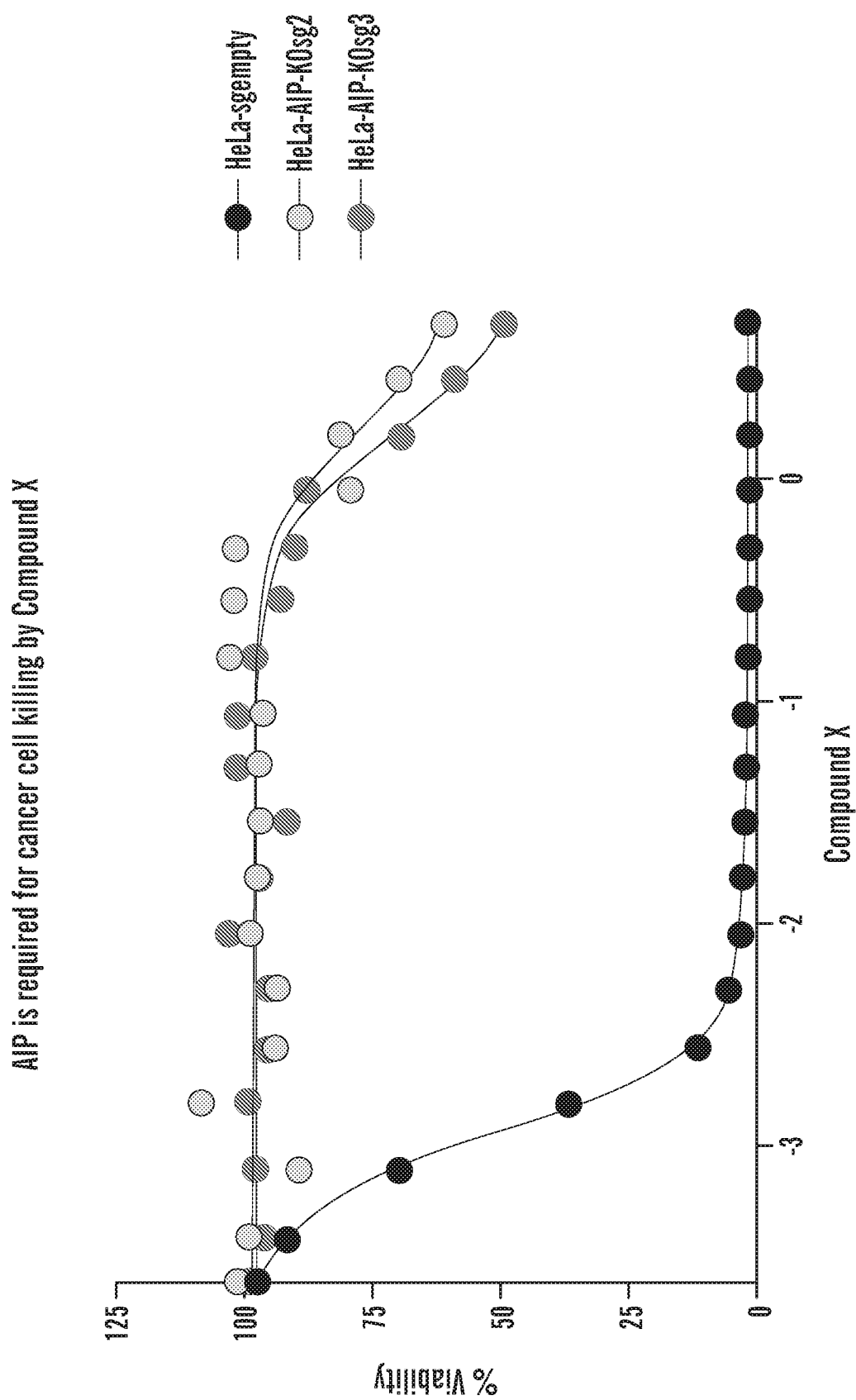
FIG. 8A is a graph and FIG. 8B is an image of an immunoblot. The two figures show that that AIP is necessary for Compound X induced cancer cell killing and induction of the PDE3A-SLFN12 complex.
Figure 8B:
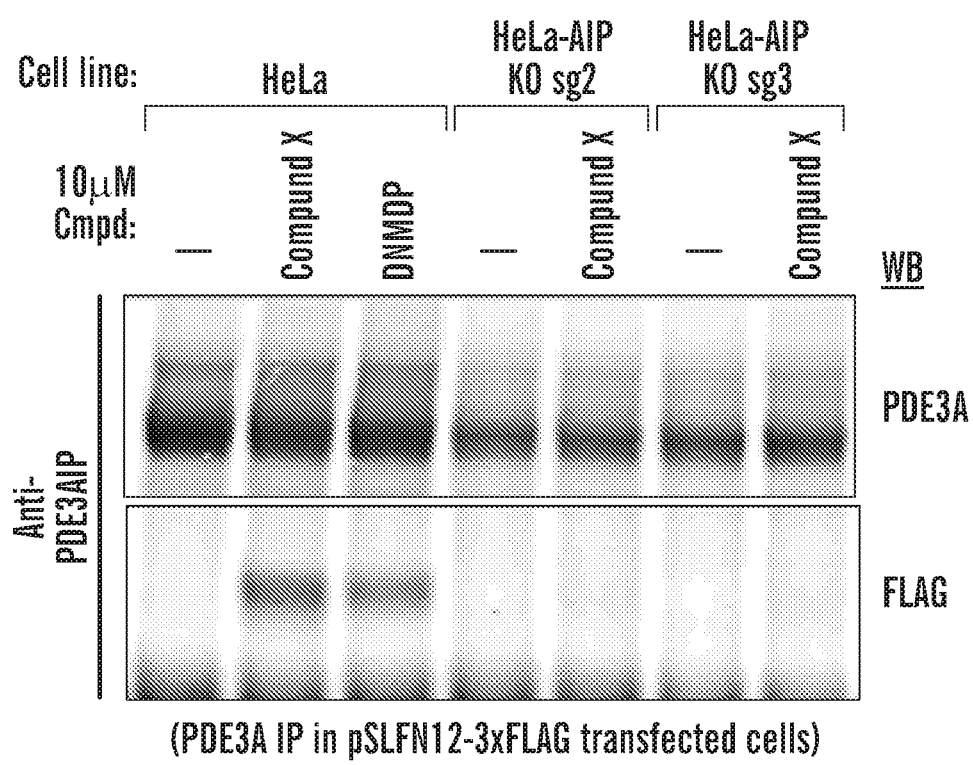

AIP was required for cancer cell killing in response to Compound X (also termed (6S)-5-[4'-fluoro-2-(trifluoromethyl)biphenyl-4-yl]-6-methyl-3, 6-dihydro-2H-1,3,4-oxadiazin-2-one) (FIG. 8A). Cervical cancer cell viability was reduced at increasing concentrations of Compound X (FIG. 8A). Cancer cell killing required AIP, as no cancer cell killing was observed in HeLa cells lacking AIP, i.e., HeLa cells having an AIP knock out. AIP knockout also abolished PDE3A-SLFN12 complex formation in response to treatment with Compound X as shown at FIG. 8B. In FIG. 8B an anti-PDE3A antibody was used to pull down a PDE3A-SLFN12 complex. Complex formation between PDE3A and FLAG-tagged SLFN12 was induced in the presence of Compound X and in the presence of DNMDP. Complex formation was not observed when AIP was knocked out using Crispr (KO sg2, KO sg3). HeLa cells were treated with 10 M DNMDP or 10 μM Compound X. These results indicate that AIP can act as a marker for responsiveness to Compound X.

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications and variances which fall within the scope of the appended claims.

The invention claimed is:

1. A method of killing or reducing the survival of a cell selected as responsive to PDE3A-SLFN12 complex formation or PDE3B-SLFN12 complex formation comprising contacting said cell with a PDE3 modulator, wherein said cell is selected as responsive to said PDE3 modulator when said cell:
   (i) expresses AIP and/or TRRAP polypeptides or polynucleotides,
   (ii) has increased expression of PDE3A and/or PDE3B polypeptides or polynucleotides relative to a reference, and
   (iii) has increased expression of SLFN12 polypeptides or polynucleotides relative to the reference.

2. The method according to claim 1, wherein said cell is selected as responsive to said PDE3 modulator when said cell:
   (i) expresses AIP and TRRAP polypeptides or polynucleotides,
   (ii) has increased expression of PDE3A and/or PDE3B polypeptides or polynucleotides relative to a reference, and
   (iii) has increased expression of SLFN12 polypeptides or polynucleotides relative to the reference.

3. The method according to claim 1, wherein said cell is selected as responsive to said PDE3 modulator when said cell:
   (i) expresses AIP and TRRAP polypeptides or polynucleotides, (ii) has increased expression of PDE3A polypeptides or polynucleotides relative to a reference, and (iii) has increased expression of SLFN12 polypeptides or polynucleotides relative to the reference.

4. The method according to claim 1, wherein said cell is selected as responsive to said PDE3 modulator when said cell:

(i) expresses AIP and TRRAP polypeptides or polynucleotides, (ii) has increased expression of PDE3B polypeptides or polynucleotides relative to a reference, and (iii) has increased expression of SLFN12 polypeptides or polynucleotides relative to the reference.

5. The method of claim 1, wherein the PDE3 modulator is 6-(4-(diethylamino)-3-nitrophenyl)-5-methyl-4,5-dihydropyridazin-3 (2H)-one (DNMDP) or (6S)-5-[4'-fluoro-2-(trifluoromethyl) biphenyl-4-yl]-6-methyl-3,6-dihydro-2H-1,3,4-oxadiazin-2-one (Compound X).

6. The method of claim 1, wherein said PDE3 modulator is administered orally or by intravenous injection.

7. A method for the treatment of a hyperproliferative disease, disorder, or condition in a subject comprising administering to said subject a PDE3 modulator, wherein said subject is identified as having a hyperproliferative disease, disorder, or condition that is responsive to the PDE3 modulator by obtaining one or more cells of the hyperproliferative disease, disorder, or condition from the subject and detecting:

(i) the expression of aryl hydrocarbon receptor interacting protein (AIP) polypeptides or polynucleotides and/or transformation/transcription domain associated protein (TRRAP) polypeptides or polynucleotides in the cell;

(ii) the expression of phosphodiesterase 3A (PDE3A) polypeptides or polynucleotides or the expression of phosphodiesterase 3B (PDE3B) polypeptides or polynucleotides in the cell relative to a reference, and (iii) the expression of Schlafen family member 12 (SLFN12) polypeptides or polynucleotides in the cell relative to the reference;

wherein said hyperproliferative disease, disorder, or condition is characterized as responsive to said complex formation if:

(i) AIP and/or TRRAP are expressed in the cell, (ii) the expression of PDE3A and/or PDE3B is increased relative to the reference, and (iii) the expression of SLFN12 is increased relative to the reference.

8. The method of claim 7, wherein said hyperproliferative disease, disorder, or condition is a myeloproliferative disease.

9. The method of claim 7, wherein said cell is a cancer cell.

10. The method of claim 9, wherein said cancer cell is a melanoma-, endometrium-, lung-, hematopoetic-/lymphoid-, ovarian-, cervical-, soft-tissue-sarcoma-, urinary tract, pancreas-, thyroid-, kidney-, glioma-, glioblastoma-, or breast-cancer cell.

11. The method of claim 9, wherein said cancer cell is a melanoma-, glioma-, glioblastoma-, ovarian-, sarcoma-, acute myeloid leukemia-, or lung adenocarcinoma cell.

12. The method of claim 7, wherein said cell is collected from a tissue sample, a blood sample, or a plasma sample from the subject.

13. The method of claim 7, wherein the PDE3 modulator is 6-(4-(diethylamino)-3-nitrophenyl)-5-methyl-4,5-dihydropyridazin-3 (2H)-one (DNMDP) or (6S)-5-[4'-fluoro-2-(trifluoromethyl) biphenyl-4-yl]-6-methyl-3,6-dihydro-2H-1,3,4-oxadiazin-2-one (Compound X).

* * * * *

SEQUENCE LISTING

<160> NUMBER OF SEQ ID NOS: 11

<210> SEQ ID NO 1
<211> LENGTH: 7319
<212> TYPE: DNA

<213> ORGANISM: Homo sapiens

<400> SEQUENCE: 1

| | | | | | |
|---|---|---|---|---|---|
| gggggccact | gggaattcag | tgaagagggc | accctatacc | atggcagtgc | ccggcgacgc | 60 |
| tgcacgagtc | agggacaagc | ccgtccacag | tggggtgagt | caagccccca | cggcgggccg | 120 |
| ggactgccac | catcgtgcgg | accccgcatc | gccgcgggac | tcgggctgcc | gtggctgctg | 180 |
| gggagacctg | gtgctgcagc | cgctccgag | ctctcggaaa | cttttcctcc g | cgctgtgcgc | 240 |
| gggctccctg | tcctttctgc | tggcgctgct | ggtgaggctg | gtccgcgggg | aggtcggctg | 300 |
| tgacctggag | cagtgtaagg | aggcggcggc | ggcggaggag | gaggaagcag | ccccgggagc | 360 |
| agaaggggc | gtcttcccgg | ggcctcgggg | aggtgctccc | ggggcggtg | cgcggctcag | 420 |
| cccctggctg | cagccctcgg | cgctgctctt | cagtctcctg | tgtgccttct | tctggatggg | 480 |
| cttgtacctc | ctgcgcgccg | gggtgcgcct | gcctctggct | gtcgcgctgc | tggccgcctg | 540 |
| ctgcgggggg | gaagcgctcg | tccagattgg | gctgggcgtc | ggggaggatc | acttactctc | 600 |
| actccccgcc | gcggggtgg | tgctcagctg | cttggccgcc | gcgacatggc | tggtgctgag | 660 |
| gctgaggctg | ggcgtcctca | tgatcgcctt | gactagcgcg | gtcaggaccg | tgtccctcat | 720 |
| ttccttagag | aggttcaagg | tcgcctggag | accttacctg | gcgtacctgg | ccggcgtgct | 780 |
| ggggatcctc | ttggccaggt | acgtggaaca | aatcttgccg | cagtccgcgg | aggcggctcc | 840 |
| aagggagcat | ttgggtccc | agctgattgc | tgggaccaag | gaagatatcc | cggtgtttaa | 900 |
| gaggaggagg | cggtccagct | ccgtcgtgtc | cgccgagatg | tccggctgca | gcagcaagtc | 960 |
| ccatcggagg | acctccctgc | cctgtatacc | gagggaacag | ctcatggggc | attcagaatg | 1020 |
| ggaccacaaa | cgagggccaa | gaggatcaca | gtcttcagga | accagtatta | ctgtggacat | 1080 |
| cgccgtcatg | ggcgaggccc | acggcctcat | taccgacctc | ctggcagacc | cttctcttcc | 1140 |
| accaaacgtg | tgcacatcct | tgagagccgt | gagcaacttg | ctcagcacac | agctcacctt | 1200 |
| ccaggccatt | cacaagccca | gagtgaatcc | cgtcacttcg | ctcagtgaaa | actatacctg | 1260 |
| ttctgactct | gaagagagct | ctgaaaaaga | caagcttgct | attccaaagc | gcctgagaag | 1320 |
| gagtttgcct | cctggcttgt | tgagacgagt | ttcttccact | tggaccacca | ccacctcggc | 1380 |
| cacaggtcta | cccaccttgg | agcctgcacc | agtacggaga | gaccgcagca | ccagcatcaa | 1440 |
| actgcaggaa | gcaccttcat | ccagtcctga | ttccttggaat | aatccagtga | tgatgaccct | 1500 |
| caccaaaagc | agatccttta | cttcatccta | tgctatttct | gcagctaacc | atgtaaaggc | 1560 |
| taaaaagcaa | agtcgaccag | gtgccctcgc | taaaatttca | cctctttcat | cgccctgctc | 1620 |
| ctcacctctc | caagggactc | ctgccagcag | cctggtcagc | aaaatttctg | cagtgcagtt | 1680 |
| tccagaatct | gctgacacaa | ctgccaaaca | aagcctaggt | tctcacaggg | ccttaactta | 1740 |
| cactcagagt | gccccagacc | tatcccctca | aatcctgact | ccacctgtta | tatgtagcag | 1800 |
| ctgtggcaga | ccatattccc | aagggaatcc | tgctgatgag | ccctggaga | gaagtggggt | 1860 |
| agccactcgg | acaccaagta | gaacagatga | cactgctcaa | gttacctctg | attatgaaac | 1920 |
| caataacaac | agtgacagca | gtgacattgt | acagaatgaa | gatgaaacag | agtgcctgag | 1980 |
| agagcctctg | aggaaagcat | cggcttgcag | cacctatgct | cctgagacca | tgatgtttct | 2040 |
| ggacaaacca | attcttgctc | ccgaacctct | tgtcatggat | aacctggact | caattatgga | 2100 |
| gcagctaaat | acttggaatt | ttccaatttt | tgatttagtg | gaaaatatag | gaagaaaatg | 2160 |
| tggccgtatt | cttagtcagg | tatcttacag | acttttttgaa | gacatgggcc | tctttgaagc | 2220 |
| ttttaaaatt | ccaattaggg | aatttatgaa | ttattttcat | gctttggaga | ttggatatag | 2280 |

```
ggatattcct tatcataaca gaatccatgc cactgatgtt ttacatgctg tttggtatct   2340
tactacacag cctattccag gcctctcaac tgtgattaat gatcatggtt caaccagtga   2400
ttcagattct gacagtggat ttacacatgg acatatggga tatgtattct caaaaacgta   2460
taatgtgaca gatgataaat acggatgtct gtctgggaat atccctgcct ggagttgat    2520 ggcgctgtat gtggctgcag ccatgcacga ttatgatcat ccaggaagga ctaatgcttt   2580
cctggttgca actagtgctc ctcaggcggt gctatataac gatcgttcag ttttggagaa   2640
tcatcacgca gctgctgcat ggaatctttt catgtcccgg ccagagtata acttcttaat   2700
taaccttgac catgtggaat ttaagcattt ccgtttcctt gtcattgaag caattttggc   2760
cactgacctg aagaaacact ttgacttcgt agccaaattt aatggcaagg taatgatga    2820 tgttggaata gattggacca atgaaaatga tcgtctactg gtttgtcaaa tgtgtataaa   2880
gttggctgat atcaatggtc cagctaaatg taaagaactc catcttcagt ggacagatgg   2940
tattgtcaat gaattttatg aacagggtga tgaagaggcc agccttggat acccataag    3000 cccccttcatg gatcgttctg ctcctcagct ggccaacctt caggaatcct tcatctctca   3060
cattgtgggg cctctgtgca actcctatga ttcagcagga ctaatgcctg aaaatgggt    3120 ggaagacagc gatgagtcag gagatactga tgacccagaa gaagaggagg aagaagcacc   3180
agcaccaaat gaagaggaaa cctgtgaaaa taatgaatct ccaaaaaaga gactttcaa    3240 aaggagaaaa atctactgcc aaataactca gcacctctta cagaaccaca agatgtggaa   3300
gaaagtcatt gaagagagc aacggttggc aggcatagaa aatcaatccc tggaccagac    3360
ccctcagtcg cactcttcag aacagatcca ggctatcaag gaagaagaag aagagaaagg   3420
gaaaccaaga ggcgaggaga taccaaccca aagccagac cagtgacaat ggatagaatg    3480
ggctgtgttt ccaaacagat tgacttgtca agactctct tcaagccagc acaacattta    3540
gacacaacac tgtagaaatt tgagatgggc aaatggctat tgcattttgg gattcttcgc   3600
attttgtgtg tatattttta cagtgaggta cattgttaaa aacttttgc tcaaagaagc    3660 tttcacattg caacaccagc ttctaaggat ttttaagga gggaatatat atgtgtgtgt    3720
gtatataagc tcccacatag atacatgtaa aacatattca cacccatgca cgcacacaca   3780
tacacactga aggccacgat tgctggctcc acaatttagt aacatttata ttaagatata   3840
tatatagtgg tcactgtgat ataataaatc ataaggaaa ccaaatcaca aaggagatgg    3900
tgtggcttag caaggaaaca gtgcaggaaa tgtaggttac caactaagca gcttttgctc   3960
ttagtactga gggatgaaag ttccagagca ttatttgaat tctgatacat cctgccaaca   4020
ctgtgtgtgt gtgtgtgtgt gtgtgtgtgt gtgtgtgt gtgtgaaaga gagacagaag     4080
ggaatggttt gagagggtgc ttgtgtgcat gtgtgtgcat atgtaaagag attttgtgg    4140 tttaagtaac tcagaatagc tgtagcaaat gactgaatac atgtgaacaa acagaaggaa   4200
gttcactctg gagtgtcttt gggaggcagc cattccaaat gccctcctcc atttagcttc   4260
aataaagggc cttttgctga tggagggcac tcaagggctg ggtgagaggg ccacgtgttt   4320
ggtattacat tactgctatg caccacttga aggagctcta tcaccagcct caaacccgaa   4380
agactgaggc attttccagt ctacttgcct aatgaatgta taggaactgt ctatgagtat   4440
ggatgtcact caactaagat caaatcacca tttaagggga tggcattctt tatacctaaa   4500
cacctaagag ctgaagtcag gtcttttaat caggttagaa ttctaaatga tgccagagaa   4560
ggcttgggaa attgtacttc agcgtgatag cctgtgtctt cttaatttgc tgcaaaatat   4620
```

```
gtggtagaga aagaaaagga aacagaaaaa tcactctggg ttatatagca agagatgaag      4680
gagaatattt caacacaggg tttttgtgtt gacataggaa aagcctgatt cttggcaact      4740
gttgtagttt gtcttcagg ggtgaaggtc ccactgacaa cccctgttgt ggtgttccac       4800
acgctgtttg ttggggtagc ttccatcggc agtctggccc attgtcagtc atgcttcttc     4860
tggccgggga gattatagag agattgtttg aagattgggt tattattgaa agtctttttt     4920
tttgtttgtt ttgttttggt ttgtttgttt atctacactt gtttatgctg tgagccaaac    4980
ctctatttaa aaagttgata ctcactttca atatttatt tcatattatt atatatgtca      5040
tgatagttat cttgatgtaa atatgaagat ttttttgttt ctgtagatag taaactcttt     5100
ttttaaaaaa ggaaaaggga aacatttta taaagttata ttttaatcac catttttata      5160
cattgtagtt ctctccaagc ccagtaagag aatgatgatt catttgcatg gaggtcgatg    5220
gacaaccaat catctacctt ttctaattta aatgataatc tgatatagtt ttattgccag   5280
ttaaatgagg atgctgcaaa gcatgttttt tcactagtaa cttttgctaa ctgaatgaat   5340
tctgggtcca tatctcccag atgaaaaact gttaaccaat accatatttt atagttggtg  5400
tccatttctt tccaacactg tttgttatga ttcttccttg agtacttata tacagacctg   5460
ctcattatct aaacaatctt accttctaag taaaccttga ttgtgatttc cagttttat   5520 tttctctgac gtagtagaaa ggaatgttta cattaaaaat acttttgttt ctcataaatg   5580
gatattgtac tccccctttt caaagcatta ttttacaata attcatgca ttttaaaaaa    5640 taaggcaaag ataatacgac aaaaaatata catggtttca aggcaaattc tccaataagt   5700
tggaaaatgt aaaaaggatc aagtggatgc agcctctacc taaataatta aaatatattt   5760
cagtatattt ctgaattaac accaggtctt cattatttag aacttactaa attgttttca   5820
ttttcttagt tttacctgtg tatctccatg tttgcaaaaa ttactataag tcaaattttg   5880
ccagtgaatt taactatttt tcttttccttg caattaaggg gaaaaagca tttatcttat   5940 cttctcatac cccttgcatc taagtactta gcaaagtcaa tatttcccca ttttccaaat   6000
gcgtccatct ctaacataaa tattaattga acatagagct atgtttggag tgagtggact   6060
ggcaggacag ttggaagtcc atcacagtct attgacagtt tcatcaaagc tgtatagtcc   6120
aactagtggg gcagcttggc tactatggtg gaagtctcag caaactgcct ggttttgttt    6180 gtttgtttg ttttaaggta caggaaataa gaggaataat agtggccaaa gcaattagaa     6240
catcttcatt ccagaactgt gttcagcaat ccaggcagat tgatacattt ttctttaaaa   6300
ataaattgct attacagcta gacgtcaatt gggataaata aagggatgaa gatccactaa  6360
gtttgtgact ttcatacaca cccagtacat ctcaaaggat gctaagggac attttctgcc 6420 agtgagttc tccccctttt tggtgacagc aatattatta tgttcacatc taactccaga    6480
gcttacttcc tgtggtgcca atgtatttgt tgcaatttac tacatttta tatgagccta    6540 tttataggtg ccattaaact caggtctttc aaatgaaaga gttctagcc cacttaggga    6600 aaaagataat tgtttagaaa accataaaat caatggtagg aaaagttgga actggttacc   6660
tggatgccat ggttctctgt taaataaagt aagagaccag gtgtattctg agtgtcatca  6720
gtgttatttt cagcatgcta ataaatgtct ttccggttat atatctatct aaattaacct  6780
ttaaaatatt ggtttccttg ataaaagcac cacttttgct tttgttagct gtaatatttt  6840
ttgtcattta gataagacct ggtttggctc tcaataaaag atgaagacag tagctctgta  6900
cagggatata tctatattag tcttcatctg atgaatgaag aaattttctc atattatgtt  6960
caagaaagta tttacttcct aaaaatagaa ttcccgattc tgtctatttt ggttgaatac  7020
```

-continued

```
cagaacaaat ctttccgttg caatcccagt aaaacgaaag aaaaggaata tcttacagac   7080
tgttcatatt agatgtatgt agactgttaa tttgcaattt ccccatattt cctgcctatc   7140
ttacccagat aactttcttt gaaggtaaaa gctgtgcaaa aggcatgaga ctcaggccta   7200
ctctttgttt aaatgatgga aaaatataaa ttatttctca agtaataaaa gtataaaaat   7260
tatcattata aataaagtct aaagtttgaa attattaatt taaaaaaaaa aaaaaaaaa    7319
```

```
<210> SEQ ID NO 2
<211> LENGTH: 1141
<212> TYPE: PRT
<213> ORGANISM: Homo sapiens

<400> SEQUENCE: 2

Met Ala Val Pro Gly Asp Ala Ala Arg Val Arg Asp Lys Pro Val His
1               5                   10                  15

Ser Gly Val Ser Gln Ala Pro Thr Ala Gly Arg Asp Cys His His Arg
                20                  25                  30

Ala Asp Pro Ala Ser Pro Arg Asp Ser Gly Cys Arg Gly Cys Trp Gly
            35                  40                  45

Asp Leu Val Leu Gln Pro Leu Arg Ser Arg Lys Leu Ser Ser Ala
        50                  55                  60

Leu Cys Ala Gly Ser Leu Ser Phe Leu Leu Ala Leu Leu Val Arg Leu
65                  70                  75                  80

Val Arg Gly Glu Val Gly Cys Asp Leu Glu Gln Cys Lys Glu Ala Ala
                85                  90                  95

Ala Ala Glu Glu Glu Ala Ala Pro Gly Ala Glu Gly Gly Val Phe
            100                 105                 110

Pro Gly Pro Arg Gly Gly Ala Pro Gly Gly Gly Ala Arg Leu Ser Pro
        115                 120                 125

Trp Leu Gln Pro Ser Ala Leu Leu Phe Ser Leu Leu Cys Ala Phe Phe
130                 135                 140

Trp Met Gly Leu Tyr Leu Leu Arg Ala Gly Val Arg Leu Pro Leu Ala
145                 150                 155                 160

Val Ala Leu Leu Ala Ala Cys Cys Gly Gly Glu Ala Leu Val Gln Ile
                165                 170                 175

Gly Leu Gly Val Gly Glu Asp His Leu Leu Ser Leu Pro Ala Ala Gly
            180                 185                 190

Val Val Leu Ser Cys Leu Ala Ala Ala Thr Trp Leu Val Leu Arg Leu
        195                 200                 205

Arg Leu Gly Val Leu Met Ile Ala Leu Thr Ser Ala Val Arg Thr Val
        210                 215                 220

Ser Leu Ile Ser Leu Glu Arg Phe Lys Val Ala Trp Arg Pro Tyr Leu
225                 230                 235                 240

Ala Tyr Leu Ala Gly Val Leu Gly Ile Leu Leu Ala Arg Tyr Val Glu
                245                 250                 255

Gln Ile Leu Pro Gln Ser Ala Glu Ala Ala Pro Arg Glu His Leu Gly
            260                 265                 270

Ser Gln Leu Ile Ala Gly Thr Lys Glu Asp Ile Pro Val Phe Lys Arg
        275                 280                 285

Arg Arg Arg Ser Ser Val Val Ser Ala Glu Met Ser Gly Cys Ser
        290                 295                 300

Ser Lys Ser His Arg Arg Thr Ser Leu Pro Cys Ile Pro Arg Glu Gln
305                 310                 315                 320
```

```
Leu Met Gly His Ser Glu Trp Asp His Lys Arg Gly Pro Arg Gly Ser
            325                 330                 335

Gln Ser Ser Gly Thr Ser Ile Thr Val Asp Ile Ala Val Met Gly Glu
            340                 345                 350

Ala His Gly Leu Ile Thr Asp Leu Leu Ala Asp Pro Ser Leu Pro Pro
            355                 360                 365

Asn Val Cys Thr Ser Leu Arg Ala Val Ser Asn Leu Leu Ser Thr Gln
370                 375                 380

Leu Thr Phe Gln Ala Ile His Lys Pro Arg Val Asn Pro Val Thr Ser
385                 390                 395                 400

Leu Ser Glu Asn Tyr Thr Cys Ser Asp Ser Glu Glu Ser Ser Glu Lys
            405                 410                 415

Asp Lys Leu Ala Ile Pro Lys Arg Leu Arg Arg Ser Leu Pro Pro Gly
            420                 425                 430

Leu Leu Arg Arg Val Ser Ser Thr Trp Thr Thr Thr Ser Ala Thr
            435                 440                 445

Gly Leu Pro Thr Leu Glu Pro Ala Pro Val Arg Arg Asp Arg Ser Thr
            450                 455                 460

Ser Ile Lys Leu Gln Glu Ala Pro Ser Ser Ser Pro Asp Ser Trp Asn
465                 470                 475                 480

Asn Pro Val Met Met Thr Leu Thr Lys Ser Arg Ser Phe Thr Ser Ser
                485                 490                 495

Tyr Ala Ile Ser Ala Ala Asn His Val Lys Ala Lys Lys Gln Ser Arg
            500                 505                 510

Pro Gly Ala Leu Ala Lys Ile Ser Pro Leu Ser Ser Pro Cys Ser Ser
            515                 520                 525

Pro Leu Gln Gly Thr Pro Ala Ser Ser Leu Val Ser Lys Ile Ser Ala
            530                 535                 540

Val Gln Phe Pro Glu Ser Ala Asp Thr Thr Ala Lys Gln Ser Leu Gly
545                 550                 555                 560

Ser His Arg Ala Leu Thr Tyr Thr Gln Ser Ala Pro Asp Leu Ser Pro
            565                 570                 575

Gln Ile Leu Thr Pro Pro Val Ile Cys Ser Ser Cys Gly Arg Pro Tyr
            580                 585                 590

Ser Gln Gly Asn Pro Ala Asp Glu Pro Leu Glu Arg Ser Gly Val Ala
            595                 600                 605

Thr Arg Thr Pro Ser Arg Thr Asp Asp Thr Ala Gln Val Thr Ser Asp
            610                 615                 620

Tyr Glu Thr Asn Asn Ser Asp Ser Ser Asp Ile Val Gln Asn Glu
625                 630                 635                 640

Asp Glu Thr Glu Cys Leu Arg Glu Pro Leu Arg Lys Ala Ser Ala Cys
            645                 650                 655

Ser Thr Tyr Ala Pro Glu Thr Met Met Phe Leu Asp Lys Pro Ile Leu
            660                 665                 670

Ala Pro Glu Pro Leu Val Met Asp Asn Leu Asp Ser Ile Met Glu Gln
            675                 680                 685

Leu Asn Thr Trp Asn Phe Pro Ile Phe Asp Leu Val Glu Asn Ile Gly
            690                 695                 700

Arg Lys Cys Gly Arg Ile Leu Ser Gln Val Ser Tyr Arg Leu Phe Glu
705                 710                 715                 720

Asp Met Gly Leu Phe Glu Ala Phe Lys Ile Pro Ile Arg Glu Phe Met
            725                 730                 735

Asn Tyr Phe His Ala Leu Glu Ile Gly Tyr Arg Asp Ile Pro Tyr His
```

```
                    740                 745                 750
Asn Arg Ile His Ala Thr Asp Val Leu His Ala Val Trp Tyr Leu Thr
            755                 760                 765

Thr Gln Pro Ile Pro Gly Leu Ser Thr Val Ile Asn Asp His Gly Ser
        770                 775                 780

Thr Ser Asp Ser Asp Ser Ser Gly Phe Thr His Gly His Met Gly
785                 790                 795                 800

Tyr Val Phe Ser Lys Thr Tyr Asn Val Thr Asp Asp Lys Tyr Gly Cys
                805                 810                 815

Leu Ser Gly Asn Ile Pro Ala Leu Glu Leu Met Ala Leu Tyr Val Ala
            820                 825                 830

Ala Ala Met His Asp Tyr Asp His Pro Gly Arg Thr Asn Ala Phe Leu
            835                 840                 845

Val Ala Thr Ser Ala Pro Gln Ala Val Leu Tyr Asn Asp Arg Ser Val
        850                 855                 860

Leu Glu Asn His His Ala Ala Ala Ala Trp Asn Leu Phe Met Ser Arg
865                 870                 875                 880

Pro Glu Tyr Asn Phe Leu Ile Asn Leu Asp His Val Glu Phe Lys His
                885                 890                 895

Phe Arg Phe Leu Val Ile Glu Ala Ile Leu Ala Thr Asp Leu Lys Lys
            900                 905                 910

His Phe Asp Phe Val Ala Lys Phe Asn Gly Lys Val Asn Asp Asp Val
            915                 920                 925

Gly Ile Asp Trp Thr Asn Glu Asn Asp Arg Leu Leu Val Cys Gln Met
        930                 935                 940

Cys Ile Lys Leu Ala Asp Ile Asn Gly Pro Ala Lys Cys Lys Glu Leu
945                 950                 955                 960

His Leu Gln Trp Thr Asp Gly Ile Val Asn Glu Phe Tyr Glu Gln Gly
                965                 970                 975

Asp Glu Glu Ala Ser Leu Gly Leu Pro Ile Ser Pro Phe Met Asp Arg
            980                 985                 990

Ser Ala Pro Gln Leu Ala Asn Leu Gln Glu Ser Phe Ile Ser His Ile
        995                 1000                1005

Val Gly Pro Leu Cys Asn Ser Tyr Asp Ser Ala Gly Leu Met Pro
    1010                1015                1020

Gly Lys Trp Val Glu Asp Ser Asp Glu Ser Gly Asp Thr Asp Asp
    1025                1030                1035

Pro Glu Glu Glu Glu Glu Ala Pro Ala Pro Asn Glu Glu Glu
    1040                1045                1050

Thr Cys Glu Asn Asn Glu Ser Pro Lys Lys Thr Phe Lys Arg
    1055                1060                1065

Arg Lys Ile Tyr Cys Gln Ile Thr Gln His Leu Leu Gln Asn His
    1070                1075                1080

Lys Met Trp Lys Lys Val Ile Glu Glu Glu Gln Arg Leu Ala Gly
    1085                1090                1095

Ile Glu Asn Gln Ser Leu Asp Gln Thr Pro Gln Ser His Ser Ser
    1100                1105                1110

Glu Gln Ile Gln Ala Ile Lys Glu Glu Glu Glu Lys Gly Lys
    1115                1120                1125

Pro Arg Gly Glu Glu Ile Pro Thr Gln Lys Pro Asp Gln
    1130                1135                1140

<210> SEQ ID NO 3
```

<211> LENGTH: 819
<212> TYPE: PRT
<213> ORGANISM: Homo sapiens

<400> SEQUENCE: 3

```
Met Val Thr Ile Phe Ser Lys Ser Trp Ser Phe Tyr Trp Glu Lys Ser
1               5                   10                  15

Ser Gly Thr Ser Ile Thr Val Asp Ile Ala Val Met Gly Glu Ala His
            20                  25                  30

Gly Leu Ile Thr Asp Leu Leu Ala Asp Pro Ser Leu Pro Pro Asn Val
        35                  40                  45

Cys Thr Ser Leu Arg Ala Val Ser Asn Leu Leu Ser Thr Gln Leu Thr
    50                  55                  60

Phe Gln Ala Ile His Lys Pro Arg Val Asn Pro Val Thr Ser Leu Ser
65                  70                  75                  80

Glu Asn Tyr Thr Cys Ser Asp Ser Glu Glu Ser Ser Lys Asp Lys Lys
                85                  90                  95

Leu Ala Ile Pro Lys Arg Leu Arg Arg Ser Leu Pro Pro Gly Leu Leu
            100                 105                 110

Arg Arg Val Ser Ser Thr Trp Thr Thr Thr Thr Ser Ala Thr Gly Leu
        115                 120                 125

Pro Thr Leu Glu Pro Ala Pro Val Arg Arg Asp Arg Ser Thr Ser Ile
    130                 135                 140

Lys Leu Gln Glu Ala Pro Ser Ser Ser Pro Asp Ser Trp Asn Asn Pro
145                 150                 155                 160

Val Met Met Thr Leu Thr Lys Ser Arg Ser Phe Thr Ser Ser Tyr Ala
                165                 170                 175

Ile Ser Ala Ala Asn His Val Lys Ala Lys Lys Gln Ser Arg Pro Gly
            180                 185                 190

Ala Leu Ala Lys Ile Ser Pro Leu Ser Ser Pro Cys Ser Ser Pro Leu
        195                 200                 205

Gln Gly Thr Pro Ala Ser Ser Leu Val Ser Lys Ile Ser Ala Val Gln
    210                 215                 220

Phe Pro Glu Ser Ala Asp Thr Thr Ala Lys Gln Ser Leu Gly Ser His
225                 230                 235                 240

Arg Ala Leu Thr Tyr Thr Gln Ser Ala Pro Asp Leu Ser Pro Gln Ile
                245                 250                 255

Leu Thr Pro Pro Val Ile Cys Ser Ser Cys Gly Arg Pro Tyr Ser Gln
            260                 265                 270

Gly Asn Pro Ala Asp Glu Pro Leu Glu Arg Ser Gly Val Ala Thr Arg
        275                 280                 285

Thr Pro Ser Arg Thr Asp Asp Thr Ala Gln Val Thr Ser Asp Tyr Glu
    290                 295                 300

Thr Asn Asn Asn Ser Asp Ser Ser Asp Ile Val Gln Asn Glu Asp Glu
305                 310                 315                 320

Thr Glu Cys Leu Arg Glu Pro Leu Arg Lys Ser Ala Cys Ser Thr
                325                 330                 335

Tyr Ala Pro Glu Thr Met Met Phe Leu Asp Lys Pro Ile Leu Ala Pro
            340                 345                 350

Glu Pro Leu Val Met Asp Asn Leu Asp Ser Ile Met Glu Gln Leu Asn
        355                 360                 365

Thr Trp Asn Phe Pro Ile Phe Asp Leu Val Glu Asn Ile Gly Arg Lys
    370                 375                 380

Cys Gly Arg Ile Leu Ser Gln Val Ser Tyr Arg Leu Phe Glu Asp Met
```

```
385                 390                 395                 400
Gly Leu Phe Glu Ala Phe Lys Ile Pro Ile Arg Glu Phe Met Asn Tyr
                405                 410                 415

Phe His Ala Leu Glu Ile Gly Tyr Arg Asp Ile Pro Tyr His Asn Arg
                420                 425                 430

Ile His Ala Thr Asp Val Leu His Ala Val Trp Tyr Leu Thr Thr Gln
                435                 440                 445

Pro Ile Pro Gly Leu Ser Thr Val Ile Asn Asp His Gly Ser Thr Ser
        450                 455                 460

Asp Ser Asp Ser Asp Ser Gly Phe Thr His Gly His Met Gly Tyr Val
465                 470                 475                 480

Phe Ser Lys Thr Tyr Asn Val Thr Asp Asp Lys Tyr Gly Cys Leu Ser
                485                 490                 495

Gly Asn Ile Pro Ala Leu Glu Leu Met Ala Leu Tyr Val Ala Ala Ala
        500                 505                 510

Met His Asp Tyr Asp His Pro Gly Arg Thr Asn Ala Phe Leu Val Ala
515                 520                 525

Thr Ser Ala Pro Gln Ala Val Leu Tyr Asn Asp Arg Ser Val Leu Glu
530                 535                 540

Asn His His Ala Ala Ala Ala Trp Asn Leu Phe Met Ser Arg Pro Glu
545                 550                 555                 560

Tyr Asn Phe Leu Ile Asn Leu Asp His Val Glu Phe Lys His Phe Arg
                565                 570                 575

Phe Leu Val Ile Glu Ala Ile Leu Ala Thr Asp Leu Lys Lys His Phe
                580                 585                 590

Asp Phe Val Ala Lys Phe Asn Gly Lys Val Asn Asp Asp Val Gly Ile
        595                 600                 605

Asp Trp Thr Asn Glu Asn Asp Arg Leu Leu Val Cys Gln Met Cys Ile
        610                 615                 620

Lys Leu Ala Asp Ile Asn Gly Pro Ala Lys Cys Lys Glu Leu His Leu
625                 630                 635                 640

Gln Trp Thr Asp Gly Ile Val Asn Glu Phe Tyr Glu Gln Gly Asp Glu
                645                 650                 655

Glu Ala Ser Leu Gly Leu Pro Ile Ser Pro Phe Met Asp Arg Ser Ala
                660                 665                 670

Pro Gln Leu Ala Asn Leu Gln Glu Ser Phe Ile Ser His Ile Val Gly
        675                 680                 685

Pro Leu Cys Asn Ser Tyr Asp Ser Ala Gly Leu Met Pro Gly Lys Trp
        690                 695                 700

Val Glu Asp Ser Asp Glu Ser Gly Asp Thr Asp Asp Pro Glu Glu Glu
705                 710                 715                 720

Glu Glu Glu Ala Pro Ala Pro Asn Glu Glu Thr Cys Glu Asn Asn
                725                 730                 735

Glu Ser Pro Lys Lys Lys Thr Phe Lys Arg Arg Lys Ile Tyr Cys Gln
                740                 745                 750

Ile Thr Gln His Leu Leu Gln Asn His Lys Met Trp Lys Lys Val Ile
        755                 760                 765

Glu Glu Glu Gln Arg Leu Ala Gly Ile Glu Asn Gln Ser Leu Asp Gln
        770                 775                 780

Thr Pro Gln Ser His Ser Ser Glu Gln Ile Gln Ala Ile Lys Glu Glu
785                 790                 795                 800

Glu Glu Glu Lys Gly Lys Pro Arg Gly Glu Ile Pro Thr Gln Lys
                805                 810                 815
```

Pro Asp Gln

<210> SEQ ID NO 4
<211> LENGTH: 6091
<212> TYPE: DNA
<213> ORGANISM: Homo sapiens

<400> SEQUENCE: 4

| | | | | | | |
|---|---|---|---|---|---|---|
| gctcgcgcgc | ccaacggacc | aggctggggc | cgtgaggtaa | ctgttgcagc | cagcggaggt | 60 |
| gggaggcgac | actgagtctc | cagtcccgag | aggtgcccga | gggaaaagga | ggcggcagct | 120 |
| aaactggtcc | tggagagaag | ccccttccgc | ccctctcctc | agccagcatg | tcccggactc | 180 |
| cgccgctcct | cagtccgcgc | ggtggggacc | ccgggccgtg | gcggccggcg | cagccctgac | 240 |
| gggttgcgaa | ccaggggcg | ccccgaacgc | ggggggttggg | gtctgggagc | gcgagcggcc | 300 |
| gctacggtac | gagcggggtg | tgctgagtcc | cgtggccacc | cccggcccca | gccatgagga | 360 |
| gggacgagcg | agacgccaaa | gccatgcggt | ccctgcagcc | gccggatggg | gccggctcgc | 420 |
| ccccccgagag | tctgaggaac | ggctacgtga | agagctgcgt | gagccccttg | cggcaggacc | 480 |
| ctccgcgcgg | cttcttcttc | cacctctgcc | gcttctgcaa | cgtggagctg | cggccgccgc | 540 |
| cggcctctcc | ccagcagccg | cggcgctgct | ccccccttctg | ccgggcgcgc | ctctcgctgg | 600 |
| gcgccctggc | tgcctttgtc | ctcgccctgc | tgctgggcgc | ggaacccgag | agctgggctg | 660 |
| ccggggccgc | ctggctgcgg | acgctgctga | gcgtgtgttc | gcacagcttg | agccccctct | 720 |
| tcagcatcgc | ctgtgccttc | ttcttcctca | cctgcttcct | cacccggacc | aagcggggac | 780 |
| ccggcccggg | ccggagctgc | ggctcctggt | ggctgctggc | gctgcccgcc | tgctgttacc | 840 |
| tgggggactt | cttggtgtgg | cagtggtggt | cttggcttg | ggggatggc | gacgcagggt | 900 |
| ccgcggcccc | gcacacgccc | ccggaggcgg | cagcgggcag | gttgctgctg | gtgctgagct | 960 |
| gcgtagggct | gctgctgacg | ctcgcgcacc | cgctgcggct | ccggcactgc | gttctggtgc | 1020 |
| tgctcctggc | cagcttcgtc | tggtgggtct | ccttcaccag | cctcgggtcg | ctgccctccg | 1080 |
| ccctcaggcc | gctgctctcc | ggcctggtgg | ggggcgctgg | ctgcctgctg | gcctggggt | 1140 |
| tggatcactt | ctttcaaatc | agggaagcgc | ctcttcatcc | tcgactgtcc | agtgccgccg | 1200 |
| aagaaaaagt | gcctgtgatc | cgaccccgga | ggaggtccag | ctgcgtgtcg | ttaggagaaa | 1260 |
| ctgcagccag | ttactatggc | agttgcaaaa | tattcaggag | accgtcgttg | ccttgtattt | 1320 |
| ccagagaaca | gatgattctt | tgggattggg | acttaaaaca | atggtataag | cctcattatc | 1380 |
| aaaattctgg | aggtggaaat | ggagttgatc | tttcagtgct | aaatgaggct | cgcaatatgg | 1440 |
| tgtcagatct | tctgactgat | ccaagccttc | caccacaagt | catttcctct | ctacggagta | 1500 |
| ttagtagctt | aatgggtgct | ttctcaggtt | cctgtaggcc | aaagattaat | cctctcacac | 1560 |
| catttcctgg | attttacccc | tgttctgaaa | tagaggaccc | agctgagaaa | ggggatagaa | 1620 |
| aacttaacaa | gggactaaat | aggaatagtt | tgccaactcc | acagctgagg | agaagctcag | 1680 |
| gaacttcagg | attgctacct | gttgaacagt | cttcaaggtg | ggatcgtaat | aatggcaaaa | 1740 |
| gacctcacca | agaatttggc | atttcaagtc | aaggatgcta | tctaaatggg | ccttttaatt | 1800 |
| caaatctact | gactatcccg | aagcaaaggt | catcttctgt | atcactgact | caccatgtag | 1860 |
| gtctcagaag | agctggtgtt | ttgtccagtc | tgagtcctgt | gaattcttcc | aaccatggac | 1920 |
| cagtgtctac | tggctctcta | actaatcgat | cacccataga | atttcctgat | actgctgatt | 1980 |
| ttcttaataa | gccaagcgtt | atcttgcaga | gatctctggg | caatgcacct | aatactccag | 2040 |

-continued

```
atttttatca gcaacttaga aattctgata gcaatctgtg taacagctgt ggacatcaaa      2100
tgctgaaata tgtttcaaca tctgaatcag atggtacaga ttgctgcagt ggaaaatcag      2160
gtgaagaaga aaacattttc tcgaaagaat cattcaaact tatggaaact caacaagaag      2220
aggaaacaga gaagaaagac agcagaaaat tatttcagga aggtgataag tggctaacag      2280
aagaggcaca gagtgaacag caaacaaata ttgaacagga agtatcactg gacctgattt      2340
tagtagaaga gtatgactca ttaatagaaa agatgagcaa ctggaatttt ccaattttg       2400 aacttgtaga aaagatggga gagaaatcag gaaggattct cagtcaggtt atgtatacct      2460
tatttcaaga cactggttta ttggaaatat ttaaaattcc cactcaacaa tttatgaact      2520
attttcgtgc attagaaaat ggctatcgag acattcctta tcacaatcgt atacatgcca      2580
cagatgtgct acatgcagtt tggtatctga caacacggcc agttcctggc ttacagcaga      2640
tccacaatgg ttgtggaaca ggaaatgaaa cagattctga tggtagaatt aaccatgggc      2700
gaattgctta tatttcttcg aagagctgct ctaatcctga tgagagttat ggctgcctgt      2760
cttcaaacat tcctgcatta gaattgatgg ctctatacgt ggcagctgcc atgcatgatt      2820
atgatcaccc agggaggaca aatgcatttc tagtggctac aaatgcccct caggcagttt      2880
tatacaatga cagatctgtt ctggaaaatc atcatgctgc gtcagcttgg aatctatatc      2940
tttctcgccc agaatacaac ttccttcttc atcttgatca tgtggaattc aagcgctttc      3000
gttttttagt cattgaagca atccttgcta cggatcttaa aaagcatttt gattttctcg      3060
cagaattcaa tgccaaggca aatgatgtaa atagtaatgg catagaatgg agtaatgaaa      3120
atgatcgcct cttggtatgc caggtgtgca tcaaactggc agatataaat ggcccagcaa      3180
aagttcgaga cttgcatttg aaatggacag aaggcattgt caatgaattt tatgagcagg      3240
gagatgaaga agcaaatctt ggtctgccca tcagtccatt catggatcgt tcttctcctc      3300
aactagcaaa actccaagaa tcttttatca cccacatagt gggtcccctg tgtaactcct      3360
atgatgctgc tggtttgcta ccaggtcagt ggttagaagc agaagaggat aatgatactg      3420
aaagtggtga tgatgaagac ggtgaagaat tagatacaga agatgaagaa atggaaaaca      3480
atctaaatcc aaaaccacca agaaggaaaa gcagacggcg aatattttgt cagctaatgc      3540
accacctcac tgaaaaccac aagatatgga aggaaatcgt agaggaagaa gaaaaatgta      3600
aagctgatgg gaataaactg caggtggaga attcctcctt acctcaagca gatgagattc      3660
aggtaattga agaggcagat gaagaggaat agcgacagtt tgagtaaaag aaaagtcata      3720
ttgaagaagc ccagagggtt gtgcccaggg gcagaaatca ttgcctagtg ttcaccggct      3780
gactctcaac tgaccattcc catgtggaca ggccttaata ctgtgagagg atccttgctc      3840
tgctggcagt ttcccactcc tatgcacttt cacaggaact agaaaactat tcttaaacca      3900
aaaataccat ccgtgttgac ccatgttgca gagcccttac ttaaatcctt cactggtgta      3960
tgaatacttt gtcataatgc tgctttgctg ggtagtgagc tcttattttt cactgggggt      4020
cagctataac taaaaactca agtgacatat ttcagttacc aaagtggcca ggaacttttt      4080
gcttttatga aaatagattc atattgtatt tcccagtgtg tctttatgt ctttgaatgt       4140 tttggagaaa agtctatgcc tgtctaaaaa tgaatccagt gttgcctttc tgagggattt      4200
ctgctcaatg caatacactg ttcagtgcta ttctcccagc taggtttatc catgaaggac      4260
tgagtgacct tgttgtatt taacaaaatc caggtgcatc aatttctgat gcttttact        4320 attgtgtatt atctactatg tgtgttttat ttctgctgag agtattcagg tttgccatgg      4380
acatcagaag tttgaattcc agtcttatct tatgttccat ggctgaattt taaagctgtt      4440
```

-continued

```
taggtttaac aatgaaggga tttattcttt agtcaaaatt gttgttttta ctctagctca    4500
ggattcgtat ttttaaagat ttagttaata tgaacacagc acagatttgt tagaagaaaa    4560
aaaatttgct gtaataccaa aactaacctc atcaaagata cagaaaaaaa gaaatatagt    4620
gagccctaaa ggacacatac attgaataaa taattggaac atgtggttat ctttagatcc    4680
acatcttagc tgtcatttgt tcactctaaa actgatgttc atctttctgt taatttccct    4740
ctgcctaaag actacatgac agaaatgacc tatcactact tattatttct gaagcctaac    4800
tgcaagactg atttctgaga acaagtaaag aactggaata cttattttc atataaaaat    4860
ctaaatgtgt taataaatca tttcatacaa aagtacatta ttaaataacc acattattaa    4920
aataattgca agaaaatgga ccatatttac aatgttttgt aaacttgcta gtgtgtggat    4980
atgtacccta cttgtgaaat acatttgaag atataaagag cagccaaaat gatggcaaaa    5040
tggtaggcta atattttcta ttattattgg agaacatatc atattttgga atcatgcaat    5100
tttgcacaca gtgaaaccat taattttcca aggtaattcc tttagaatat ggtattggca    5160
tgcagtttct tacttatcta gaatatttgg cttatctgaa agatatcaat ttaagatctc    5220
tggaagtgtt agaattttg atccttcaca gtgtcaatat ttaatgaatc actaagcttt    5280
atttattaga cgtgttgagt gagtgctgag ttccttgctg ccactttgt taccattgtc    5340
acacactatg tgtaaaccag tcccaccact tattactaat aaaatttga ctgataattt    5400
atatttgcac ttacaatata tatatcctgt ccttatattt ctctagagta cattttccat    5460
catgtttaag tgtatttctg ctattatttc ctctcctgca gaatacatac aagtgtatgt    5520
gtataaagtc atacatgtac aagcatgcat attgagattg aatcacattt ccatactgtc    5580
tgttatttta ttgggtttta tattgggttt ctttagttta tgttgttttc tcaaaagcag    5640
cattttaaat tacgaatact ggacttattg gatttaatta taaatccaat tactactgga    5700
aactcatttt tacataatat agtccttaaa ttatttaacc cttgctaagt aattgacata    5760
tgtaacaata actagcctaa agaaacccaa aaaagtatct ctcccgagct gaaacttaaa    5820
aattcgtaag tgtaagaaag aatgtgagaa tatattaaat gcacactgta ccattagatg    5880
aaatcttact tgagaaattg ccataagcca tattacagat cttactttgt tactgaatca    5940
gattaatttc ttgttataat aattttcatc ataaattttc tatttttaaa gccgctggta    6000
ctagaaatat tcttttaatg ctatatctat gtacctactg acacattttt ctccataaaa    6060
gtacttttaa aaattacttc atgatttgaa a                                   6091
```

<210> SEQ ID NO 5
<211> LENGTH: 1112
<212> TYPE: PRT
<213> ORGANISM: Homo sapiens

<400> SEQUENCE: 5

```
Met Arg Arg Asp Glu Arg Asp Ala Lys Ala Met Arg Ser Leu Gln Pro
1               5                   10                  15

Pro Asp Gly Ala Gly Ser Pro Glu Ser Leu Arg Asn Gly Tyr Val
            20                  25                  30

Lys Ser Cys Val Ser Pro Leu Arg Gln Asp Pro Arg Gly Phe Phe
        35                  40                  45

Phe His Leu Cys Arg Phe Cys Asn Val Glu Leu Arg Pro Pro Ala
    50                  55                  60

Ser Pro Gln Gln Pro Arg Arg Cys Ser Pro Phe Cys Arg Ala Arg Leu
65                  70                  75                  80
```

```
Ser Leu Gly Ala Leu Ala Ala Phe Val Leu Ala Leu Leu Gly Ala
                 85                  90                  95

Glu Pro Glu Ser Trp Ala Ala Gly Ala Ala Trp Leu Arg Thr Leu Leu
            100                 105                 110

Ser Val Cys Ser His Ser Leu Ser Pro Leu Phe Ser Ile Ala Cys Ala
        115                 120                 125

Phe Phe Phe Leu Thr Cys Phe Leu Thr Arg Thr Lys Arg Gly Pro Gly
    130                 135                 140

Pro Gly Arg Ser Cys Gly Ser Trp Trp Leu Leu Ala Leu Pro Ala Cys
145                 150                 155                 160

Cys Tyr Leu Gly Asp Phe Leu Val Trp Gln Trp Ser Trp Pro Trp
                165                 170                 175

Gly Asp Gly Asp Ala Gly Ser Ala Ala Pro His Thr Pro Glu Ala
                180                 185                 190

Ala Ala Gly Arg Leu Leu Val Leu Ser Cys Val Gly Leu Leu Leu
            195                 200                 205

Thr Leu Ala His Pro Leu Arg Leu Arg His Cys Val Leu Val Leu Leu
            210                 215                 220

Leu Ala Ser Phe Val Trp Trp Val Ser Phe Thr Ser Leu Gly Ser Leu
225                 230                 235                 240

Pro Ser Ala Leu Arg Pro Leu Leu Ser Gly Leu Val Gly Gly Ala Gly
                245                 250                 255

Cys Leu Leu Ala Leu Gly Leu Asp His Phe Phe Gln Ile Arg Glu Ala
                260                 265                 270

Pro Leu His Pro Arg Leu Ser Ser Ala Ala Glu Glu Lys Val Pro Val
                275                 280                 285

Ile Arg Pro Arg Arg Arg Ser Ser Cys Val Ser Leu Gly Glu Thr Ala
                290                 295                 300

Ala Ser Tyr Tyr Gly Ser Cys Lys Ile Phe Arg Arg Pro Ser Leu Pro
305                 310                 315                 320

Cys Ile Ser Arg Glu Gln Met Ile Leu Trp Asp Trp Asp Leu Lys Gln
                325                 330                 335

Trp Tyr Lys Pro His Tyr Gln Asn Ser Gly Gly Asn Gly Val Asp
                340                 345                 350

Leu Ser Val Leu Asn Glu Ala Arg Asn Met Val Ser Asp Leu Leu Thr
            355                 360                 365

Asp Pro Ser Leu Pro Pro Gln Val Ile Ser Ser Leu Arg Ser Ile Ser
    370                 375                 380

Ser Leu Met Gly Ala Phe Ser Gly Ser Cys Arg Pro Lys Ile Asn Pro
385                 390                 395                 400

Leu Thr Pro Phe Pro Gly Phe Tyr Pro Cys Ser Glu Ile Glu Asp Pro
                405                 410                 415

Ala Glu Lys Gly Asp Arg Lys Leu Asn Lys Gly Leu Asn Arg Asn Ser
            420                 425                 430

Leu Pro Thr Pro Gln Leu Arg Ser Ser Gly Thr Ser Gly Leu Leu
    435                 440                 445

Pro Val Glu Gln Ser Ser Arg Trp Asp Arg Asn Asn Gly Lys Arg Pro
450                 455                 460

His Gln Glu Phe Gly Ile Ser Ser Gln Gly Cys Tyr Leu Asn Gly Pro
465                 470                 475                 480

Phe Asn Ser Asn Leu Leu Thr Ile Pro Lys Gln Arg Ser Ser Val
                485                 490                 495
```

```
Ser Leu Thr His His Val Gly Leu Arg Arg Ala Gly Val Leu Ser Ser
            500                 505                 510

Leu Ser Pro Val Asn Ser Ser Asn His Gly Pro Val Ser Thr Gly Ser
        515                 520                 525

Leu Thr Asn Arg Ser Pro Ile Glu Phe Pro Asp Thr Ala Asp Phe Leu
    530                 535                 540

Asn Lys Pro Ser Val Ile Leu Gln Arg Ser Leu Gly Asn Ala Pro Asn
545                 550                 555                 560

Thr Pro Asp Phe Tyr Gln Gln Leu Arg Asn Ser Asp Ser Asn Leu Cys
                565                 570                 575

Asn Ser Cys Gly His Gln Met Leu Lys Tyr Val Ser Thr Ser Glu Ser
            580                 585                 590

Asp Gly Thr Asp Cys Cys Ser Gly Lys Ser Gly Glu Glu Glu Asn Ile
        595                 600                 605

Phe Ser Lys Glu Ser Phe Lys Leu Met Glu Thr Gln Gln Glu Glu Glu
    610                 615                 620

Thr Glu Lys Lys Asp Ser Arg Lys Leu Phe Gln Glu Gly Asp Lys Trp
625                 630                 635                 640

Leu Thr Glu Glu Ala Gln Ser Glu Gln Gln Thr Asn Ile Glu Gln Glu
                645                 650                 655

Val Ser Leu Asp Leu Ile Leu Val Glu Glu Tyr Asp Ser Leu Ile Glu
            660                 665                 670

Lys Met Ser Asn Trp Asn Phe Pro Ile Phe Glu Leu Val Glu Lys Met
        675                 680                 685

Gly Glu Lys Ser Gly Arg Ile Leu Ser Gln Val Met Tyr Thr Leu Phe
    690                 695                 700

Gln Asp Thr Gly Leu Leu Glu Ile Phe Lys Ile Pro Thr Gln Gln Phe
705                 710                 715                 720

Met Asn Tyr Phe Arg Ala Leu Glu Asn Gly Tyr Arg Asp Ile Pro Tyr
                725                 730                 735

His Asn Arg Ile His Ala Thr Asp Val Leu His Ala Val Trp Tyr Leu
            740                 745                 750

Thr Thr Arg Pro Val Pro Gly Leu Gln Gln Ile His Asn Gly Cys Gly
        755                 760                 765

Thr Gly Asn Glu Thr Asp Ser Asp Gly Arg Ile Asn His Gly Arg Ile
    770                 775                 780

Ala Tyr Ile Ser Ser Lys Ser Cys Ser Asn Pro Asp Glu Ser Tyr Gly
785                 790                 795                 800

Cys Leu Ser Ser Asn Ile Pro Ala Leu Glu Leu Met Ala Leu Tyr Val
                805                 810                 815

Ala Ala Ala Met His Asp Tyr Asp His Pro Gly Arg Thr Asn Ala Phe
            820                 825                 830

Leu Val Ala Thr Asn Ala Pro Gln Ala Val Leu Tyr Asn Asp Arg Ser
        835                 840                 845

Val Leu Glu Asn His His Ala Ala Ser Ala Trp Asn Leu Tyr Leu Ser
    850                 855                 860

Arg Pro Glu Tyr Asn Phe Leu His Leu Asp His Val Glu Phe Lys
865                 870                 875                 880

Arg Phe Arg Phe Leu Val Ile Glu Ala Ile Leu Ala Thr Asp Leu Lys
                885                 890                 895

Lys His Phe Asp Phe Leu Ala Glu Phe Asn Ala Lys Ala Asn Asp Val
            900                 905                 910

Asn Ser Asn Gly Ile Glu Trp Ser Asn Glu Asn Asp Arg Leu Leu Val
```

```
                915                 920                 925
Cys Gln Val Cys Ile Lys Leu Ala Asp Ile Asn Gly Pro Ala Lys Val
    930                 935                 940
Arg Asp Leu His Leu Lys Trp Thr Glu Gly Ile Val Asn Glu Phe Tyr
945                 950                 955                 960
Glu Gln Gly Asp Glu Glu Ala Asn Leu Gly Leu Pro Ile Ser Pro Phe
                965                 970                 975
Met Asp Arg Ser Ser Pro Gln Leu Ala Lys Leu Gln Glu Ser Phe Ile
            980                 985                 990
Thr His Ile Val Gly Pro Leu Cys Asn Ser Tyr Asp Ala Ala Gly Leu
        995                 1000                1005
Leu Pro Gly Gln Trp Leu Glu Ala Glu Asp Asn Asp Thr Glu
    1010                1015                1020
Ser Gly Asp Asp Glu Asp Gly Glu Glu Leu Asp Thr Glu Asp Glu
    1025                1030                1035
Glu Met Glu Asn Asn Leu Asn Pro Lys Pro Pro Arg Arg Lys Ser
    1040                1045                1050
Arg Arg Arg Ile Phe Cys Gln Leu Met His His Leu Thr Glu Asn
    1055                1060                1065
His Lys Ile Trp Lys Glu Ile Val Glu Glu Glu Lys Cys Lys
    1070                1075                1080
Ala Asp Gly Asn Lys Leu Gln Val Glu Asn Ser Ser Leu Pro Gln
    1085                1090                1095
Ala Asp Glu Ile Gln Val Ile Glu Glu Ala Asp Glu Glu Glu
    1100                1105                1110
```

<210> SEQ ID NO 6
<211> LENGTH: 2530
<212> TYPE: DNA
<213> ORGANISM: Homo sapiens

<400> SEQUENCE: 6

```
tttgtaactt cacttcagcc tcccattgat cgctttctgc aaccattcag actgatctcg     60
ggctcctatt tcatttacat tgtgtgcaca ccaagtaacc agtgggaaaa ctttagaggg    120
tacttaaacc ccagaaaatt ctgaaaccgg gctcttgagc cgctatcctc gggcctgctc    180
ccaccctgtg gagtgcactt tcgttttcaa taaatctctg cttttgttgc ttcattcttt    240
ccttgctttg tttgtgtgtt tgtccagttc tttgttcaac acgccaagaa cctggacact    300
cttcactggt aacatatttt ggcaagccaa ccaggagaaa agaatttctg cttggacact    360
gcatagctgc tgggaaaatg aacatcagtg ttgatttgga aacgaattat gccgagttgg    420
ttctagatgt gggaagagtc actcttggag agaacagtag gaaaaaaatg aaggattgta    480
aactgagaaa aaagcagaat gaaagtgtct cacgagctat gtgtgctctg ctcaattctg    540
gaggggagt gatcaaggct gaaattgaga atgaagacta tagttataca aaagatggaa    600
taggactaga tttggaaaat tcttttagta acattctgtt atttgttcct gagtacttag    660
acttcatgca gaatggtaac tactttctga tttttgtgaa gtcatggagc ttgaacacct    720
ctggtctgcg gattaccacc ttgagctcca atttgtacaa aagagatata acatctgcaa    780
aagtcatgaa tgccactgct gcactggagt tcctcaaaga catgaaaaag actagaggga    840
gattgtattt aagaccagaa ttgctggcaa agaggccctg tgttgatata caagaagaaa    900
ataacatgaa ggccttggcc gggttttttt ttgatagaac agaacttgat cggaagaaa    960
aattgacctt tactgaatcc acacatgttg aaattaaaaa cttctcgaca gaaaagttgt   1020
```

```
tacaacgaat taaagagatt ctccctcaat atgtttctgc atttgcaaat actgatggag    1080
gatatttgtt cattggttta aatgaagata aagaaataat tggctttaaa gcagagatga    1140
gtgacctcga tgacttagaa agagaaatcg aaaagtccat taggaagatg cctgtgcatc    1200
acttctgtat ggagaagaag aagataaatt attcatgcaa attccttgga gtatatgata    1260
aaggaagtct tgtggatat gtctgtgcac tcagagtgga gcgcttctgc tgtgcagtgt     1320
ttgctaaaga gcctgattcc tggcatgtga agataaccg tgtgatgcag ttgaccagga     1380
aggaatggat ccagttcatg gtggaggctg aaccaaaatt ttccagttca tatgaagagg    1440
tgatctctca aataaatacg tcattacctg ctccccacag ttggcctctt ttggaatggc    1500
aacggcagag acatcactgt ccagggctat caggaaggat aacgtatact ccagaaaacc    1560
tttgcagaaa actgttctta caacatgaag gacttaagca attaatatgt gaagaaatgg    1620
actctgtcag aaagggctca ctgatcttct ctaggagctg gtctgtggat ctgggcttgc    1680
aagagaacca caaagtcctc tgtgatgctc ttctgatttc ccaggacagt cctccagtcc    1740
tatacacctt ccacatggta caggatgagg agtttaaagg ctattctaca caaactgccc    1800
taaccttaaa gcagaagctg gcaaaaattg gtggttacac taaaaaagtg tgtgtcatga    1860
caaagatctt ctacttgagc cctgaaggca tgacaagctg ccagtatgat ttaaggtcgc    1920
aagtaattta ccctgaatcc tactatttta caagaaggaa atacttgctg aaagcccttt    1980
ttaaagcctt aaagagactc aagtctctga gagaccagtt ttcctttgca gaaaatctat    2040
accagataat cggtatagat tgctttcaga agaatgataa aaagatgttt aaatcttgtc    2100
gaaggctcac ctgatggaaa atggactggg ctactgagat attttcatt atatatttga     2160 taacattctc taattctgtg aaaatatttc tttgaaaact ttgcaagtta agcaacttaa    2220
tgtgatgttg gataattggg ttttgtctat tttcacttct ccctaaataa tcttcacaga    2280
tattgtttga gggatattag gaaaattaat ttgttaactc gtctgtgcac agtattattt    2340
actctgtctg tagttcctga ataaatttc ttccatgctt gaactgggaa aattgcaaca     2400
cttttattct taatgacaac agtgaaaatc tcccagcata tacctagaaa acaattataa    2460
cttacaaaag attatccttg atgaaactca gaatttccac agtgggaatg aataagaagg    2520
caaaactcat                                                          2530
```

<210> SEQ ID NO 7
<211> LENGTH: 578
<212> TYPE: PRT
<213> ORGANISM: Homo sapiens

<400> SEQUENCE: 7

Met Asn Ile Ser Val Asp Leu Glu Thr Asn Tyr Ala Glu Leu Val Leu
1               5                   10                  15

Asp Val Gly Arg Val Thr Leu Gly Glu Asn Ser Arg Lys Lys Met Lys
                20                  25                  30

Asp Cys Lys Leu Arg Lys Lys Gln Asn Glu Ser Val Ser Arg Ala Met
            35                  40                  45

Cys Ala Leu Leu Asn Ser Gly Gly Gly Val Ile Lys Ala Glu Ile Glu
        50                  55                  60

Asn Glu Asp Tyr Ser Tyr Thr Lys Asp Gly Ile Gly Leu Asp Leu Glu
65                  70                  75                  80

Asn Ser Phe Ser Asn Ile Leu Leu Phe Val Pro Glu Tyr Leu Asp Phe
                85                  90                  95

```
Met Gln Asn Gly Asn Tyr Phe Leu Ile Phe Val Lys Ser Trp Ser Leu
                100                 105                 110

Asn Thr Ser Gly Leu Arg Ile Thr Thr Leu Ser Ser Asn Leu Tyr Lys
        115                 120                 125

Arg Asp Ile Thr Ser Ala Lys Val Met Asn Ala Thr Ala Ala Leu Glu
130                 135                 140

Phe Leu Lys Asp Met Lys Lys Thr Arg Gly Arg Leu Tyr Leu Arg Pro
145                 150                 155                 160

Glu Leu Leu Ala Lys Arg Pro Cys Val Asp Ile Gln Glu Glu Asn Asn
                165                 170                 175

Met Lys Ala Leu Ala Gly Val Phe Phe Asp Arg Thr Glu Leu Asp Arg
            180                 185                 190

Lys Glu Lys Leu Thr Phe Thr Glu Ser Thr His Val Glu Ile Lys Asn
        195                 200                 205

Phe Ser Thr Glu Lys Leu Leu Gln Arg Ile Lys Glu Ile Leu Pro Gln
    210                 215                 220

Tyr Val Ser Ala Phe Ala Asn Thr Asp Gly Gly Tyr Leu Phe Ile Gly
225                 230                 235                 240

Leu Asn Glu Asp Lys Glu Ile Ile Gly Phe Lys Ala Glu Met Ser Asp
                245                 250                 255

Leu Asp Asp Leu Glu Arg Glu Ile Glu Lys Ser Ile Arg Lys Met Pro
            260                 265                 270

Val His His Phe Cys Met Glu Lys Lys Ile Asn Tyr Ser Cys Lys
        275                 280                 285

Phe Leu Gly Val Tyr Asp Lys Gly Ser Leu Cys Gly Tyr Val Cys Ala
    290                 295                 300

Leu Arg Val Glu Arg Phe Cys Cys Ala Val Phe Ala Lys Glu Pro Asp
305                 310                 315                 320

Ser Trp His Val Lys Asp Asn Arg Val Met Gln Leu Thr Arg Lys Glu
                325                 330                 335

Trp Ile Gln Phe Met Val Glu Ala Glu Pro Lys Phe Ser Ser Ser Tyr
            340                 345                 350

Glu Glu Val Ile Ser Gln Ile Asn Thr Ser Leu Pro Ala Pro His Ser
        355                 360                 365

Trp Pro Leu Leu Glu Trp Gln Arg Gln Arg His His Cys Pro Gly Leu
    370                 375                 380

Ser Gly Arg Ile Thr Tyr Thr Pro Glu Asn Leu Cys Arg Lys Leu Phe
385                 390                 395                 400

Leu Gln His Glu Gly Leu Lys Gln Leu Ile Cys Glu Glu Met Asp Ser
                405                 410                 415

Val Arg Lys Gly Ser Leu Ile Phe Ser Arg Ser Trp Ser Val Asp Leu
            420                 425                 430

Gly Leu Gln Glu Asn His Lys Val Leu Cys Asp Ala Leu Leu Ile Ser
        435                 440                 445

Gln Asp Ser Pro Pro Val Leu Tyr Thr Phe His Met Val Gln Asp Glu
    450                 455                 460

Glu Phe Lys Gly Tyr Ser Thr Gln Thr Ala Leu Thr Leu Lys Gln Lys
465                 470                 475                 480

Leu Ala Lys Ile Gly Gly Tyr Thr Lys Lys Val Cys Val Met Thr Lys
                485                 490                 495

Ile Phe Tyr Leu Ser Pro Glu Gly Met Thr Ser Cys Gln Tyr Asp Leu
            500                 505                 510

Arg Ser Gln Val Ile Tyr Pro Glu Ser Tyr Tyr Phe Thr Arg Arg Lys
```

```
                515                 520                 525
Tyr Leu Leu Lys Ala Leu Phe Lys Ala Leu Lys Arg Leu Lys Ser Leu
    530                 535                 540

Arg Asp Gln Phe Ser Phe Ala Glu Asn Leu Tyr Gln Ile Ile Gly Ile
545                 550                 555                 560

Asp Cys Phe Gln Lys Asn Asp Lys Lys Met Phe Lys Ser Cys Arg Arg
                565                 570                 575

Leu Thr

<210> SEQ ID NO 8
<211> LENGTH: 8080
<212> TYPE: DNA
<213> ORGANISM: Homo sapiens

<400> SEQUENCE: 8
```

| | | | | | |
|---|---|---|---|---|---|
| ttttggcttc | tgccctcaac | caaaatggcg | ctagctcgga | agctgccgag | gtgctaggag | 60 |
| ttgccgaagc | aagtccggaa | gctaccgagc | gagtccggaa | gttgccgaaa | gggagcagcg | 120 |
| gggaaggagg | atggcggata | tcatcgcaag | actccgggag | gacgggatcc | aaaaacgtgt | 180 |
| gatacaggaa | ggccgaggag | agctcccgga | ctttcaagat | gggaccaagg | ttcgtgtcta | 240 |
| ccctaccctt | ctcccctct | gcggcgtggt | gcgcatgcga | ggcgggagga | ggccttaggc | 300 |
| gagaggttgc | gcatgcccag | agggcagcgt | ccactgcccc | taccgctcac | atgcagaact | 360 |
| cgacgctgat | tgggctgaat | ttaagtaggg | ggtgaattcg | ggcctgtctg | ccccgccccc | 420 |
| tggctcggcc | ttgtagcagc | attggtgggg | gaggccgtca | gtcatcacaa | gcgggttggg | 480 |
| gttgggggtt | gatctcagtg | cttgggcaga | ccccacgctg | gaggaaaccc | agggccggga | 540 |
| gtggtcctcg | ggtatctggg | tttcaaggct | catgatcctt | tgtagatgga | agggccttct | 600 |
| gaaaacactt | agaccaactg | ccgctgttta | gagtggaaaa | ccaagaccct | gggacgtgca | 660 |
| aagccggaga | acgggcccag | aggtcaggtc | tcccagacag | ggactcttta | gcagccttcc | 720 |
| tgctgcacta | ggggcttgtt | gggacagatg | agggttggga | agtaaagaac | ctcccacttt | 780 |
| tctccttttt | gccaggcccc | cagatccagc | ccctctgccc | gcttctcccc | caacctacaa | 840 |
| ctccaggctt | ccctgcttct | cctgtagttg | cctcctcccg | gagtgctttt | cccagctgcc | 900 |
| acttgtttgc | agagtaggga | acctcccagg | ggcagcccct | gtgcccagca | gagcagtcag | 960 |
| gcaggacatg | cacattgagc | aaatgagcac | atgcccctg | gccagcaccg | tgccgaatcg | 1020 |
| ggcagctaag | catcctagcc | cagtgcagta | taagtgccct | gagagcagag | gggagctgca | 1080 |
| tggctggagt | gatccgctgt | atgaaaagat | atcttctcta | agaagagaca | ggatgtgtgg | 1140 |
| tgtgggttca | tgccccatg | tgctgggggg | ttggtggcgt | tggaagaagg | ggctggcaag | 1200 |
| ggggatcctg | gatggaacag | acatcagaag | gagagatgtg | aacaatggca | ccccaagatc | 1260 |
| agaaacaggt | ggtgttaaat | aaccaatcgc | cagcactgat | tgagtgctca | ctattcgaac | 1320 |
| attgtgctac | atgcttcaca | cgtttatttc | ctacaatgtg | agataggtac | tgttgttgat | 1380 |
| tccgttttac | cgatgtggaa | actgacttca | gagatgcagc | atggtgcggc | agttaagagc | 1440 |
| gtgggctcct | ctaaccatat | cctgtcgaga | gttcaatctc | caaacctctt | ttctctgcac | 1500 |
| ccaccccag | tgttatctct | aaaaactctc | cctgcccgga | ttactcccag | atgcagctct | 1560 |
| ccagtcatta | actgtctctt | aaacctgata | tatagctccc | tactcaccat | atccacctgg | 1620 |
| aagcctggtt | ggcaactcac | acttaacctg | ctccacctga | ggcttctccg | tgtcagggga | 1680 |
| accaacaacc | ttcccgttgt | tcagggcaaa | aaccttagca | tctctgtggt | cctcccagtc | 1740 |

```
tcacatccaa catcacatcc tcaatatcca gccaggatct gagttctcac cacttctgcc    1800
atcactgctt gggtccaggc catcctcatc tccagcctgg gttactgcag cgacctctaa    1860
ctctcctgcc tcttttgtcc ctctgtggtc tgttctcgtc ccagcagccg agcccatgcc    1920
agattcaatt cctttttgc tcggagccac tcagtggctt ccatcacaga gtgaaaaaca     1980
gaggcctcac catagcctac aggccctgtg aggtccaccc ctactgacct gggtgagctc    2040
ccctgctgac cctgtggtgt accccacccc ctccttcact ctgctctgcc acactggcat    2100
tgctgctctt gaacacatca tgcatttgaa acgggaagtt cccttgtctc cctcgcaggg    2160
cgtgcgatgg gggagtggct cgcttcttca gtgccccgct gctcagacct ctgggggagc    2220
atacagatgg gcaggctgtg ggctccgacc tcatggcagt gtctaggggt gaatatttac    2280
agctccgtgt gttctagggt gctcttttag tttgtctatg ggaggcttgt gttaaccagc    2340
tcaattagac ccccttcctt atcacaagga cagagggctt tctgtagtct ggggttttct    2400
tgccttgatg tactgagta ctggagaatt agatcacttg tgggcttgga gaatgattgc     2460 aaatttttt ttattttta ttttatttt ttttctgag atggagtttc actcttgttg        2520
cccaggctgg agtgcaatgg cacaatctct gcctcccagg ttcaagcaat tctcctgcct    2580
cagcctccca gtagctgag attacatgtg cctgacacca ggcccggcta atttttaaaa     2640
atgtttttag tagagatggg cttttaccat gttggccaag ctggtttcaa acgccttttt    2700 tttttttt tttttgaga cggagtcttg ctctattgcc caagctggag tgcagtggca      2760
tgatctcggt tcactgcaac ctccaccttc tgggttcaag tgattctcct gcctcagcct    2820
cccaagtagc tgggattaca ggcacccgcc atcatggcca gctaattttt gtattttag    2880 tagagacggg gttttgccac attggccagg ctggtcttga actcctgacc tcaggtgatc    2940
cacccgcctt ggagatggtc ttccctggg gttgggccac ttggtggccc cacctctcct    3000
ctgactgccc cagccaaact ccgcctcttc ctgccagttg atgacctgcc agcgtgcagg    3060
tgcctgtcag tgtgatcttc tgcttcttgc tccctgaca tcctctcaat gaccaggagc     3120
tcgtcttctg ctgatgggct cctctgacat ctggctgcct gtgggtctac cccctagggg    3180
tgttgggttt ttataggcac aggataggg tgtggcaggc cagggtggtc ttgggaaatg     3240
caacatttgg gcaggaaatg cctgttctca cctaggtctg tggggtgga accctaccca     3300 gggaccacgc cctcctctac ccagcacttc ccttctcccc ttccaaatta tttaacagga    3360
ccatgctcct cccttcccag cacttccata tcacattgtc ccactgcaag gcttttttac    3420
acatgctgtt cttttggcct agaaagttcc tatcccaggg tccacttggc ttgctttctt    3480
ccttactccc caaccccca ctctgtttaa tccagcccca accctcttgc cctgctgttt     3540
cccaagcacg tggcttcacc tgccatgaca tattgttttg tttgatgccc atctcctccc    3600
tctagaagcg ccatgtgagc tccagggggg cagggacttt tttgtgtttt gcttgctgcc    3660
atgttctggt gtctagcaca gagcttgggc acatagtagg tgcttagtaa atatctgttg    3720
aggaatgact ggagtcagac tgcttggact cttgttccca ctcagccacc cactagccgt    3780
gtggcttggg cctattcctc ccctccttgt ggctttgttt tctcaccagc gtgggaggat    3840
gaagccaggt gtaaggtcag gtggtgtccc cggggaagcc ccgtccctta tgccgtctgc    3900
aggccgggga ctggacttct ccttgggggt cagggtgagg gtttgtgcct ttgcctgacc    3960
tcgcatgtgg cccacaggcc acgttccact accggacgct gcacagtgac gacgagggca    4020
ccgtgctgga cgacagccgg gctcgtgca agcccatgga gctcatcatt ggcaagaagt     4080
tcaagctgcc tgtgtgggag accatcgtgt gcaccatgcg agaaggggag attgcccagt    4140
```

```
tcctctgtga catcaaggtg tctgtcctgt acctgtctgc ggtggctgtc cagccaagcc    4200
ctattcctat tccctatccc cagggctcct cctccctcca ccctctgcta gactgccacc    4260
cgctttcttt ttttttttga gatggagtct tgctctgtcg cccaggctgg agtgcagtgg    4320
tacgatctca gctcactgca ccctccacct cctgggttca gcgattctt ctgcctcagc     4380
ctcccgagta gctgggatta caaacacccg ccatgatgcc tggctaattt ttgtattttt    4440
agtagagaca gggtttcacc atgttggcca ggctggtctt gaacacctga cctcaggtga    4500
tccacccgcc ttggcctccc aaagtgctgg gattataggc gtgtgccacc gcgcccggcc    4560
cacccactct ttccagacca ccacaccagc ctgctgatgg cgtcctggcc tccattccgc    4620
cttcccctat tagccagact gaggccaggg gactcgttct caaatgcaaa tgacctgtac    4680
atcccttttgt ttcaaacctc tatgactcct ggtcactgta aggatagagc acaggggtc    4740
ctcacttcat gttgctgata cattcttgga aactgtgact aagagaaaaa acatacatca    4800
ggttttttct cagccaccgt catttctctc agcaaaattt tgttagaaca ttgatgagaa    4860
gaaaaattgg tttcgttatg tattgtttcg cctacagtca cagtttccaa gaacctactt    4920
aggacgttaa gtgaggactt aaaccgtata agctatagct gctcacatag ctttttgggg    4980
gctggcccct gccgtctcac cctcttactc aacctccctg cttttccttt ccattcccct    5040
tcttagccaa gatcttccct cttccttcaa agcttattcc tgggtcacca cctctaggaa    5100
gccctccctg actgctagtg gttggctcaa ctcccatgtt tgggtcctcc aaccctcatg    5160
ccctgcatgg ccaggatctg ctcttctgcc ttgtcctagg ctattgcaga gcagggatct    5220
ggcctgttta cttctagctt tgggatgccc agcgcgagcc agtccagagc caagactcag    5280
gaaatgcccg ctgatggcag cccggcagtc agccctgtc cagacaacag ggcagtggga     5340
ggagtgggga ggacccgggt aggaggaatc tggttatctg gttcccacca gcctagcagc    5400
tttgccaagc aagagattag aggctaggtc ccctatgcct gtctccctgt ggggtttttt    5460
tttttttgac taagtctcac tctgttgccc aggctggagt gcagtggcgt gatcttggct    5520
cactgcaacc accatctcct gggttcagct gattctctgc cttagctgcc tgagtagctg    5580
ggattacagg cacctgccat cgtgcccggc tcatttttgt attttagcag agacgcggtt    5640
tcaccatgtt ggtcaggctg gtcttgaact cctgacctca ggtgatccgc ccgccttggc    5700
ctcccgaagt gctaggatta caggcgtgag ccaccacatc cggcctccct gagggttttg    5760
aagtggctgg cctgggccca gctctgaggt aggccctcag tggggtgtgg gtggggcaga    5820
aggaggagct gctgggaaca gaatgtgggg ggccccagtt cttttgcatag tccagcaaag    5880
ggccttatcc tctggaggga gaggaggtaa gaattctact gggcctgtaa ggaccaggga    5940
gacaggggtt gatggtaggc atgtgtctgt ggtgggggtg aggaggggt taggtgctct     6000
gtttggtggc cagagaatgt ggcagaagct ggggcttcac caggagagag ggctgagcga    6060
ctggaggagt cctgaattaa aagcctcctg tgcttaaacg gagtagggtc ccagttgtca    6120
ctctctgggc cttggtgttt gttctcagat ggtggtgggg aaggggggctg ggccttgtgg   6180
acccggtgac cagccagccc acggtgacag agccccggc gcccttgcct tcccgcagca    6240
tgtggtcctg tacccgctgg tggccaagag tctccgcaac atcgcggtgg gcaaggaccc    6300
cctggagggc cagcggcact gctgcggtgt tgcacagatg cgtgaacaca gctccctggg    6360
ccatgctgac ctgacgcccc tgcagcagaa ccccagccc ctcatcttcc acatggagat     6420
gctgaaggtg agggggccacc gcgcctggtc tcaccaggcc cccactgccc agcctcaggg    6480
```

```
cggcgctggc ctgtccaccc aggggtggtg ggatccgcag gtggactgct ggggagcgg      6540 acagagacaa gaaaacctgt gcaggaccct tggcagtacc ctgggtctcc tttcctcctc     6600
cttcacatct caaatgtcac ctcctccagg aaaccggccc tgcccacccg gtctcctcat     6660
tctctgtctc gcagcagctc atttccttta tagcctctgc cgcaccttga agtcccttgg     6720
aattcatgga tttccttgtc catttaggga acctgccatg cagcatgatc tctgcgaggg     6780
cagggctttt caccgtcttg ttcactgttc tattcttagc acttggcaca gtgctgggca     6840
cacaggagat gtgacatcga tgtttgatgc tttttgagtg acaagtagct ctgctgctgg     6900
tgtgtgatgt ctgggggccc agccagccca gatgtgggtc aggtctgctg ctgacggacg     6960
cagctgtggt gtccccgagc cccgctgtga tatgccccat gccctgcagg tggagagccc     7020
tggcacgtac cagcaggacc catgggccat gacagacgaa gagaaggcaa aggcagtgcc     7080
acttatccac caggagggca accggttgta ccgcgagggg catgtgaagg aggctgctgc     7140
caagtactac gatgccattg cctgcctcaa gaacctgcag atgaaggtac tgcctggagg     7200 ctgagggga ggatggatgg aggggggtgt ggagccaggg ggcccaggtc tacagcttct     7260
ccccgctccc tgcccccata ctcccaggaa cagcctgggt ccctgaatg gatccagctg      7320 gaccagcaga tcacgccgct gctgctcaac tactgccagt gcaagctggt ggtcgaggag     7380
tactacgagg tgctggacca ctgctcttcc atcctcaaca gtacgacgg tgagcaccgg     7440 gccctgggct gccgggggct gcgagtggtc agagagtggc ctttctcctg tcactgctgg     7500
ggtcaagacc tagccttca caaccccat tctgagctcc cacgggggcc tgactaaatg       7560
cctctactcg gcagggctgt gggccccatt gtgccaatga agcatgaatg gtgtattggg     7620
ggtggggtgg catcctcagg tcagggaggg ctctctctcc cctgtgggcc catggtgcca     7680
ggagacatga gggcaggcag ctggccagga tcccccctca tgcccttgca tgcccactgc     7740
ccactggcct cccctgcaga caacgtcaag gcctacttca gcggggcaa ggcccacgcg      7800 gccgtgtgga atgcccagga ggcccaggct gactttgcca aagtgctgga gctgacccca    7860
gccctggcgc ctgtggtgag ccgagagctg caggccctgg aggcacggat ccggcagaag    7920
gacgaagagg acaaagcccg gttccgggg atcttctccc attgacagga gcacttggcc     7980
ctgccttacc tgccaagccc actgctgcag ctgccagccc ccctgcccgt gctgcgtcat    8040
gcttctgtgt atataaaggc ctttatttat ctctctctga                          8080
```

<210> SEQ ID NO 9
<211> LENGTH: 330
<212> TYPE: PRT
<213> ORGANISM: Homo sapiens

<400> SEQUENCE: 9

```
Met Ala Asp Ile Ile Ala Arg Leu Arg Glu Asp Gly Ile Gln Lys Arg
1               5                   10                  15

Val Ile Gln Glu Gly Arg Gly Glu Leu Pro Asp Phe Gln Asp Gly Thr
            20                  25                  30

Lys Ala Thr Phe His Tyr Arg Thr Leu His Ser Asp Asp Glu Gly Thr
        35                  40                  45

Val Leu Asp Asp Ser Arg Ala Arg Gly Lys Pro Met Glu Leu Ile Ile
    50                  55                  60

Gly Lys Lys Phe Lys Leu Pro Val Trp Glu Thr Ile Val Cys Thr Met
65                  70                  75                  80

Arg Glu Gly Glu Ile Ala Gln Phe Leu Cys Asp Ile Lys His Val Val
                85                  90                  95
```

Leu Tyr Pro Leu Val Ala Lys Ser Leu Arg Asn Ile Ala Val Gly Lys
            100                 105                 110

Asp Pro Leu Glu Gly Gln Arg His Cys Cys Gly Val Ala Gln Met Arg
        115                 120                 125

Glu His Ser Ser Leu Gly His Ala Asp Leu Asp Ala Leu Gln Gln Asn
130                 135                 140

Pro Gln Pro Leu Ile Phe His Met Glu Met Leu Lys Val Glu Ser Pro
145                 150                 155                 160

Gly Thr Tyr Gln Gln Asp Pro Trp Ala Met Thr Asp Glu Lys Ala
            165                 170                 175

Lys Ala Val Pro Leu Ile His Gln Glu Gly Asn Arg Leu Tyr Arg Glu
                180                 185                 190

Gly His Val Lys Glu Ala Ala Lys Tyr Tyr Asp Ala Ile Ala Cys
            195                 200                 205

Leu Lys Asn Leu Gln Met Lys Glu Gln Pro Gly Ser Pro Glu Trp Ile
        210                 215                 220

Gln Leu Asp Gln Gln Ile Thr Pro Leu Leu Asn Tyr Cys Gln Cys
225                 230                 235                 240

Lys Leu Val Val Glu Glu Tyr Tyr Glu Val Leu Asp His Cys Ser Ser
                245                 250                 255

Ile Leu Asn Lys Tyr Asp Asp Asn Val Lys Ala Tyr Phe Lys Arg Gly
            260                 265                 270

Lys Ala His Ala Ala Val Trp Asn Ala Gln Glu Ala Gln Ala Asp Phe
        275                 280                 285

Ala Lys Val Leu Glu Leu Asp Pro Ala Leu Ala Pro Val Val Ser Arg
    290                 295                 300

Glu Leu Gln Ala Leu Glu Ala Arg Ile Arg Gln Lys Asp Glu Asp
305                 310                 315                 320

Lys Ala Arg Phe Arg Gly Ile Phe Ser His
            325                 330

<210> SEQ ID NO 10
<211> LENGTH: 12695
<212> TYPE: DNA
<213> ORGANISM: Homo sapiens

<400> SEQUENCE: 10
cgcgccgggg cctggtgctc ggtcggcggg tgctgccgct ttaagcgggg gcgggactgc    60
gcgcggccga gcggttgcga cgagggctcg gctgggggtc gccggggtcg cgggccgggc   120
ctgcaggagc cgggccgccg aggtcggggc tggttgaact catggacctg atactttttct   180 cttgagaagc aaaccagccc aaaagaaaaa tggcgtttgt tgcaacacag ggggccacgg   240
tggttgacca gaccactttg atgaaaaagt accttcagtt tgtggcagct ctcacagatg   300
tgaatacacc tgatgaaaca agttgaaaa tgatgcaaga agttagtgaa aattttgaga   360
atgtcacgtc atctcctcag tattctacat tcctagaaca tatcatccct cgattcctta   420
catttctcca agatggagaa gttcagtttc ttcaggagaa accagcacag caactgcgga   480
agctcgtact tgaaataatt catagaatac caaccaacga acatcttcgt cctcacacaa   540
aaaatgtttt gtctgtgatg tttcgctttt tagagacgga aaatgaagaa atgttctta   600 tttgtctaag aataattatt gagctacaca acagttcag gccaccgatc acacaagaaa   660
ttcatcattt tctggatttt gtgaaacaga tttacaagga gcttccaaaa gtagtgaacc   720
gctactttga gaaccctcaa gtgatccccg agaacacagt gcctccccca gaaatggttg   780

```
gtatgataac aacgattgct gtgaaagtca acccggagcg tgaggacagt gagactcgaa      840
cacattccat cattccgagg ggatcacttt ctctgaaagt gttggcagaa ttgcccatta      900
ttgttgtttt aatgtatcag ctctacaaac tgaacatcca caatgttgtt gctgagtttg      960
tgcccttgat catgaacacc attgccattc aggtgtctgc acaagcgagg caacataagc     1020
tttacaacaa ggagttgtat gctgacttca ttgctgctca gattaaaaca ttgtcatttt     1080
tagcttacat tatcaggatt taccaggagt tggtgactaa gtattctcag cagatggtga     1140
aaggaatgct ccagttactt tcaaattgtc cagcagagac tgcacacctc agaaaggagc     1200
ttctgattgc tgccaaacac atcctcacca cagagctgag aaaccagttc attccttgca     1260
tggacaagct gtttgatgaa tccatactaa ttggctcagg atatactgcc agagagactc     1320
taaggcccct cgcctacagc acgctggccg acctcgtgca ccatgtccgc cagcacctgc     1380
ccctcagcga cctctccctc gccgtccagc tcttcgccaa gaacatcgac gatgagtccc     1440
tgcccagcag catccagacc atgtcctgca agctcctgct gaacctggtg gactgcatcc     1500
gttccaagag cgagcaggag agtggcaatg ggagagacgt cctgatgcgg atgctggagg     1560
ttttcgttct caaattccac acaattgctc ggtaccagtc tctgccattt tttaagaagt     1620
gtaagcctca gtcagaactt ggagccgtgg aagcagctct gcctggggtg cccactgccc     1680
ctgcagctcc tggccctgct ccctccccag cccctgtccc tgcccacct ccaccccgc     1740 ccccaccccc acctgccacc cctgtgaccc cggcccccgt gcctcccttc gagaagcaag     1800
gagaaaagga caaggaagac aagcagacat tccaagtcac agactgtcga agtttggtca     1860
aaaccttggt gtgtggtgtc aagacaatca cgtggggcat aacatcatgc aaagcacctg     1920
gtgaagctca gttcattccc aacaagcagt tacaacccaa agagacacag atttacatca     1980
aacttgtgaa atatgcaatg caagctttag atatttatca ggtccagata gcaggaaatg     2040
gacagacata catccgtgtg gccaactgcc agactgtgag aatgaaagag gagaaggagg     2100
tattggagca tttcgctggt gtgttcacaa tgatgaaccc cttaacgttc aaagaaatct     2160
tccaaactac ggtccttat atggtggaga aatctcaaa aaattatgct cttcagattg     2220
ttgccaattc cttcttggca aatcctacta cctctgctct gtttgctacg attctggtgg     2280
aatatctcct tgatcgcctg ccagaaatgg gctccaacgt ggagctctcc aacctgtacc     2340
tcaagctgtt caagctggtc tttggctctg tctccctctt tgcagctgaa atgaacaaa     2400 tgctgaagcc tcacttgcac aagattgtga acagctctat ggagctcgcg cagactgcca     2460
aggaacccta caactacttc ttgctgctac gggcgctgtt tcgctctatt ggtggaggta     2520
gccacgatct cttgtatcag gagttcttgc ctctccttcc aaacctcctg caagggctga     2580
acatgcttca gagtggcctg cacaagcagc acatgaagga cctctttgtg gagctgtgtc     2640
tcaccgtccc tgtgcggctg agctcgcttt tgccgtacct gcccatgctt atggatccct     2700
tggtgtctgc actcaatggg tctcagacat tggtcagcca aggcctcagg cgctggagc     2760 tgtgtgtgga caacctgcag cccgacttcc tctacgacca catccagccg gtgcgcgcag     2820
agctcatgca ggctctgtgg cgcaccttac gcaaccctgc tgacagcatc tcccacgtgg     2880
cctaccgtgt gctcggtaag tttggcggca gtaacaggaa gatgctgaag gagtcgcaga     2940
agctgcacta cgttgtgacc gaggttcagg gccccagcat cactgtggag ttttccgact     3000
gcaaagcttc tctccagctc cccatggaga aggccattga aactgctctg gactgcctga     3060
aaagcgccaa cactgagccc tactaccgga ggcaggcgtg ggaagtgatc aaatgcttcc     3120
```

```
tggtggccat gatgagcctg gaggacaaca agcacgcact ctaccagctc ctggcacacc      3180
ccaactttac agaaaagacc atccccaatg ttatcatctc acatcgctac aaagcccagg      3240
acactccagc ccggaagact tttgagcagg ccctgacagg cgccttcatg tctgctgtca      3300
ttaaggacct gcggcccagc gccctgccct tgtcgccag cttgatccgc cactatacga      3360
tggtggcagt cgcccagcag tgtggccctt tcttgctgcc ttgctaccag gtgggcagcc      3420
agcccagcac agccatgttt cacagtgaag aaaatggctc gaaaggaatg gatcctttgg      3480
ttctcattga tgcaattgct atttgtatgg catatgaaga aaaggagctt tgcaaaatcg      3540
gggaggtggc cctagctgtg atatttgatg ttgcaagtat catcctgggc tccaaggaga      3600
gggcctgcca gctgcccctg ttttcttaca tcgtggagcg cctgtgtgca tgttgttatg      3660
aacaggcgtg gtatgcaaag ctgggggtg tggtgtctat taagtttctc atggagcggc      3720
tgcctctcac ttgggttctc cagaaccagc agacattcct gaaagcactt ctctttgtca      3780
tgatggactt aactggagag gtttccaatg gggcagtcgc tatggcaaag accacgctgg      3840
agcagcttct gatgcggtgc gcaacgcctt aaaagacga ggagagagcc gaagagatcg      3900
tggccgccca ggaaaagtct ttccaccatg tgacacacga cttggttcga gaagtcacct      3960
ctccaaactc cactgtgagg aagcaggcca tgcattcgct gcaggtgttg gcccaggtca      4020 ctggaagag tgtcacggtg atcatggaac cccacaaaga ggtcctgcag gatatggtcc      4080
cccctaagaa gcacctgctc cgacaccagc ctgccaacgc acagattggc ctgatggagg      4140
ggaacacgtt ctgtaccacg ttgcagccca ggctcttcac aatggacctt aacgtggtgg      4200
agcataaggt gttctacaca gagctgttga atttgtgtga ggctgaagat tcagctttaa      4260
caaagctgcc ctgttataaa agccttccgt cactcgtacc tttacgaatt gcggcattaa      4320
atgcacttgc tgcctgcaat taccttcctc agtccaggga gaaaatcatc gctgcactct      4380
tcaaagccct gaattccacc aatagtgagc tccaagaggc cggagaagcc tgtatgagaa      4440
agtttttaga aggtgctacc atagaagtcg atcaaatcca cacacatatg cgacctttgc      4500
tgatgatgct gggagattac cggagcttga cgctgaatgt tgtgaatcgc ctgacttcgg      4560
tcacgaggct cttcccaaat tccttcaatg ataaattttg tgatcagatg atgcaacatc      4620
tgcgcaagtg gatggaagtg gtggtgatca cccacaaagg gggccagagg agcgacggaa      4680
acgaaagcat ttccgagtgc gggagatgtc ccttgtctcc attctgtcag tttgaggaaa      4740
tgaagatttg ctcagcaatt ataaaccttt ttcatctgat cccggctgct cctcagacac      4800
tggtgaagcc tttgctagag gttgtcatga aaacggagcg ggcgatgctg atcgaggcgg      4860
ggagtccatt ccgagagccc ctgatcaagt tcctgactcg acatccctcg cagacagtgg      4920
agctgttcat gatggaagcc acactgaacg atccccagtg gagcagaatg tttatgagtt      4980
ttttaaaaca caaagacgcc agacctctgc gggatgtgct ggctgccaac cccaacaggt      5040
tcatcaccct gctgctgccg gggggtgccc agacggctgt gcgccccggt tcgcccagca      5100
ccagcaccat gcgcctggac ctccagttcc aggccatcaa gatcataagc attatagtga      5160
aaaacgatga ctcctggctg gccagccagc actctctggt gagccagttg cgacgtgtgt      5220
gggtgagtga gaacttccaa gagaggcacc gcaaggagaa catggcagcc accaactgga      5280
aggagcccaa gctgctggcc tactgcctgc tgaactactg caaaaggaat tacggagata      5340
tagaattgct gttccagctg ctccgagcct ttactggtcg ttttctctgc aacatgacat      5400
tcttaaaaga gtatatggag gaagagattc ccaaaaatta cagcatcgct cagaaacgtg      5460
ccctgttctt tcgctttgta gacttcaacg accccaactt cggagatgaa ttaaaagcta      5520
```

-continued

```
aagttctgca gcatatcttg aatcctgctt tcttgtacag ctttgagaag ggggaaggag    5580
agcagctctt gggacctccc aatccagaag gagataaccc agaaagcatc accagtgtgt    5640
ttattaccaa ggtcctggac cccgagaagc aggcggacat gctggactcg ctgcggatct    5700
acctgctgca gtacgccacg ctgctggtgg agcacgcccc ccaccacatc catgacaaca    5760
acaagaaccg caacagcaag ctgcgccgcc tcatgacctt cgcctggccc tgcctgctct    5820
ccaaggcctg cgtgggccca gcctgcaagt acagcggaca cttgctcctg cgcacatta    5880
tcgccaaatt cgccatacac aagaagatcg tcctgcaggt ttttcatagt ctcctcaagg    5940
ctcacgcaat ggaagctcga gcgatcgtca gacaggcgat ggccattctg accccggcgg    6000
tgccggccag gatggaggac gggcaccaga tgctgaccca ctggacccgg aagatcattg    6060
tggaggaggg gcacaccgtc ccgcagctgg tccacattct gcacctgata gtgcaacact    6120
tcaaggtgta ctacccggta cggcaccact ggtgcagca catggtgagc gccatgcaga    6180
ggctgggctt cacgcccagt gtcaccatcg agcagaggcg gctggccgtg gacctgtctg    6240
aagtcgtcat caagtgggag ctgcagagga tcaaggacca gcagccggat tcagatatgg    6300
acccaaattc cagtggagaa ggagtcaatt ctgtctcatc ctccattaag agaggcctgt    6360
ccgtggattc tgcccaggaa gtgaaacgct ttaggacggc caccggagcc atcagtgcag    6420
tctttgggag gagccagtcg ctacctggag cagactctct cctcgccaag cccattgaca    6480
agcagcacac agacactgtg gtgaacttcc ttatccgcgt ggcctgtcag gttaatgaca    6540
acaccaacac agcggggtcc cctggggagg tgctctctcg ccggtgtgtg aaccttctga    6600
agactgcgtt gcggccagac atgtggccca agtccgaact caagctgcag tggttcgaca    6660
agctgctgat gactgtggag cagccaaacc aagtgaacta tgggaatatc tgcacgggcc    6720
tagaagtgct gagcttcctg ctaactgtcc tccagtcccc agccatcctc agtagcttca    6780
aacctctgca gcgtggaatt gccgcctgca tgacatgtgg aaacaccaag gtgttgcgag    6840
ccgtccacag ccttctctcg cgcctgatga gcattttccc aacagagccg agtacttcca    6900
gtgtggcctc caaatatgaa gagctggagt gcctctacgc agccgtcgga aaggtcatct    6960
atgaagggct caccaactac gagaaggcca ccaatgccaa tccctcccag ctcttcggga    7020
cccttatgat cctcaagtct gcctgcagca caaccccag ctacatagac aggctgatct    7080
ccgtctttat gcgctccctg cagaagatgg tccgggagca tttaaaccct caggcagcgt    7140
caggaagcac cgaagccacc tcaggtacaa gcgagctggt gatgctgagt ctggagctgg    7200
tgaagacgcg cctggcagtg atgagcatgg agatgcggaa gaacttcatc caggccatcc    7260
tgacatccct catcgaaaaa tcaccagatg ccaaaatcct ccgggctgtg gtcaaaatcg    7320
tggaagaatg ggtcaagaat aactccccaa tggcagccaa tcagacacct acactccggg    7380
agaagtccat tttgcttgtg aagatgatga cttacataga aaaacgcttt ccggaagacc    7440
ttgaattaaa tgcccagttt ttagatcttg ttaactatgt ctacagggat gagaccctct    7500
ctggcagcga gctgacggcg aaacttgagc ctgcctttct ctctgggctg cgctgtgccc    7560
agccactcat cagggcaaag tttttcgagg tttttgacaa ctccatgaaa cgtcgtgtct    7620
acgagcgctt gctctatgtg acctgttcgc agaactggga agccatgggg aaccacttct    7680
ggatcaagca gtgcattgag ctgcttctgg ccgtgtgtga agagcacc cccattggca    7740
ccagctgcca aggagccatg ctcccgtcca tcaccaacgt catcaacctg ccgatagcc    7800
acgaccgtgc cgccttcgcc atggtcacac atgtcaagca ggagcccgg gagcgggaga    7860
```

```
acagcgagtc caaagaggag gatgtagaga tagacatcga actagctcct ggggatcaga   7920
ccagcacgcc caaaaccaaa gaactttcag aaaaggacat tggaaaccag ctgcacatgc   7980
taaccaacag gcacgacaag tttctggaca ctctccgaga ggtgaagact ggagcgctgc   8040
tcagcgcttt cgttcagctg tgccacattt ccacgacgct ggcagagaag acgtgggtcc   8100
agcttttccc cagattgtgg aagatcctct ctgacagaca gcagcatgca ctcgcgggtg   8160
agataagtcc atttctgtgc agcggcagtc accaggtgca gcgggactgc cagcccagcg   8220
cgctgaactg ctttgtggaa gccatgtccc agtgcgtgcc gccaatcccc atccgaccct   8280
gcgtcctgaa gtacctgggg aagacacaca acctctggtt ccggtccacg ctgatgttgg   8340
agcaccaggc ttttgaaaag ggtctgagtc ttcagattaa gccgaagcaa acaacggagt   8400
tttatgagca ggagagcatc accccgccgc agcaggagat actggattcc cttgcggagc   8460
tttactccct gttacaagag gaagatatgt gggctggtct gtggcagaag cggtgcaagt   8520
actcggagac agcgactgcg attgcttacg agcagcacgg gttctttgag caggcacaag   8580
aatcctatga aaaggcaatg gataaagcca aaaagaaca tgagaggagt aacgcctccc   8640
ctgctatttt ccctgaatac cagctctggg aagaccactg gattcgatgc tccaaggaat   8700
tgaaccagtg ggaagccctg acggagtacg gtcagtccaa aggccacatc aacccctacc   8760
tcgtcctgga gtgcgcctgg cgggtgtcca actggactgc catgaaggag gcgctggtgc   8820
aggtggaagt gagctgtccg aaggagatgg cctggaaggt gaacatgtac cgcggatacc   8880
tggccatctg ccaccccgag gagcagcagc tcagcttcat cgagcgcctg gtggagatgg   8940
ccagcagcct ggccatccgc gagtggcggc ggctgcccca cgtagtgtcc cacgtgcaca   9000
cgcctctcct acaggcagcc cagcaaatca tcgaactcca ggaagctgca caaatcaacg   9060
caggcttaca gccaaccaac ctgggaagga acaacagcct gcacgacatg aagacggtgg   9120
tgaagacctg gaggaaccga ctgcccatcg tgtctgacga cttgtcccac tggagcagca   9180
tcttcatgtg gaggcagcat cattaccagg gtaaaccgac ctggtccggc atgcattcat   9240
catcgattgt aactgcctat gagaatagct ctcagcatga tcccagttca aataacgcta   9300
tgcttggggt tcatgcatca gcttcagcga tcatccagta tggaaaaatc gcccggaaac   9360
aaggactggt caatgtagct ctggatatat taagtcggat tcatactatt ccaactgttc   9420
ctatcgtgga ttgcttccag aagattcgac agcaagttaa atgctacctc cagctggcag   9480
gcgtcatggg caaaaacgag tgcatgcagg gccttgaagt tattgaatct acaaatttaa   9540
aatacttcac aaaagagatg acagccgaat tttatgcact gaagggaatg ttcttggctc   9600
agatcaacaa gtccgaggag gcaaacaaag ccttctctgc agctgtgcag atgcacgatg   9660
tgctggtgaa agcctgggcc atgtgggcg actacctgga gaacatcttt gtgaaggagc   9720
ggcagctgca cctgggcgtg tctgccatca cctgctacct gcacgcctgc ggcatcaga   9780 acgagagcaa atcgaggaaa tacttagcca aggtgctgtg gcttttgagt tttgatgatg   9840
acaaaaacac tttggcagat gccgtcgaca agtactgcat tggtgtgcca cccatccagt   9900
ggctggcctg gatcccacag ctgctcacct gcctggttgg ctcggaggga agctgctct   9960 tgaacctcat tagccaggtt ggacgcgtgt atccccaagc ggtctacttt cccatccgga  10020
ccctgtacct gaccctgaaa atagaacagc gggaacgcta caagagcgat ccagggccca  10080
taagagcaac agcacccatg tggcgctgca gccgaatcat gcacatgcag cgagagctcc  10140
accccaccct tctgtcttcc ctggaaggca tcgtcgatca gatggtctgg ttcagagaaa  10200
attggcatga agaggttctc aggcagctcc aacagggcct ggcgaaatgt tactccgtgg  10260
```

```
cgtttgagaa aagtggagcg gtgtccgatg ctaaaatcac cccccacact ctcaattttg    10320
tgaagaagtt ggtgagcacg tttggggtgg gcctggagaa tgtgtccaac gtctcgacca    10380
tgttctccag cgcagcctct gagtctctgg cccggcgggc gcaggccact gcacaagacc    10440
ctgtctttca gaagctgaaa ggccagttca cgacggattt tgacttcagc gttccaggat    10500
ccatgaagct tcataatctt atttctaagt tgaaaagtg gatcaaaatc ttggaggcca    10560
agaccaagca actccccaaa ttcttcctca tagaggaaaa gtgccggttc ttgagcaatt    10620
tctcggcaca gacagctgaa gtggaaattc ctggggagtt tctgatgcca agccaacgc    10680
attattacat caagattgca cggttcatgc cccgggtaga gattgtgcag aagcacaaca    10740
ccgcagcccg gcggctgtac atccggggac acaatggcaa gatctaccca tacctcgtca    10800
tgaacgacgc ctgcctcaca gagtcacggc gagaggagcg tgtgttgcag ctgctgcgtc    10860
tgctgaaccc ctgtttggag aagagaaagg agaccaccaa gaggcacttg ttttcacag    10920
tgccccgggt tgtggcagtt tccccacaga tgcgcctcgt ggaggacaac ccctcttcac    10980
tttcccttgt ggagatctac aagcagcgct gcgccaagaa gggcatcgag catgacaacc    11040
ccatctcccg ttactatgac cggctggcta cggtgcaggc gcggggaacc caagccagcc    11100
accaggtcct ccgcgacatc ctcaaggagg ttcagagtaa catggtgccg cgcagcatgc    11160
tcaaggagtg ggcgctgcac accttcccca atgccacgga ctactggacg ttccggaaga    11220
tgttcaccat ccagctggct ctgataggct tcgcggaatt cgtcctgcat ttaaatagac    11280
tcaaccccga gatgttacag atcgctcagg acactggcaa actgaatgtt gcctactttc    11340
gatttgacat aaacgacgcg actggagacc tggatgccaa ccgtcctgtc ccatttcgac    11400
tcacgcccaa catttctgag tttctgacca ccatcggggt ctccggcccg ttgacagcgt    11460
ccatgattgc ggtcgcccgg tgcttcgccc agccaaactt taaggtggat ggcattctga    11520
aaacggttct ccgggacgag atcattgctt ggcacaaaaa aacacaagag gacacgtcct    11580
ctcctctctc ggccgccggg cagccagaga acatggacag ccagcaactg gtgtccctgg    11640
ttcagaaagc cgtcaccgcc atcatgaccg gcctgcacaa cctcgcccag ttcgaaggcg    11700
gggaaagcaa ggtgaacacc ctggtggccg cggcaaacag cctggacaat ctgtgccgca    11760
tggacccgc ctggcacccc tggctgtgac tgtggccgcc acggccaccc ggaatgtgaa    11820
gggcgctccg ggctctgagc ccgcagcttt tacgacttct ccctgcctcg ttccttatat    11880
tcacagaagc cccatagttt cactgggttg cggttatttt cctggtagtt tgcgtgtaag    11940
aaagggagaa tatagtttta gaggaagctg aactatgacg atgctgggcg aagcggttgg    12000
aaatggcaga gctgaaactt attccaagct ttcaaaataa tcttttaaga agccaggatt    12060
ctccggtctg gaatttctga gtgagtcctt tttttatggt gtcctccctc tgtgaatgta    12120
caggcggaac tgtacgaaca gctcccttcc atccattttt aactctttcg gaaataacac    12180
ctcacagcag cttcgtgctt ttgtacagac ctttgtaaca agtgtacaga aaactcattt    12240
tgtttgagaa acaggagttg atgaacccat catgctggtt tttctctgag cacaaagttt    12300
taggctgtac acagccagcc ttgggaatct cgttgagcgt tcggcgtgga tccacggggc    12360
caggccaccc tgcgggagcg ccacacgcat ccacttcgga ttcagtgggt gaagacgaaa    12420
ctctgagagt ctgcaggcgg ctcctgtgct ttttatttct ggctcttcgg atgtcttcta    12480
gacatttact atcactgcac ctgaagaaaa aatcactttt accttcctaa tttaaaaaga    12540
caaaacagaa atgtacgttc cttcgctagc tttagtcttt ctgttcccat ttttataaat    12600
```

```
ctgagcattg ataatgttct atctaaattt gtacagtgtg attttttttt ttagaataaa    12660
tattttataa aagggttaaa aaaaaaaaaa aaaaa                              12695
```

<210> SEQ ID NO 11
<211> LENGTH: 3858
<212> TYPE: PRT
<213> ORGANISM: Homo sapiens

<400> SEQUENCE: 11

```
Met Ala Phe Val Ala Thr Gln Gly Ala Thr Val Val Asp Gln Thr Thr
1               5                   10                  15

Leu Met Lys Lys Tyr Leu Gln Phe Val Ala Leu Thr Asp Val Asn
            20                  25                  30

Thr Pro Asp Glu Thr Lys Leu Lys Met Met Gln Glu Val Ser Glu Asn
        35                  40                  45

Phe Glu Asn Val Thr Ser Ser Pro Gln Tyr Ser Thr Phe Leu Glu His
    50                  55                  60

Ile Ile Pro Arg Phe Leu Thr Phe Leu Gln Asp Gly Glu Val Gln Phe
65                  70                  75                  80

Leu Gln Glu Lys Pro Ala Gln Gln Leu Arg Lys Leu Val Leu Glu Ile
                85                  90                  95

Ile His Arg Ile Pro Thr Asn Glu His Leu Arg Pro His Thr Lys Asn
            100                 105                 110

Val Leu Ser Val Met Phe Arg Phe Leu Glu Thr Glu Asn Glu Glu Asn
        115                 120                 125

Val Leu Ile Cys Leu Arg Ile Ile Ile Glu Leu His Lys Gln Phe Arg
    130                 135                 140

Pro Pro Ile Thr Gln Glu Ile His His Phe Leu Asp Phe Val Lys Gln
145                 150                 155                 160

Ile Tyr Lys Glu Leu Pro Lys Val Val Asn Arg Tyr Phe Glu Asn Pro
                165                 170                 175

Gln Val Ile Pro Glu Asn Thr Val Pro Pro Glu Met Val Gly Met
            180                 185                 190

Ile Thr Thr Ile Ala Val Lys Val Asn Pro Glu Arg Glu Asp Ser Glu
        195                 200                 205

Thr Arg Thr His Ser Ile Ile Pro Arg Gly Ser Leu Ser Leu Lys Val
    210                 215                 220

Leu Ala Glu Leu Pro Ile Ile Val Val Leu Met Tyr Gln Leu Tyr Lys
225                 230                 235                 240

Leu Asn Ile His Asn Val Val Ala Glu Phe Val Pro Leu Ile Met Asn
                245                 250                 255

Thr Ile Ala Ile Gln Val Ser Ala Gln Ala Arg Gln His Lys Leu Tyr
            260                 265                 270

Asn Lys Glu Leu Tyr Ala Asp Phe Ile Ala Ala Gln Ile Lys Thr Leu
        275                 280                 285

Ser Phe Leu Ala Tyr Ile Arg Ile Tyr Glu Leu Val Thr Lys
    290                 295                 300

Tyr Ser Gln Gln Met Val Lys Gly Met Leu Gln Leu Ser Asn Cys
305                 310                 315                 320

Pro Ala Glu Thr Ala His Leu Arg Lys Glu Leu Leu Ile Ala Ala Lys
                325                 330                 335

His Ile Leu Thr Thr Glu Leu Arg Asn Gln Phe Ile Pro Cys Met Asp
            340                 345                 350

Lys Leu Phe Asp Glu Ser Ile Leu Ile Gly Ser Gly Tyr Thr Ala Arg
```

```
                355                 360                 365
Glu Thr Leu Arg Pro Leu Ala Tyr Ser Thr Leu Ala Asp Leu Val His
370                 375                 380
His Val Arg Gln His Leu Pro Leu Ser Asp Leu Ser Leu Ala Val Gln
385                 390                 395                 400
Leu Phe Ala Lys Asn Ile Asp Asp Glu Ser Leu Pro Ser Ser Ile Gln
                405                 410                 415
Thr Met Ser Cys Lys Leu Leu Leu Asn Leu Val Asp Cys Ile Arg Ser
                420                 425                 430
Lys Ser Glu Gln Glu Ser Gly Asn Gly Arg Asp Val Leu Met Arg Met
                435                 440                 445
Leu Glu Val Phe Val Leu Lys Phe His Thr Ile Ala Arg Tyr Gln Leu
        450                 455                 460
Ser Ala Ile Phe Lys Lys Cys Lys Pro Gln Ser Glu Leu Gly Ala Val
465                 470                 475                 480
Glu Ala Ala Leu Pro Gly Val Pro Thr Ala Pro Ala Pro Gly Pro
                    485                 490                 495
Ala Pro Ser Pro Ala Pro Val Pro Ala Pro Pro Pro Pro Pro Pro
                500                 505                 510
Pro Pro Pro Ala Thr Pro Val Thr Pro Ala Pro Val Pro Pro Phe Glu
        515                 520                 525
Lys Gln Gly Glu Lys Asp Lys Glu Asp Lys Gln Thr Phe Gln Val Thr
    530                 535                 540
Asp Cys Arg Ser Leu Val Lys Thr Leu Val Cys Gly Val Lys Thr Ile
545                 550                 555                 560
Thr Trp Gly Ile Thr Ser Cys Lys Ala Pro Gly Glu Ala Gln Phe Ile
                    565                 570                 575
Pro Asn Lys Gln Leu Gln Pro Lys Glu Thr Gln Ile Tyr Ile Lys Leu
                580                 585                 590
Val Lys Tyr Ala Met Gln Ala Leu Asp Ile Tyr Gln Val Gln Ile Ala
            595                 600                 605
Gly Asn Gly Gln Thr Tyr Ile Arg Val Ala Asn Cys Gln Thr Val Arg
    610                 615                 620
Met Lys Glu Glu Lys Glu Val Leu Glu His Phe Ala Gly Val Phe Thr
625                 630                 635                 640
Met Met Asn Pro Leu Thr Phe Lys Glu Ile Phe Gln Thr Thr Val Pro
                    645                 650                 655
Tyr Met Val Glu Arg Ile Ser Lys Asn Tyr Ala Leu Gln Ile Val Ala
                660                 665                 670
Asn Ser Phe Leu Ala Asn Pro Thr Thr Ser Ala Leu Phe Ala Thr Ile
            675                 680                 685
Leu Val Glu Tyr Leu Leu Asp Arg Leu Pro Glu Met Gly Ser Asn Val
        690                 695                 700
Glu Leu Ser Asn Leu Tyr Leu Lys Leu Phe Lys Leu Val Phe Gly Ser
705                 710                 715                 720
Val Ser Leu Phe Ala Ala Glu Asn Glu Gln Met Leu Lys Pro His Leu
                725                 730                 735
His Lys Ile Val Asn Ser Ser Met Glu Leu Ala Gln Thr Ala Lys Glu
                740                 745                 750
Pro Tyr Asn Tyr Phe Leu Leu Leu Arg Ala Leu Phe Arg Ser Ile Gly
            755                 760                 765
Gly Gly Ser His Asp Leu Leu Tyr Gln Glu Phe Leu Pro Leu Leu Pro
    770                 775                 780
```

Asn Leu Leu Gln Gly Leu Asn Met Leu Gln Ser Gly Leu His Lys Gln
785                 790                 795                 800

His Met Lys Asp Leu Phe Val Glu Leu Cys Leu Thr Val Pro Val Arg
            805                 810                 815

Leu Ser Ser Leu Leu Pro Tyr Leu Pro Met Leu Met Asp Pro Leu Val
        820                 825                 830

Ser Ala Leu Asn Gly Ser Gln Thr Leu Val Ser Gln Gly Leu Arg Thr
            835                 840                 845

Leu Glu Leu Cys Val Asp Asn Leu Gln Pro Asp Phe Leu Tyr Asp His
850                 855                 860

Ile Gln Pro Val Arg Ala Glu Leu Met Gln Ala Leu Trp Arg Thr Leu
865                 870                 875                 880

Arg Asn Pro Ala Asp Ser Ile Ser His Val Ala Tyr Arg Val Leu Gly
            885                 890                 895

Lys Phe Gly Gly Ser Asn Arg Lys Met Leu Lys Glu Ser Gln Lys Leu
        900                 905                 910

His Tyr Val Val Thr Glu Val Gln Gly Pro Ser Ile Thr Val Glu Phe
        915                 920                 925

Ser Asp Cys Lys Ala Ser Leu Gln Leu Pro Met Glu Lys Ala Ile Glu
930                 935                 940

Thr Ala Leu Asp Cys Leu Lys Ser Ala Asn Thr Glu Pro Tyr Tyr Arg
945                 950                 955                 960

Arg Gln Ala Trp Glu Val Ile Lys Cys Phe Leu Val Ala Met Met Ser
            965                 970                 975

Leu Glu Asp Asn Lys His Ala Leu Tyr Gln Leu Leu Ala His Pro Asn
            980                 985                 990

Phe Thr Glu Lys Thr Ile Pro Asn Val Ile Ile Ser His Arg Tyr Lys
        995                 1000                1005

Ala Gln Asp Thr Pro Ala Arg Lys Thr Phe Glu Gln Ala Leu Thr
    1010                1015                1020

Gly Ala Phe Met Ser Ala Val Ile Lys Asp Leu Arg Pro Ser Ala
    1025                1030                1035

Leu Pro Phe Val Ala Ser Leu Ile Arg His Tyr Thr Met Val Ala
    1040                1045                1050

Val Ala Gln Gln Cys Gly Pro Phe Leu Leu Pro Cys Tyr Gln Val
    1055                1060                1065

Gly Ser Gln Pro Ser Thr Ala Met Phe His Ser Glu Glu Asn Gly
    1070                1075                1080

Ser Lys Gly Met Asp Pro Leu Val Leu Ile Asp Ala Ile Ala Ile
    1085                1090                1095

Cys Met Ala Tyr Glu Glu Lys Glu Leu Cys Lys Ile Gly Glu Val
    1100                1105                1110

Ala Leu Ala Val Ile Phe Asp Val Ala Ser Ile Ile Leu Gly Ser
    1115                1120                1125

Lys Glu Arg Ala Cys Gln Leu Pro Leu Phe Ser Tyr Ile Val Glu
    1130                1135                1140

Arg Leu Cys Ala Cys Cys Tyr Glu Gln Ala Trp Tyr Ala Lys Leu
    1145                1150                1155

Gly Gly Val Val Ser Ile Lys Phe Leu Met Glu Arg Leu Pro Leu
    1160                1165                1170

Thr Trp Val Leu Gln Asn Gln Thr Phe Leu Lys Ala Leu Leu
    1175                1180                1185

-continued

```
Phe Val Met Met Asp Leu Thr Gly Glu Val Ser Asn Gly Ala Val
    1190                1195                1200
Ala Met Ala Lys Thr Thr Leu Glu Gln Leu Leu Met Arg Cys Ala
    1205                1210                1215
Thr Pro Leu Lys Asp Glu Glu Arg Ala Glu Glu Ile Val Ala Ala
    1220                1225                1230
Gln Glu Lys Ser Phe His His Val Thr His Asp Leu Val Arg Glu
    1235                1240                1245
Val Thr Ser Pro Asn Ser Thr Val Arg Lys Gln Ala Met His Ser
    1250                1255                1260
Leu Gln Val Leu Ala Gln Val Thr Gly Lys Ser Val Thr Val Ile
    1265                1270                1275
Met Glu Pro His Lys Glu Val Leu Gln Asp Met Val Pro Pro Lys
    1280                1285                1290
Lys His Leu Leu Arg His Gln Pro Ala Asn Ala Gln Ile Gly Leu
    1295                1300                1305
Met Glu Gly Asn Thr Phe Cys Thr Thr Leu Gln Pro Arg Leu Phe
    1310                1315                1320
Thr Met Asp Leu Asn Val Val Glu His Lys Val Phe Tyr Thr Glu
    1325                1330                1335
Leu Leu Asn Leu Cys Glu Ala Glu Asp Ser Ala Leu Thr Lys Leu
    1340                1345                1350
Pro Cys Tyr Lys Ser Leu Pro Ser Leu Val Pro Leu Arg Ile Ala
    1355                1360                1365
Ala Leu Asn Ala Leu Ala Ala Cys Asn Tyr Leu Pro Gln Ser Arg
    1370                1375                1380
Glu Lys Ile Ile Ala Ala Leu Phe Lys Ala Leu Asn Ser Thr Asn
    1385                1390                1395
Ser Glu Leu Gln Glu Ala Gly Glu Ala Cys Met Arg Lys Phe Leu
    1400                1405                1410
Glu Gly Ala Thr Ile Glu Val Asp Gln Ile His Thr His Met Arg
    1415                1420                1425
Pro Leu Leu Met Met Leu Gly Asp Tyr Arg Ser Leu Thr Leu Asn
    1430                1435                1440
Val Val Asn Arg Leu Thr Ser Val Thr Arg Leu Phe Pro Asn Ser
    1445                1450                1455
Phe Asn Asp Lys Phe Cys Asp Gln Met Met Gln His Leu Arg Lys
    1460                1465                1470
Trp Met Glu Val Val Val Ile Thr His Lys Gly Gly Gln Arg Ser
    1475                1480                1485
Asp Gly Asn Glu Ser Ile Ser Glu Cys Gly Arg Cys Pro Leu Ser
    1490                1495                1500
Pro Phe Cys Gln Phe Glu Glu Met Lys Ile Cys Ser Ala Ile Ile
    1505                1510                1515
Asn Leu Phe His Leu Ile Pro Ala Ala Pro Gln Thr Leu Val Lys
    1520                1525                1530
Pro Leu Leu Glu Val Val Met Lys Thr Glu Arg Ala Met Leu Ile
    1535                1540                1545
Glu Ala Gly Ser Pro Phe Arg Glu Pro Leu Ile Lys Phe Leu Thr
    1550                1555                1560
Arg His Pro Ser Gln Thr Val Glu Leu Phe Met Met Glu Ala Thr
    1565                1570                1575
Leu Asn Asp Pro Gln Trp Ser Arg Met Phe Met Ser Phe Leu Lys
```

-continued

```
            1580                1585                1590
His Lys Asp Ala Arg Pro Leu Arg Asp Val Leu Ala Ala Asn Pro
    1595                1600                1605
Asn Arg Phe Ile Thr Leu Leu Leu Pro Gly Gly Ala Gln Thr Ala
    1610                1615                1620
Val Arg Pro Gly Ser Pro Ser Thr Ser Thr Met Arg Leu Asp Leu
    1625                1630                1635
Gln Phe Gln Ala Ile Lys Ile Ile Ser Ile Ile Val Lys Asn Asp
    1640                1645                1650
Asp Ser Trp Leu Ala Ser Gln His Ser Leu Val Ser Gln Leu Arg
    1655                1660                1665
Arg Val Trp Val Ser Glu Asn Phe Gln Glu Arg His Arg Lys Glu
    1670                1675                1680
Asn Met Ala Ala Thr Asn Trp Lys Glu Pro Lys Leu Leu Ala Tyr
    1685                1690                1695
Cys Leu Leu Asn Tyr Cys Lys Arg Asn Tyr Gly Asp Ile Glu Leu
    1700                1705                1710
Leu Phe Gln Leu Leu Arg Ala Phe Thr Gly Arg Phe Leu Cys Asn
    1715                1720                1725
Met Thr Phe Leu Lys Glu Tyr Met Glu Glu Ile Pro Lys Asn
    1730                1735                1740
Tyr Ser Ile Ala Gln Lys Arg Ala Leu Phe Phe Arg Phe Val Asp
    1745                1750                1755
Phe Asn Asp Pro Asn Phe Gly Asp Glu Leu Lys Ala Lys Val Leu
    1760                1765                1770
Gln His Ile Leu Asn Pro Ala Phe Leu Tyr Ser Phe Glu Lys Gly
    1775                1780                1785
Glu Gly Glu Gln Leu Leu Gly Pro Pro Asn Pro Glu Gly Asp Asn
    1790                1795                1800
Pro Glu Ser Ile Thr Ser Val Phe Ile Thr Lys Val Leu Asp Pro
    1805                1810                1815
Glu Lys Gln Ala Asp Met Leu Asp Ser Leu Arg Ile Tyr Leu Leu
    1820                1825                1830
Gln Tyr Ala Thr Leu Leu Val Glu His Ala Pro His His Ile His
    1835                1840                1845
Asp Asn Asn Lys Asn Arg Asn Ser Lys Leu Arg Arg Leu Met Thr
    1850                1855                1860
Phe Ala Trp Pro Cys Leu Leu Ser Lys Ala Cys Val Asp Pro Ala
    1865                1870                1875
Cys Lys Tyr Ser Gly His Leu Leu Leu Ala His Ile Ile Ala Lys
    1880                1885                1890
Phe Ala Ile His Lys Lys Ile Val Leu Gln Val Phe His Ser Leu
    1895                1900                1905
Leu Lys Ala His Ala Met Glu Ala Arg Ala Ile Val Arg Gln Ala
    1910                1915                1920
Met Ala Ile Leu Thr Pro Ala Val Pro Ala Arg Met Glu Asp Gly
    1925                1930                1935
His Gln Met Leu Thr His Trp Thr Arg Lys Ile Ile Val Glu Glu
    1940                1945                1950
Gly His Thr Val Pro Gln Leu Val His Ile Leu His Leu Ile Val
    1955                1960                1965
Gln His Phe Lys Val Tyr Tyr Pro Val Arg His His Leu Val Gln
    1970                1975                1980
```

-continued

His Met Val Ser Ala Met Gln Arg Leu Gly Phe Thr Pro Ser Val
    1985            1990                1995

Thr Ile Glu Gln Arg Arg Leu Ala Val Asp Leu Ser Glu Val Val
    2000            2005                2010

Ile Lys Trp Glu Leu Gln Arg Ile Lys Asp Gln Gln Pro Asp Ser
    2015            2020                2025

Asp Met Asp Pro Asn Ser Ser Gly Glu Gly Val Asn Ser Val Ser
    2030            2035                2040

Ser Ser Ile Lys Arg Gly Leu Ser Val Asp Ser Ala Gln Glu Val
    2045            2050                2055

Lys Arg Phe Arg Thr Ala Thr Gly Ala Ile Ser Ala Val Phe Gly
    2060            2065                2070

Arg Ser Gln Ser Leu Pro Gly Ala Asp Ser Leu Leu Ala Lys Pro
    2075            2080                2085

Ile Asp Lys Gln His Thr Asp Thr Val Val Asn Phe Leu Ile Arg
    2090            2095                2100

Val Ala Cys Gln Val Asn Asp Asn Thr Asn Thr Ala Gly Ser Pro
    2105            2110                2115

Gly Glu Val Leu Ser Arg Arg Cys Val Asn Leu Leu Lys Thr Ala
    2120            2125                2130

Leu Arg Pro Asp Met Trp Pro Lys Ser Glu Leu Lys Leu Gln Trp
    2135            2140                2145

Phe Asp Lys Leu Leu Met Thr Val Glu Gln Pro Asn Gln Val Asn
    2150            2155                2160

Tyr Gly Asn Ile Cys Thr Gly Leu Glu Val Leu Ser Phe Leu Leu
    2165            2170                2175

Thr Val Leu Gln Ser Pro Ala Ile Leu Ser Ser Phe Lys Pro Leu
    2180            2185                2190

Gln Arg Gly Ile Ala Ala Cys Met Thr Cys Gly Asn Thr Lys Val
    2195            2200                2205

Leu Arg Ala Val His Ser Leu Leu Ser Arg Leu Met Ser Ile Phe
    2210            2215                2220

Pro Thr Glu Pro Ser Thr Ser Ser Val Ala Ser Lys Tyr Glu Glu
    2225            2230                2235

Leu Glu Cys Leu Tyr Ala Ala Val Gly Lys Val Ile Tyr Glu Gly
    2240            2245                2250

Leu Thr Asn Tyr Glu Lys Ala Thr Asn Ala Asn Pro Ser Gln Leu
    2255            2260                2265

Phe Gly Thr Leu Met Ile Leu Lys Ser Ala Cys Ser Asn Asn Pro
    2270            2275                2280

Ser Tyr Ile Asp Arg Leu Ile Ser Val Phe Met Arg Ser Leu Gln
    2285            2290                2295

Lys Met Val Arg Glu His Leu Asn Pro Gln Ala Ala Ser Gly Ser
    2300            2305                2310

Thr Glu Ala Thr Ser Gly Thr Ser Glu Leu Val Met Leu Ser Leu
    2315            2320                2325

Glu Leu Val Lys Thr Arg Leu Ala Val Met Ser Met Glu Met Arg
    2330            2335                2340

Lys Asn Phe Ile Gln Ala Ile Leu Thr Ser Leu Ile Glu Lys Ser
    2345            2350                2355

Pro Asp Ala Lys Ile Leu Arg Ala Val Val Lys Ile Val Glu Glu
    2360            2365                2370

```
Trp Val Lys Asn Asn Ser Pro Met Ala Ala Asn Gln Thr Pro Thr
2375                2380                2385

Leu Arg Glu Lys Ser Ile Leu Leu Val Lys Met Met Thr Tyr Ile
2390                2395                2400

Glu Lys Arg Phe Pro Glu Asp Leu Glu Leu Asn Ala Gln Phe Leu
2405                2410                2415

Asp Leu Val Asn Tyr Val Tyr Arg Asp Glu Thr Leu Ser Gly Ser
2420                2425                2430

Glu Leu Thr Ala Lys Leu Glu Pro Ala Phe Leu Ser Gly Leu Arg
2435                2440                2445

Cys Ala Gln Pro Leu Ile Arg Ala Lys Phe Phe Glu Val Phe Asp
2450                2455                2460

Asn Ser Met Lys Arg Arg Val Tyr Glu Arg Leu Leu Tyr Val Thr
2465                2470                2475

Cys Ser Gln Asn Trp Glu Ala Met Gly Asn His Phe Trp Ile Lys
2480                2485                2490

Gln Cys Ile Glu Leu Leu Leu Ala Val Cys Glu Lys Ser Thr Pro
2495                2500                2505

Ile Gly Thr Ser Cys Gln Gly Ala Met Leu Pro Ser Ile Thr Asn
2510                2515                2520

Val Ile Asn Leu Ala Asp Ser His Asp Arg Ala Ala Phe Ala Met
2525                2530                2535

Val Thr His Val Lys Gln Glu Pro Arg Glu Arg Glu Asn Ser Glu
2540                2545                2550

Ser Lys Glu Glu Asp Val Glu Ile Asp Ile Glu Leu Ala Pro Gly
2555                2560                2565

Asp Gln Thr Ser Thr Pro Lys Thr Lys Glu Leu Ser Glu Lys Asp
2570                2575                2580

Ile Gly Asn Gln Leu His Met Leu Thr Asn Arg His Asp Lys Phe
2585                2590                2595

Leu Asp Thr Leu Arg Glu Val Lys Thr Gly Ala Leu Leu Ser Ala
2600                2605                2610

Phe Val Gln Leu Cys His Ile Ser Thr Thr Leu Ala Glu Lys Thr
2615                2620                2625

Trp Val Gln Leu Phe Pro Arg Leu Trp Lys Ile Leu Ser Asp Arg
2630                2635                2640

Gln Gln His Ala Leu Ala Gly Glu Ile Ser Pro Phe Leu Cys Ser
2645                2650                2655

Gly Ser His Gln Val Gln Arg Asp Cys Gln Pro Ser Ala Leu Asn
2660                2665                2670

Cys Phe Val Glu Ala Met Ser Gln Cys Val Pro Ile Pro Ile
2675                2680                2685

Arg Pro Cys Val Leu Lys Tyr Leu Gly Lys Thr His Asn Leu Trp
2690                2695                2700

Phe Arg Ser Thr Leu Met Leu Glu His Gln Ala Phe Glu Lys Gly
2705                2710                2715

Leu Ser Leu Gln Ile Lys Pro Lys Gln Thr Thr Glu Phe Tyr Glu
2720                2725                2730

Gln Glu Ser Ile Thr Pro Pro Gln Gln Glu Ile Leu Asp Ser Leu
2735                2740                2745

Ala Glu Leu Tyr Ser Leu Leu Gln Glu Glu Asp Met Trp Ala Gly
2750                2755                2760

Leu Trp Gln Lys Arg Cys Lys Tyr Ser Glu Thr Ala Thr Ala Ile
```

-continued

```
            2765                2770                2775

Ala Tyr Glu Gln His Gly Phe Phe Glu Gln Ala Gln Glu Ser Tyr
        2780                2785                2790

Glu Lys Ala Met Asp Lys Ala Lys Lys Glu His Glu Arg Ser Asn
        2795                2800                2805

Ala Ser Pro Ala Ile Phe Pro Glu Tyr Gln Leu Trp Glu Asp His
        2810                2815                2820

Trp Ile Arg Cys Ser Lys Glu Leu Asn Gln Trp Glu Ala Leu Thr
        2825                2830                2835

Glu Tyr Gly Gln Ser Lys Gly His Ile Asn Pro Tyr Leu Val Leu
        2840                2845                2850

Glu Cys Ala Trp Arg Val Ser Asn Trp Thr Ala Met Lys Glu Ala
        2855                2860                2865

Leu Val Gln Val Glu Val Ser Cys Pro Lys Glu Met Ala Trp Lys
        2870                2875                2880

Val Asn Met Tyr Arg Gly Tyr Leu Ala Ile Cys His Pro Glu Glu
        2885                2890                2895

Gln Gln Leu Ser Phe Ile Glu Arg Leu Val Glu Met Ala Ser Ser
        2900                2905                2910

Leu Ala Ile Arg Glu Trp Arg Arg Leu Pro His Val Val Ser His
        2915                2920                2925

Val His Thr Pro Leu Leu Gln Ala Ala Gln Gln Ile Ile Glu Leu
        2930                2935                2940

Gln Glu Ala Ala Gln Ile Asn Ala Gly Leu Gln Pro Thr Asn Leu
        2945                2950                2955

Gly Arg Asn Asn Ser Leu His Asp Met Lys Thr Val Val Lys Thr
        2960                2965                2970

Trp Arg Asn Arg Leu Pro Ile Val Ser Asp Asp Leu Ser His Trp
        2975                2980                2985

Ser Ser Ile Phe Met Trp Arg Gln His His Tyr Gln Gly Lys Pro
        2990                2995                3000

Thr Trp Ser Gly Met His Ser Ser Ile Val Thr Ala Tyr Glu
        3005                3010                3015

Asn Ser Ser Gln His Asp Pro Ser Ser Asn Asn Ala Met Leu Gly
        3020                3025                3030

Val His Ala Ser Ala Ser Ala Ile Ile Gln Tyr Gly Lys Ile Ala
        3035                3040                3045

Arg Lys Gln Gly Leu Val Asn Ala Leu Asp Ile Leu Ser Arg Ile
        3050                3055                3060

His Thr Ile Pro Thr Val Pro Ile Val Asp Cys Phe Gln Lys Ile
        3065                3070                3075

Arg Gln Gln Val Lys Cys Tyr Leu Gln Leu Ala Gly Val Met Gly
        3080                3085                3090

Lys Asn Glu Cys Met Gln Gly Leu Glu Val Ile Glu Ser Thr Asn
        3095                3100                3105

Leu Lys Tyr Phe Thr Lys Glu Met Thr Ala Glu Phe Tyr Ala Leu
        3110                3115                3120

Lys Gly Met Phe Leu Ala Gln Ile Asn Lys Ser Glu Glu Ala Asn
        3125                3130                3135

Lys Ala Phe Ser Ala Ala Val Gln Met His Asp Val Leu Val Lys
        3140                3145                3150

Ala Trp Ala Met Trp Gly Asp Tyr Leu Glu Asn Ile Phe Val Lys
        3155                3160                3165
```

-continued

Glu Arg Gln Leu His Leu Gly Val Ser Ala Ile Thr Cys Tyr Leu
3170             3175             3180

His Ala Cys Arg His Gln Asn Glu Ser Lys Ser Arg Lys Tyr Leu
3185             3190             3195

Ala Lys Val Leu Trp Leu Leu Ser Phe Asp Asp Lys Asn Thr
3200             3205             3210

Leu Ala Asp Ala Val Asp Lys Tyr Cys Ile Gly Val Pro Pro Ile
3215             3220             3225

Gln Trp Leu Ala Trp Ile Pro Gln Leu Leu Thr Cys Leu Val Gly
3230             3235             3240

Ser Glu Gly Lys Leu Leu Asn Leu Ile Ser Gln Val Gly Arg
3245             3250             3255

Val Tyr Pro Gln Ala Val Tyr Phe Pro Ile Arg Thr Leu Tyr Leu
3260             3265             3270

Thr Leu Lys Ile Glu Gln Arg Glu Arg Tyr Lys Ser Asp Pro Gly
3275             3280             3285

Pro Ile Arg Ala Thr Ala Pro Met Trp Arg Cys Ser Arg Ile Met
3290             3295             3300

His Met Gln Arg Glu Leu His Pro Thr Leu Leu Ser Ser Leu Glu
3305             3310             3315

Gly Ile Val Asp Gln Met Val Trp Phe Arg Glu Asn Trp His Glu
3320             3325             3330

Glu Val Leu Arg Gln Leu Gln Gln Gly Leu Ala Lys Cys Tyr Ser
3335             3340             3345

Val Ala Phe Glu Lys Ser Gly Ala Val Ser Asp Ala Lys Ile Thr
3350             3355             3360

Pro His Thr Leu Asn Phe Val Lys Lys Leu Val Ser Thr Phe Gly
3365             3370             3375

Val Gly Leu Glu Asn Val Ser Asn Val Ser Thr Met Phe Ser Ser
3380             3385             3390

Ala Ala Ser Glu Ser Leu Ala Arg Arg Ala Gln Ala Thr Ala Gln
3395             3400             3405

Asp Pro Val Phe Gln Lys Leu Lys Gly Gln Phe Thr Thr Asp Phe
3410             3415             3420

Asp Phe Ser Val Pro Gly Ser Met Lys Leu His Asn Leu Ile Ser
3425             3430             3435

Lys Leu Lys Lys Trp Ile Lys Ile Leu Glu Ala Lys Thr Lys Gln
3440             3445             3450

Leu Pro Lys Phe Phe Leu Ile Glu Glu Lys Cys Arg Phe Leu Ser
3455             3460             3465

Asn Phe Ser Ala Gln Thr Ala Glu Val Glu Ile Pro Gly Glu Phe
3470             3475             3480

Leu Met Pro Lys Pro Thr His Tyr Tyr Ile Lys Ile Ala Arg Phe
3485             3490             3495

Met Pro Arg Val Glu Ile Val Gln Lys His Asn Thr Ala Ala Arg
3500             3505             3510

Arg Leu Tyr Ile Arg Gly His Asn Gly Lys Ile Tyr Pro Tyr Leu
3515             3520             3525

Val Met Asn Asp Ala Cys Leu Thr Glu Ser Arg Arg Glu Glu Arg
3530             3535             3540

Val Leu Gln Leu Leu Arg Leu Leu Asn Pro Cys Leu Glu Lys Arg
3545             3550             3555

-continued

| | | | | | | | | | | | |
|---|---|---|---|---|---|---|---|---|---|---|---|
| Lys | Glu 3560 | Thr | Thr | Lys | Arg 3565 | His | Leu | Phe | Phe 3570 | Thr | Val | Pro | Arg | Val |
| Val | Ala 3575 | Val | Ser | Pro | Gln 3580 | Met | Arg | Leu | Val 3585 | Glu | Asp | Asn | Pro | Ser |
| Ser | Leu 3590 | Ser | Leu | Val | Glu 3595 | Ile | Tyr | Lys | Gln 3600 | Arg | Cys | Ala | Lys | Lys |
| Gly | Ile 3605 | Glu | His | Asp | Asn 3610 | Pro | Ile | Ser | Arg 3615 | Tyr | Tyr | Asp | Arg | Leu |
| Ala | Thr 3620 | Val | Gln | Ala | Arg 3625 | Gly | Thr | Gln | Ala 3630 | Ser | His | Gln | Val | Leu |
| Arg | Asp 3635 | Ile | Leu | Lys | Glu 3640 | Val | Gln | Ser | Asn 3645 | Met | Val | Pro | Arg | Ser |
| Met | Leu 3650 | Lys | Glu | Trp | Ala 3655 | Leu | His | Thr | Phe 3660 | Pro | Asn | Ala | Thr | Asp |
| Tyr | Trp 3665 | Thr | Phe | Arg | Lys 3670 | Met | Phe | Thr | Ile 3675 | Gln | Leu | Ala | Leu | Ile |
| Gly | Phe 3680 | Ala | Glu | Phe | Val 3685 | Leu | His | Leu | Asn 3690 | Arg | Leu | Asn | Pro | Glu |
| Met | Leu 3695 | Gln | Ile | Ala | Gln 3700 | Asp | Thr | Gly | Lys 3705 | Leu | Asn | Val | Ala | Tyr |
| Phe | Arg 3710 | Phe | Asp | Ile | Asn 3715 | Asp | Ala | Thr | Gly 3720 | Asp | Leu | Asp | Ala | Asn |
| Arg | Pro 3725 | Val | Pro | Phe | Arg 3730 | Leu | Thr | Pro | Asn 3735 | Ile | Ser | Glu | Phe | Leu |
| Thr | Thr 3740 | Ile | Gly | Val | Ser 3745 | Gly | Pro | Leu | Thr 3750 | Ala | Ser | Met | Ile | Ala |
| Val | Ala 3755 | Arg | Cys | Phe | Ala 3760 | Gln | Pro | Asn | Phe 3765 | Lys | Val | Asp | Gly | Ile |
| Leu | Lys 3770 | Thr | Val | Leu | Arg 3775 | Asp | Glu | Ile | Ala 3780 | Trp | His | Lys | Lys |
| Thr | Gln 3785 | Glu | Asp | Thr | Ser 3790 | Ser | Pro | Leu | Ser 3795 | Ala | Ala | Gly | Gln | Pro |
| Glu | Asn 3800 | Met | Asp | Ser | Gln 3805 | Gln | Leu | Val | Ser 3810 | Leu | Val | Gln | Lys | Ala |
| Val | Thr 3815 | Ala | Ile | Met | Thr 3820 | Arg | Leu | His | Asn 3825 | Leu | Ala | Gln | Phe | Glu |
| Gly | Gly 3830 | Glu | Ser | Lys | Val 3835 | Asn | Thr | Leu | Val 3840 | Ala | Ala | Ala | Asn | Ser |
| Leu | Asp 3845 | Asn | Leu | Cys | Arg 3850 | Met | Asp | Pro | Ala 3855 | Trp | His | Pro | Trp | Leu |